(12) United States Patent
Zharov

(10) Patent No.: US 12,150,735 B2
(45) Date of Patent: *Nov. 26, 2024

(54) DEVICE AND METHOD FOR IN VIVO FLOW CYTOMETRY USING THE DETECTION OF PHOTOACOUSTIC WAVES

(71) Applicant: Bioventures, LLC, Little Rock, AR (US)

(72) Inventor: Vladimir Pavlovich Zharov, Little Rock, AR (US)

(73) Assignee: Bioventures, LLC, Little Rock, AR (US)

( * ) Notice: Subject to any disclaimer, the term of this patent is extended or adjusted under 35 U.S.C. 154(b) by 129 days.

This patent is subject to a terminal disclaimer.

(21) Appl. No.: 17/668,971

(22) Filed: Feb. 10, 2022

(65) Prior Publication Data

US 2022/0160238 A1 May 26, 2022

Related U.S. Application Data

(60) Continuation of application No. 14/939,039, filed on Nov. 12, 2015, now Pat. No. 11,259,704, which is a (Continued)

(51) Int. Cl.
*A61B 5/00* (2006.01)
*A61B 5/02* (2006.01)
(Continued)

(52) U.S. Cl.
CPC .......... *A61B 5/0095* (2013.01); *A61B 5/0059* (2013.01); *A61B 5/02007* (2013.01);
(Continued)

(58) Field of Classification Search
CPC . A61B 5/0095; A61B 5/0059; A61B 5/02007; A61B 5/412; A61B 5/415;
(Continued)

(56) References Cited

U.S. PATENT DOCUMENTS 4,333,474 A 6/1982 Nigam
5,972,721 A 10/1999 Bruno et al.
(Continued)

FOREIGN PATENT DOCUMENTS

DE 10343442 A1 4/2005
WO 2006049570 A2 5/2006
(Continued)

OTHER PUBLICATIONS

Sarimollaoglu, M. et al., "Nonlinear photoacoustic signal amplification from single targets in absorption background," Photoacoustics, Article in Press, 2013, pp. 1-11, vol. 12, Elsevier.
(Continued)

*Primary Examiner* — Hien N Nguyen
(74) *Attorney, Agent, or Firm* — Polsinelli PC

(57) ABSTRACT

A photoacoustic flow cytometry (PAFC) device for the in vivo detection of cells circulating in blood or lymphatic vessels is described. Ultrasound transducers attached to the skin of an organism detect the photoacoustic ultrasound waves emitted by target objects in response to their illumination by at least one pulse of laser energy delivered using at least one wavelength. The wavelengths of the laser light pulse may be varied to optimize the absorption of the laser energy by the target object. Target objects detected by the device may be unlabelled biological cells or cell products, contrast agents, or biological cells labeled with one or more contrast agents.

37 Claims, 22 Drawing Sheets

Related U.S. Application Data continuation of application No. 13/661,551, filed on Oct. 26, 2012, now Pat. No. 9,217,703, which is a division of application No. 12/334,217, filed on Dec. 12, 2008, now abandoned.

(60) Provisional application No. 61/013,543, filed on Dec. 13, 2007.

(51) Int. Cl.
| | |
|---|---|
| *A61B 8/08* | (2006.01) |
| *A61B 18/00* | (2006.01) |
| *A61B 18/20* | (2006.01) |
| *A61K 49/22* | (2006.01) |
| *G01N 15/14* | (2024.01) |
| *G01N 15/1434* | (2024.01) |
| *G01N 21/17* | (2006.01) |
| *G01N 21/39* | (2006.01) |

(52) U.S. Cl.
CPC ............ *A61B 5/412* (2013.01); *A61B 5/415* (2013.01); *A61B 5/416* (2013.01); *A61B 5/418* (2013.01); *A61B 5/7278* (2013.01); *A61B 18/20* (2013.01); *A61K 49/22* (2013.01); *G01N 21/1702* (2013.01); *G01N 21/39* (2013.01); *A61B 8/08* (2013.01); *A61B 2018/00642* (2013.01); *A61B 2018/20351* (2017.05); *A61B 2018/20357* (2017.05); *A61B 2018/20361* (2017.05); *A61B 2018/207* (2013.01); *G01N 15/1425* (2013.01); *G01N 15/1434* (2013.01); *G01N 15/147* (2013.01); *G01N 2015/1477* (2013.01); *G01N 2201/0697* (2013.01)

(58) Field of Classification Search
CPC ....... A61B 5/416; A61B 5/418; A61B 5/7278; A61B 18/20; A61B 8/08; A61B 2018/00642; A61B 2018/20351; A61B 2018/20357; A61B 2018/20361; A61B 2018/207; A61K 49/22; G01N 21/1702; G01N 21/39; G01N 15/1425; G01N 15/1434; G01N 15/147; G01N 2015/1477; G01N 2201/0697

See application file for complete search history.

(56) References Cited

U.S. PATENT DOCUMENTS

| | | |
|---|---|---|
| 6,368,318 B1 | 4/2002 | Visuri et al. |
| 6,428,531 B1 | 8/2002 | Visuri et al. |
| 6,466,806 B1 | 10/2002 | Geva et al. |
| 6,514,203 B2 | 2/2003 | Bukshpan |
| 6,530,944 B2 | 3/2003 | West et al. |
| 6,710,871 B1 | 3/2004 | Goix |
| 6,833,540 B2 | 12/2004 | Mackenzie et al. |
| 6,846,288 B2 | 1/2005 | Nagar et al. |
| 7,220,385 B2 | 5/2007 | Blecka et al. |
| 7,500,953 B2 | 3/2009 | Oraevsky et al. |
| 9,144,383 B2 | 9/2015 | Zharov |
| 9,217,703 B2 | 12/2015 | Zharov |
| 9,451,884 B2 | 9/2016 | Zharov et al. |
| 10,342,430 B2 | 7/2019 | Zharov |
| 10,945,610 B2 | 3/2021 | Zharov |
| 11,154,360 B2 | 10/2021 | Zharov |
| 11,259,704 B2 | 3/2022 | Zharov |
| 11,723,540 B2 | 8/2023 | Smeltzer et al. |
| 2002/0099283 A1 | 7/2002 | Christ et al. |
| 2003/0216663 A1 | 11/2003 | Jersey-Willuhn et al. |
| 2004/0039379 A1 | 2/2004 | Viator et al. |
| 2004/0188602 A1 | 9/2004 | Chinn et al. |
| 2005/0004458 A1 | 1/2005 | Kanayama et al. |
| 2005/0106739 A1 | 5/2005 | Cabuz et al. |
| 2005/0124869 A1 | 6/2005 | Hefti et al. |
| 2005/0175540 A1 | 8/2005 | Oraevsky et al. |
| 2006/0078949 A1 | 4/2006 | Offer et al. |
| 2006/0122583 A1 | 6/2006 | Pesach et al. |
| 2006/0184042 A1 | 8/2006 | Wang et al. |
| 2007/0015978 A1 | 1/2007 | Kanayama et al. |
| 2007/0015992 A1 | 1/2007 | Filkins et al. |
| 2007/0121697 A1 | 5/2007 | Burgholzer et al. |
| 2007/0213613 A1 | 9/2007 | Shida et al. |
| 2007/0232940 A1 | 10/2007 | Fine et al. |
| 2007/0269345 A1 | 11/2007 | Schilffarth et al. |
| 2007/0292495 A1 | 12/2007 | Ludwig et al. |
| 2008/0149566 A1 | 6/2008 | Messersmith et al. |
| 2008/0160090 A1 | 7/2008 | Oraevsky et al. |
| 2008/0269847 A1 | 10/2008 | Nemenov |
| 2008/0269849 A1 | 10/2008 | Lewis |
| 2009/0093713 A1 | 4/2009 | Hyde et al. |
| 2009/0156932 A1 | 6/2009 | Zharov |
| 2009/0227997 A1 | 9/2009 | Wang et al. |
| 2009/0292195 A1 | 11/2009 | Boydon et al. |
| 2009/0326614 A1 | 12/2009 | El-Sayed et al. |
| 2010/0278923 A1 | 11/2010 | Chen et al. |
| 2011/0105867 A1 | 5/2011 | Schultz et al. |
| 2011/0117028 A1 | 5/2011 | Zharov |
| 2011/0134426 A1 | 6/2011 | Kaduchak et al. |
| 2011/0218140 A1 | 9/2011 | Gonsalves et al. |
| 2011/0306865 A1 | 12/2011 | Thornton et al. |
| 2012/0022360 A1 | 1/2012 | Kemp |
| 2012/0065490 A1 | 3/2012 | Zharov et al. |
| 2012/0179227 A1 | 7/2012 | Schomacker et al. |
| 2012/0202278 A1 | 8/2012 | Wagner et al. |
| 2012/0237605 A1 | 9/2012 | Messersmith et al. |
| 2013/0030307 A1 | 1/2013 | Rajan et al. |
| 2013/0060122 A1 | 3/2013 | Zharov |
| 2013/0123604 A1 | 5/2013 | Oyama |
| 2015/0065685 A1 | 3/2015 | Arany et al. |
| 2015/0150463 A1 | 6/2015 | Smeltzer et al. |
| 2015/0282716 A1 | 10/2015 | Smeltzer et al. |
| 2015/0335741 A1 | 11/2015 | Smeltzer et al. |
| 2015/0351640 A1 | 12/2015 | Zharov |
| 2016/0058297 A1 | 3/2016 | Zharov |
| 2016/0354150 A1 | 12/2016 | Zharov |
| 2018/0000351 A1 | 1/2018 | Zharov |
| 2021/0251491 A1 | 8/2021 | Zharov |

FOREIGN PATENT DOCUMENTS

| | | |
|---|---|---|
| WO | 2013067419 A1 | 5/2013 |
| WO | 2014052449 A1 | 4/2014 |
| WO | 2016109831 A1 | 7/2016 |
| WO | 2016196791 A1 | 12/2016 |

OTHER PUBLICATIONS

Schmid, T. et al., "Process analysis of biofilms by photoacoustic spectroscopy," Anal. Bioanal. Chem., 2003, pp. 1124-1129, vol. 375.

Schmid, T. et al., "Photoacoustic absorption spectra of biofilms," Review of Scientific Instruments, Jan. 2003, pp. 755-757, vol. 74, No. 1.

Schmidt-Kittler, O. et al., "From latent disseminated cells to overt metastasis: Genetic analysis of systemic cancer progression," PNAS, Jun. 24, 2003, pp. 7737-7742, vol. 100. No. 13.

Setia, N. et al., "Profiling of ABC transporters ABCB5, ABCF2, and nestin-positive stem cells in nevi, in situ and invasive melanoma," Mod. Pathol., 2012, pp. 1169-1175, vol. 25.

Shao, J. et al., "Photothermal nanodrugs: potential of TNF-gold nanospheres for cancer theranostics," Nature Scientific Reports, 2013, pp. 1-9, vol. 3, No. 1293, Nature Publishing Group.

Shashkov, E. et al., "Quantum dots as multimodal photoacoustic and photothermal contrast agents," NIH Public Access Author Manuscript, Nov. 1, 2009, pp. 1-13, published in final edited form as Nano Lett., Nov. 2008, pp. 3953-3958, vol. 8, No. 11.

Shashkov, E. et al., "Photothermal and photoacoustic Raman cytometry in vitro and in vivo," Opt. Exp., Mar. 29, 2010, pp. 6929-6944, vol. 18, No. 7.

(56) References Cited

OTHER PUBLICATIONS

Shibue, T. et al., "Metastatic colonization: Settlement, adaptation and propagation of tumor cells in a foreign tissue environment," Semin. Cancer Biol., 2011, pp. 99-106, vol. 21, Elsevier Ltd.

Sieuwerts, A. et al., "Anti-Epithelial Cell Adhesion Molecule Antibodies and the Detection of Circulating Normal-Like Breast Tumor Cells," J. Natl. Cancer Inst., Jan. 7, 2009, pp. 61-66, vol. 101, No. 1.

Sleeman, J. et al., "Do all roads lead to Rome? Routes to metastasis development," Int. J. Cancer, 2011, pp. 2511-2526, vol. 128.

Stott, S. et al., "Isolation of circulating tumor cells using a microvertex-generating herringbone-chip," PNAS, Oct. 26, 2010, pp. 18392-18397, vol. 107, No. 43.

Tamaki, E. et al., "Single-Cell Analysis by a Scanning Thermal Lens Microscope with a Microchip: Direct Monitoring of Cytochrome c Distribution during Apoptosis Process," Anal. Chem., Apr. 1, 2002, pp. 1560-1564, vol. 74, No. 7.

Tanev, S. et al., "Flow Cytometry with Gold Nanoparticles and their Clusters as scattering Contrast Agents: FDTD Simulation of Light-Cell Interaction," NIH Public Access Author Manuscript, Sep. 1, 2010, pp. 1-24, published in final edited form as J. Biophotonics, Sep. 2009, pp. 505-520, vol. 2, No. 8-9.

Tibbe, A. et al., "Statistical Considerations for Enumeration of Circulating Tumor Cells," Cytometry Part A, 2007, pp. 154-162, vol. 71A.

Tokeshi, M. et al., "Determination of Subyoctomole Amounts of Nonfluorescent Molecules Using a Thermal Lens Microscope: Subsingle-Molecule Determination," Anal. Chem., May 1, 2001, pp. 2112-2116, vol. 73, No. 9.

Tuchin, V. et al., "Towards in vivo flow cytometry," HHS Public Access Author Manuscript, Mar. 2, 2016, pp. 1-4, published in final edited form as J. Biophotonics, Sep. 2009, pp. 457-458, vol. 2, No. 0.

Tuchin, V. et al., "In Vivo Flow Cytometry: A Horizon of Opportunities," Cytometry Part A, 2011, pp. 737-745, vol. 79A.

Tuchin, V. et al., "In vivo Image Flow Cytometry," In: Advanced Optical Flow Cytometry: Methods and Disease Diagnoses, V. Tuchin, ed., 2011, pp. 387-431, Chapter 14, Wiley-VCH Verlag Gmbh & Co. KGaA, Weinheim, Germany.

Tuchin, V. et al., "In vivo photothermal and photoacoustic flow cytometry," In: Advanced Optical Flow Cytometry: Methods and Disease Diagnoses, V. Tuchin, ed., 2011, pp. 501-571, Chapter 17, Wiley-VCH Verlag Gmbh & Co. KGaA, Weinheim, Germany.

Ulmer, A. et al., "Detecting Circulating Melanoma Cells," J. Invest. Dermatol., 2011, pp. 1774-1775, vol. 131.

Van Dijk, M. et al., "Absorption and scattering microscopy of single metal nanoparticles," Phys. Chem. Chem. Phys., 2006, pp. 3486-3495, vol. 8.

Wang, L., "Multiscale photoacoustic microscopy and computed tomography," NIH Public Access Author Manuscript, Aug. 29, 2010, pp. 1-16, published in final edited form as Nat. Photonics, Aug. 29, 2009, pp. 503-509, vol. 3, No. 9.

Wang, Y. et al., "Fiber-laser-based photoacoustic microscopy and melanoma cell detection," J. Biomed. Opt., Jan. 2011, pp. 011014-1 to 011014-4, vol. 16, No. 1.

Wang, L. et al., "Photoacoustic Tomography: In Vivo Imaging from Organelles to Organs," Sci., Mar. 23, 2012, pp. 1458-1462, vol. 335.

Wang, Z. et al., "CD146, a multi-functional molecule beyond adhesion," Cancer Lett., 2013, pp. 150-162, vol. 330.

Wei, X. et al., "Selective Uptake of Indocyanine Green by Reticulocytes in Circulation," Invest. Ophthalmol. Vis. Sci., Oct. 2003, pp. 4489-4496, vol. 44, No. 10.

Weight, R. et al., "Photoacoustic detection of metastatic melanoma cells in the human circulatory system," Opt. Lett., Oct. 15, 2006, pp. 2998-3000, vol. 31, No. 20, Optical Society of America.

Wicha, M. et al., "Circulating Tumor Cells: Not All Detected Cells Are Bad and Not All Bad Cells Are Detected," J. Clin. Oncol., 2011, pp. 1508-1511, vol. 29.

Williams, S., "Circulating Tumor Cells," PNAS, Mar. 26, 2013, p. 4861, vol. 110, No. 13.

Witzig, T. et al., "Detection of Circulating Cytokeratin-positive Cells in the Blood of Breast Cancer Patients Using Immunomagnetic Enrichment and Digital Microscopy," Clin. Cancer Res., May 2002, pp. 1085-1091, vol. 8.

Xu, M. et al., "Photoacoustic imaging in biomedicine," Rev. Sci. Instrum., 2006, pp. 041101-1 to 041101-22, vol. 77.

Xu, X. et al., "Circulating Tumor Cells and Melanoma Progression," J. Invest. Dermatol., 2010, pp. 2349-2351, vol. 130.

Yang, J. et al., "Melanoma Proteoglycan Modifies Gene Expression to Stimulate Tumor Cell Motility, Growth, and Epithelial-to-Mesenchymal Transition," Cancer Res., 2009, pp. 7538-7547, vol. 69, No. 19.

Yu, M. et al., "Circulating tumor cells: approaches to isolation and characterization," J. Cell Biol., 2011, pp. 373-382, vol. 192, No. 3.

Yu, M. et al., "Circulating Breast Tumor Cells Exhibit Dynamic Changes in Epithelial and Mesenchymal Composition," Sci., Feb. 1, 2013, pp. 580-584, vol. 339.

Zharov, V. et al., "Photothermal detection of local thermal effects during selective nanophotothermolysis," Appl. Phys. Lett., Dec. 15, 2003, pp. 1-3, vol. 83, No. 24.

Zharov, V. et al., "Infrared imaging of subcutaneous veins," Lasers Surg. Med., Jan. 2004, pp. 56-61, vol. 34, No. 1, Wiley-Liss, Inc.

Zharov, V. et al., "Photothermal Imaging of Nanoparticles and Cells," IEEE Journal of Selected Topics in Quantum Electronics, Jul./Aug. 2005, pp. 733-751, vol. 11, No. 4.

Zharov, V. et al., "Microbubbles-overlapping mode for laser killing of cancer cells with absorbing nanoparticle clusters," J. Physics D: Appl. Phys., 2005, pp. 2571-2581, vol. 38.

Zharov, V. et al., "Photoacoustic tweezers with a pulsed laser source: theory and experiments," J. Physics D: Appl. Phys., 2005, pp. 1-13, vol. 38, IOP Publishing Ltd, United Kingdom.

Zharov, V. et al., "Photothermal image flow cytometry in vivo," Opt. Lett., Mar. 15, 2005, pp. 628-630, vol. 30, No. 6.

Zharov, V. et al., "In Vivo Photothermal Flow Cytometry: Imaging and Detection of Individual Cells in Blood and Lymph Flow," J. Cellular Biochem., 2006, pp. 916-932, vol. 97, No. 5.

Zharov, V. et al., "In vivo photoacoustic flow cytometry for monitoring of circulating single cancer cells and contrast agents," Opt. Lett., Dec. 15, 2006, pp. 3623-3625, vol. 31, No. 24.

Zharov, V. et al., "Photothermal Flow Cytometry in Vitro for Detection and Imaging of Individual Moving Cells," Cytometry Part A, 2007, pp. 191-206, vol. 71A.

Zharov, V. et al., "Confocal photothermal flow cytometry in vivo," Proc. SPIE, Apr. 2005, pp. 15-26, vol. 5697.

Zharov, V. et al., "Integrated photothermal flow cytometry in vivo," J. Biomed. Opt., Sep./Oct. 2005, pp. 051502-1-051502-13, vol. 10, No. 5.

Zharov, V. et al., "Nanocluster model of photothermal assay: application for high-sensitive monitoring of nicotine-induced changes in metabolism, apoptosis, and necrosis at a cellular level," J. Biomed. Opt., Jul./Aug. 2005, pp. 044011-1-044011-15, vol. 10, No. 4.

Zharov, V. et al., "Self-assembling nanoclusters in living systems: application for integrated photothermal hanodiagnostics and nanotherapy," J. Nanomed., Dec. 2005, pp. 326-345, vol. 1, No. 4.

Zharov, V. et al., "Synergistic enhancement of selective nanophotothermolysis with gold nanoclusters: Potential for cancer therapy," Laser Surg. Med., 2005, pp. 219-226, vol. 37, No. 3.

Aguirre-Ghiso, J., "On the theory of self-seeding: implications for metastasis progression in humans," Breast Cancer Res., 2010, pp. 1-2, vol. 12, No. 304.

Alexander, J., "The Normal Blood Clotting Time in the Light of Experience with the 'Two-syringe' Technique," J. Clin. Pathol., 1955, pp. 227-228, vol. 8.

Alix-Panabieres, C. et al., "Circulating Tumor Cells and Circulating Tumor DNA," Annu. Rev. Med., 2012, pp. 199-215, vol. 63.

Alix-Panabieres, C. et al., "Circulating Tumor Cells: Liquid Biopsy of Cancer," Clin. Chem., 2013, pp. 110-118, vol. 59, No. 1.

Allan, A. et al., "Detection and Quantification of Circulating Tumor Cells in Mouse Models of Human Breast Cancer Using Immunomagnetic Enrichment and Multiparameter Flow Cytometry," Cytometry Part A, May 2005, pp. 4-14, vol. 65A, No. 1, Wiley-Liss, Inc.

(56) References Cited

OTHER PUBLICATIONS

Alunni-Fabbroni, M. et al., "Circulating tumour cells in clinical practice: Methods of detection and possible characterization," Methods, 2010, pp. 289-297, vol. 50, Elsevier Inc.
Ara, G. et al., "Irradiation of Pigmented Melanoma Cells With High Intensity Pulsed Radiation Generates Acoustic Waves and Kills Cell," Lasers in Surgery and Medicine, 1990, pp. 52-59, vol. 10, No. 1.
Autebert, J. et al., "Microfluidic: an innovative tool for efficient cell sorting," Methods, 2012, pp. 297-307, vol. 57, No. 3, Elsevier.
Baeuerle, P. et al., "EpCAM (CD326) finding its own role in cancer," Br. J. Cancer, Feb. 12, 2007, pp. 417-423, vol. 96.
Beard, P., "Biomedical photoacoustic imaging," Interface Focus, 2011, pp. 602-631, vol. 1.
Berciaud, S. et al., "Photothermal Heterodyne Imaging of Individual Nonfluorescent Nanoclusters and Nanocrystals," Phys. Rev. Lett., Dec. 17, 2004, pp. 257402-1 to 257402-4, vol. 93.
Bhattacharyya, B. et al., "Gold nanoparticle-mediated detection of circulating cancer cells," NIH Public Access Author Manuscript, Mar. 1, 2013, pp. 1-18, published in final form as Clin. Lab. Med., Mar. 2012, pp. 89-101, vol. 32, No. 1.
Bhattacharyya, K. et al., "Detection, isolation, and capture of circulating breast cancer cells with photoacoustic low cytometry," Proc. SPIE, 2013, 9 pgs., vol. 8570A.
Biris, A. et al., "In vivo Raman flow cytometry for real-time detection of carbon nanotube kinetics in lymph, blood, and issues," J. Biomed. Opt., Mar./Apr. 2009, pp. 021006-1-021006-10, vol. 14, No. 2.
Birtill, D. et al., "Photoacoustic Spectroscopy," Central Laser Facility Annual Report, 2010-2011, Laser for Science Facility-Biology, 25 pgs.
Blab, G. et al., "Optical readout of gold nanoparticle-based DNA microarrays without silver enhancement," Biophys. J. Biophys. Lett., 2006, pp. L13-L15, vol. 90, No. 1.
Bland, J. et al., "Statistical methods for assessing agreement between two methods of clinical measurement," Lancet, Feb. 8, 1986, pp. 307-310, vol. 1.
Boutrus, S. et al., "Portable two-color in vivo flow cytometer for real-time detection of fluorescently-labeled circulating cells," NIH Public Access Author Manuscript, Dec. 28, 2009, pp. 1-8, published in final edited form as J. Biomed. Opt., 2007, p. 020507, vol. 12, No. 2.
Brusnichkin, A. et al., "Ultrasensitive label-free photothermal imaging, spectral identification, and quantification of cytochrome c in mitochondria, live cells, and solutions," NIH Public Access Author Manuscript, May 11, 2012, pp. 1-28, Published in final edited form as J. Biophotonics, Dec. 2010, pp. 791-806, vol. 3, No. 12.
Budd, G. et al., "Circulating Tumor Cells versus Imaging-Predicting Overall Survival in Metastatic Breast Cancer," Clin. Cancer Res., Nov. 1, 2006, pp. 6403-6409, vol. 12, No. 21.
Chaffer, C. et al., "A Perspective on Cancer Cell Metastasis," Sci., Mar. 25, 2011, pp. 1559-1564, vol. 25, No. 331.
Chen, Y. et al., "Platelet CD62P Expression and Microparticle in Murine Acquired Immune Deficiency Syndrome and Chronic Ethanol Consumption," Alcohol Alcoholism, Jan. 1, 2003, pp. 25-30, vol. 38, No. 1.
Chitnis, P. et al., "Feasibility of optoacoustic visualization of high-intensity focused ultrasound-induced thermal lesions in live tissue," J. Biomed. Opt., Mar./Apr. 2010, pp. 021313-1 to 021313-5, vol. 15, No. 2.
Chu, J. et al., "The Role of Cancer Stem Cells in the Organ Tropism of Breast Cancer Metastasis: A Mechanistic Balance between the "Seed" and the "Soil"?," Int. J. Breast Cancer, 2012, pp. 1-12, vol. 2012, Article ID 209748, Hindawi Publishing Corporation.
Cristofanilli, M. et al., "Circulating tumor cells, disease progression, and survival in metastatic breast cancer," N. Engl. J. Med., 2004, pp. 781-791, vol. 351.
Cristofanilli, M. et al., "Circulating Tumor Cells: A Novel Prognostic Factor for Newly Diagnosed Metastatic Breast Cancer," J. Clin. Oncol., Mar. 1, 2005, pp. 1420-1430, vol. 23, No. 7.

Debruyn, M. et al., "Melanoma-associated Chondroitin Sulfate Proteoglycan (MCSP)-targeted delivery of soluble TRAIL potently inhibits melanoma outgrowth in vitro and in vivo," Mol. Cancer, 2010, pp. 1-14, vol. 9, No. 301.
DeGiorgi, V. et al., "Application of a Filtration- and Isolation-by-Size Technique for the Detection of Circulating Tumor Cells in Cutaneous Melanoma," J. Invest. Dermatol., 2010, pp. 2440-2447, vol. 130.
De La Zerda, A. et al., "Advanced contrast nanoagents for photoacoustic molecular imaging, cytometry, blood test and photothermal theranostics," Contrast Media Mol. Imaging, 2011, pp. 346-369, vol. 6, John Wiley & Sons, Ltd.
Dick, J., "Breast cancer stem cells revealed," PNAS, Apr. 1, 2003, pp. 3547-3549, vol. 100, No. 7.
European Extended Search Report dated Aug. 10, 2018 from related European Patent Application No. 15876378.9; 13 pgs.
Freeman, J. et al., "Evaluation of a multi-marker immunomagnetic enrichment assay for the quantification of circulating melanoma cells," J. Transl. Med., 2012, pp. 1-9, vol. 10, No. 192.
Fukunaga-Kalabis, M. et al., "Beyond ABC: Another Mechanism of Drug Resistance in Melanoma Side Population," J. Invest. Dermatol., 2012, pp. 2317-2319, vol. 132.
Gaiduk, A. et al., "Room-Temperature Detection of a Single Molecule's Absorption by Photothermal Contrast," Sci., Oct. 15, 2010, pp. 353-356, vol. 330.
Galanzha, E. et al., "In vivo integrated flow image cytometry and lymph/blood vessels dynamic microscopy," J. Biomed. Opt., Sep./Oct. 2005, pp. 054018-1-054018-8, vol. 10, No. 5.
Galanzha, E. et al., "Advances in small animal mesentery models for in vivo flow cytometry, dynamic microscopy, and drug screening," World J. Gastroenterol., Jan. 14, 2007, pp. 192-218, vol. 13, No. 2, The WJG Press.
Galanzha, E. et al., "In vivo multispectral, multiparameter, photoacoustic lymph flow cytometry with natural cell focusing, label-free detection and multicolor nanoparticle probes," Cytometry A, 2008, pp. 884-894, vol. 73A, No. 10, with NIH Public Access Author Manuscript, Oct. 1, 2009, pp. 1-19.
Galanzha, E. et al., "In vivo, Noninvasive, Label-Free Detection and Eradication Of Circulating Metastatic Melanoma Cells Using Two-Color Photoacoustic Flow Cytometry with a Diode Laser," Cancer Res., 2009, pp. 7926-7934, vol. 69, No. 20.
Galanzha, E. et al., "In vivo fiber-based multicolor photoacoustic detection and photothermal purging of metastasis in sentinel lymph nodes targeted by nanoparticles," NIH Public Access Author Manuscript, May 24, 2013, pp. 1-17, published in final edited form as J. Biophoton., Sep. 2009, pp. 528-539, vol. 2.
Galanzha, E. et al., "Nanotechnology-based molecular photoacoustic and photothermal flow cytometry platform for In-vivo detection and killing of circulating cancer stem cells," J. Biophoton., 2009, pp. 725-735, vol. 2, No. 12.
Galanzha, E. et al., "In vivo magnetic enrichment and multiplex photoacoustic detection of circulating tumour cells," NIH Public Access Author Manuscript, May 24, 2013, pp. 1-13, published in final edited form as Nat. Nanotechnol., Dec. 2009, pp. 855-860, vol. 4, No. 12.
Galanzha, E. et al., "In Vivo Photoacoustic and Photothermal Cytometry for Monitoring Multiple Blood Rheology Parameters," Cytometry Part A, Oct. 2011, pp. 746-757, vol. 79, No. 10.
Galanzha, E. et al., "In Vivo Flow Cytometry of Circulating Clots Using Negative Photothermal and Photoacoustic Contrasts," Cytometry Part A, Oct. 2011, pp. 814-824, vol. 79A, No. 10, with Corrigendum, Cytometry Part A, 2011, pp. 1024, vol. 79A, No. 12.
Galanzha, E. et al., "Photoacoustic flow cytometry," Methods, Jul. 2012, pp. 280-296, vol. 57, No. 3, with HHS Public Access Author Manuscript, Mar. 19, 2016, pp. 1-44, Academic Press.
Galanzha, E. et al., "In vivo Magnetic Enrichment, Photoacoustic Diagnosis, and Photothermal Purging of Infected Blood Using Multifunctional Gold and Magnetic Nanoparticles," PLoS One, Sep. 2012, pp. 1-14, vol. 7, No. 9, e45557.
Galanzha, E. et al., "Circulating tumor cell detection and capturing using photoacoustic flow cytometry in vivo and ex vivo," Cancers, Manuscript, 2013, pp. 1-45, vol. 5.

(56) References Cited

OTHER PUBLICATIONS

Galanzha, E. et al., "Photoacoustic and photothermal cytometry using photoswitchable proteins and nanoparticles with ultrasharp resonances" J. Biophoton., Jan. 2015, pp. 81-93, vol. 8, No. 1-2, Wiley-VCH Verlag Gmbh & Co. KGaA, Weinheim.
Garrett, T. et al., "Bacterial adhesion and biofilms on surfaces," Progress in Natural Science, 2008, pp. 1049-1056, vol. 18, Elsevier.
Givan, A., "Flow Cytometry. An Introduction," Methods in Molecular Biology, Flow Cytometry Protocols, Second Edition, 2004, pp. 1-31, vol. 263, Humana Press.
Goddard, G. et al., "Ultrasonic Particle-Concentration for Sheathless Focusing of Particles for Analysis in a Flow Cytometer," Cytometry Part A, 2006, pp. 66-74, vol. 69A.
Zharov, V. et al., "In vivo high-speed imaging of individual cells in fast blood flow," J. Biomed. Opt., Sep./Oct. 2006, pp. 054034-1-054034-4, vol. 11, No. 5.
Zharov, V. et al., "Photothermal Nanotherapeutics and Nanodiagnostics for Selective Killing of Bacteria Targeted with Gold Nanoparticles," Biophys. J., Jan. 2006, pp. 619-627, vol. 90, Biophysical Society.
Zharov, V. et al., "Photoacoustic flow cytometry: principle and application for real-time detection of circulating nanoparticles, pathogens, and contrast dyes in vivo," J. Biomed. Opt., Sep. 1, 2007, pp. 051503-1-051503-14, vol. 12, No. 5.
Zharov, V. et al., "Ultrasharp nonlinear photothermal and photoacoustic resonances and holes beyond the spectral imit," HHS Public Access Author Manuscript, Jan. 2, 2015, pp. 1-16, published in final edited form as Nat. Photonics, Feb. 2011, pp. 110-116, vol. 5, No. 2.
Zhe, X. et al., "Circulating tumor cells: finding the needle in the haystack," Am. J. Cancer Res., 2011, pp. 740-751, vol. 1, No. 6.
Zheng, H. et al., "Detection of the Cancer Marker CD146 Expression in Melanoma Cells with Semiconductor Quantum Dot Label," J. Biomed. Nanotechnol., Aug. 2010, pp. 303-311, vol. 6, No. 4.
Gutierrez-Juarez, G. et al., "Optical Photoacoustic Detection of Circulating Melanoma Cells In Vitro," Int. J. Thermophys., 2010, pp. 784-792, vol. 31, Springer Science+Business Media, LLC.
Gutierrez-Juarez, G. et al., "Detection of Melanoma Cells In Vitro Using an Optical Detector of Photoacoustic Waves," Lasers Surg. Med., 2010, pp. 274-281, vol. 42.
Haruna, M. et al., "Blood Volume Measurement at the Bedside Using ICG Pulse Spectrophotometry," Anesthesiology, 1998, pp. 1322-1328, vol. 89.
Ida, J. et al., "Cell surface chondroitin sulfate glycosaminoglycan in melanoma: role in the activation of pro-MMP-2 (progelatinase A)," Biochem. J., May 1, 2007, pp. 553-563, vol. 403, No. 3, Biochemical Society, Great Britain.
International Search Report and Written Opinion dated Dec. 16, 2013 from related International Patent Application No. PCT/US2013/061673; 8 pgs.
International Search Report and Written Opinion dated Mar. 17, 2016 from related International Patent Application No. PCT/US2015/068341; 8 pgs.
International Search Report and Written Opinion dated Oct. 6, 2016 from related International Patent Application No. PCT/US2016/035512; 12 pgs.
Ion, R-M. et al., "The incorporation of various porphyrins into blood cells measured via flow cytometry, absorption and emission spectroscopy," Acta Biochim. Pol., 1998, pp. 833-845, vol. 45, No. 3.
Joosse, S. et al., "Biologic Challenges in the Detection of Circulating Tumor Cells," Cancer Res., Jan. 1, 2013, pp. 8-11, vol. 73, No. 1.
Karpiouk, A. et al., "Combined Ultrasound and Photoacoustic Imaging to Age Deep Vein Thrombosis: Preliminary Studies," IEEE Ultrasonics Symposium, 2005, pp. 399-402, vol. 1.
Karpiouk, A. et al., "Combined ultrasound and photoacoustic imaging to detect and stage deep vein thrombosis: phantom and ex vivo studies," J. Biomed. Opt., Sep./Oct. 2008, pp. 054061-1 to 054061-8, vol. 13, No. 5.
Kaiser, J., "Cancer's Circulation Problem," Sci., Feb. 26, 2010, pp. 1072-1074, vol. 327.

Khlebtsov, B. et al., "Optical amplification of photothermal therapy with gold nanoparticles and nanoclusters," Nanotechnol., 2006, pp. 5167-5179, vol. 17, Institute of Physics Publishing.
Khoja, L. et al., "Biomarker utility of circulating tumor cells in metastatic cutaneous melanoma," J. Invest. Dermatol., Jun. 2013, pp. 1582-1590, vol. 133, No. 6.
Kim, Y. et al., "Subtyping Lymphocytes in Peripheral Blood by Immunoperoxidase Labeling and Light Scatter/Absorption Flow Cytometry," Clin. Chem., 1985, pp. 1481-1486, vol. 31, No. 9.
Kim, J-W. et al., "In situ fluorescence microscopy visualization and characterization of nanometer-scale carbon nanotubes labeled with 1-pyrenebutanoic acid, succinimdyl ester," Appl. Phys. Lett., 2006, pp. 213110-1 to 213110-3, vol. 88.
Kim, M. et al., "Tumor Self-Seeding by Circulating Cancer Cells," Cell, Dec. 24, 2009, pp. 1315-1326, vol. 139, Elsevier Inc.
Kim, J-W. et al., "Golden carbon nanotubes as multimodal photoacoustic and photothermal high-contrast molecular agents," NIH Public Access Author Manuscript, May 24, 2013, pp. 1-15, published in final edited form as Nat. Nanotechnol., Oct. 2009, pp. 688-694, vol. 4, No. 10.
Kim, C. et al., "Deeply penetrating in vivo photoacoustic imaging using a clinical ultrasound array system," Biomed. Opt. Express, Aug. 2010, pp. 278-284, vol. 1, No. 1.
Kim, J-W. et al., "Nanotheranostics of Circulating Tumor Cells, Infections and Other Pathological Factors In Vivo," NIH Public Access Author Manuscript, Mar. 4, 2014, pp. 1-37, published in final edited form as Mol. Pharm., Mar. 4, 2013, pp. 813-830, vol. 10, No. 3.
Krishnamurthy, S., "The Emerging Role of Circulating Tumor Cells in Breast Cancer," Cancer Cytopathol., Jun. 25, 2012, pp. 161-166, vol. 120.
Lai, C. et al., "CD133+ Melanoma Subpopulations Contribute to Perivascular Niche Morphogenesis and Tumorigenicity Through Vasculogenic Mimicry," Cancer Res., 2012, pp. 5111-5118, vol. 72, No. 19.
Langley, R. et al., "Tumor Cell-Organ Microenvironment Interactions in the Pathogenesis of Cancer Metastasis," Endocr. Rev., 2007, pp. 297-321, vol. 28, No. 3.
Lapotko, D. et al., "Photothermal image cytometry of human neutrophils," Cytometry, 1996, pp. 198-203, vol. 24, Wiley-Liss, Inc.
Lapotko, D. et al., "Spectral Evaluation of Laser-Induced Cell Damage With Photothermal Microscopy," Lasers in Surgery and Medicine, 2005, pp. 22-30, vol. 36, No. 1, Wiley-Liss, Inc.
Lasne, D. et al., "Label-free optical imaging of mitochondria in live cells," Opt. Exp., Oct. 17, 2007, pp. 14184-14193, vol. 15, No. 21.
Letfullin, R. et al., "Laser-induced explosion of gold nanoparticles: potential role for nanophotothermolysis of cancer," Nanomed., 2006, pp. 473-480, vol. 1, No. 4, Future Medicine Ltd.
Leung, C. et al., "Tumor Self-Seeding: Bidirectional Flow of Tumor Cells," Cell, Dec. 24, 2009, pp. 1226-1228, vol. 139, Elsevier Inc.
Li, C. et al., "Preparation and characterization of flexible nanoliposomes loaded with daptomycin, a novel antibiotic, for topical skin therapy," International Journal of Nanomedicine, Mar. 24, 2013, pp. 1285-1292, vol. 8.
Lianidou, E., "Circulating Tumor Cells—New Challenges Ahead," Clin. Chem., 2012, pp. 805-807, vol. 58, No. 5.
Liao, H. et al., "Gold Nanorod Bioconjugates," Chem. Mater., 2005, pp. 4636-4641, vol. 17, No. 18, American Chemical Society.
Liu, Z. et al., "Negative enrichment by immunomagnetic nanobeads for unbiased characterization of circulating tumor cells from peripheral blood of cancer patients," J. Transl. Med., 2011, pp. 1-8, vol. 9, No. 70.
Ma, J. et al., "Isolation of tumorigenic circulating melanoma cells," Biochem. Biophys. Res. Commun., 2010, pp. 711-717, vol. 402, No. 4, Elsevier Inc.
Maheswaran, S. et al., "Circulating Tumor Cells: a window into cancer biology and metastasis," HHMI Author Manuscript, pp. 1-6, Published as: Curr. Opin. Genet. Dev., Feb. 2010, pp. 96-99, vol. 20, No. 1.
Mallidi, S. et al., "Photoacoustic imaging in cancer detection, diagnosis, and treatment guidance," Trends Biotechnol., May 2011, pp. 213-221, vol. 29, No. 5.

(56) References Cited

OTHER PUBLICATIONS

Menyaev, Y. et al., "Resolution of photoacoustic flow cytometry," Optical Society of America, 2013, 16 pgs.

Menyaev, Y. et al., "Preclinical photoacoustic models: application for ultrasensitive single cell malaria diagnosis in large vein and artery," Biomed. Opt. Express, Sep. 1, 2016, pp. 3643-3658, vol. 7, No. 9.

Molino, A. et al., "A Comparative Analysis of Three Different Techniques for the Detection of Cancer Cells in Bone Marrow," Cancer, Feb. 15, 1991, pp. 1033-1036, vol. 67.

Nagrath, S. et al., "Isolation of rare circulating tumour cells in cancer patients by microchip technology," NIH Public Access Author Manuscript, May 10, 2011, pp. 1-11, published in final edited form as Nat., Dec. 20, 2007, pp. 1235-1239, vol. 450, No. 7173.

Nedosekin, D. et al., "Photothermal Multispectral Image Cytometry for Quantitative Histology of Nanoparticles and Micrometastasis in Intact, Stained and Selectively Burned Tissue," Cytometry Part A, 2010, pp. 1049-1058, vol. 77A.

Nedosekin, D. et al., "Ultra-fast photoacoustic flow cytometry with a 0.5 MHz pulse repetition rate nanosecond aser," Opt. Exp., 2010, pp. 8605-8620, vol. 18.

Nedosekin, D. et al., "In Vivo Ultra-Fast Photoacoustic Flow Cytometry of Circulating Human Melanoma Cells Using Near-Infrared High-Pulse Rate Lasers," Cytometry Part A, 2011, pp. 825-833, vol. 79A.

Nedosekin, D. et al., "In Vivo Plant Flow Cytometry: A First Proof-of-Concept," Cytometry Part A, 2011, pp. 855-865, vol. 79A.

Nedosekin, D. et al., "Photothermal Confocal Spectromicroscopy of Multiple Cellular Chromophores and Fluorophores," Biophys. J., Feb. 2012, pp. 672-681, vol. 102.

Nedosekin, D. et al., "Synergy of photoacoustic and fluorescence flow cytometry of circulating cells with negative and positive contrasts," J. Biophotonics, 2013, pp. 425-434, vol. 6, No. 5, Wiley-VCH Verlag GmbH & Co. KGaA, Weinheim, Germany.

Nedosekin, D. et al., "Photoacoustic and photothermal detection of circulating tumor cells, bacteria and nanoparticles in cerebrospinal fluid in vivo and ex vivo," J. Biophotonics, 2013, pp. 523-533, vol. 6, No. 6-7, Wiley-VCH Verlag GmbH & Co. KGaA, Weinheim, Germany.

Nedosekin, D. et al., "Photoacoustic-fluorescence in vitro flow cytometry for quantification of absorption, scattering and fluorescence properties of the cells," Proc. SPIE, 2013, pp. 858141-1 to 858141-6, vol. 8581.

Neeves, K. et al., "Catch Me If You Can: Isolating Circulating Tumor Cells from Flowing Blood," Clin. Chem., 2012, pp. 803-804, vol. 58, No. 5.

Nguyen, D. et al., "Metastasis: from dissemination to organ-specific colonization," Nat. Rev. Cancer, Apr. 2009, pp. 274-284, vol. 9, Macmillan Publishers Limited.

Novak, J. et al., "In vivo flow cytometer for real-time detection and quantification of circulating cells," NIH Public Access Author Manuscript, Jan. 4, 2010, pp. 1-8, published in final edited form as Opt. Lett., Jan. 1, 2004, pp. 77-79, vol. 29, No. 1.

Notice of Allowance dated May 19, 2015 from related U.S. Appl. No. 12/945,576; 11 pgs.

Notice of Allowance dated Jun. 28, 2016 from related U.S. Appl. No. 13/253,767; 9 pgs.

Notice of Allowance dated Aug. 14, 2015 from related U.S. Appl. No. 13/661,551; 9 pgs.

Notice of Allowance dated Feb. 26, 2019 from related U.S. Appl. No. 14/754,034; 7 pgs.

Notice of Allowance dated Nov. 6, 2020 from related U.S. Appl. No. 15/541,264; 8 pgs.

Notice of Allowance dated Jun. 28, 2021 from related U.S. Appl. No. 15/240,712; 10 pgs.

Notice of Allowance dated Oct. 25, 2021 from related U.S. Appl. No. 14/939,039; 9 pgs.

O'brien, C et al., "Detection and Isolation of Circulating Melanoma Cells using Photoacoustic Flowmetry," J. Vis. Exp., Nov. 2011, pp. 1-5, vol. 57, e3559.

O'brien, C et al., "Capture of circulating tumor cells using photoacoustic flowmetry and two phase flow," J. Biomed. Opt., Jun. 2012, pp. 061221-1 to 061221-9, vol. 17, No. 6.

Office Action dated Nov. 30, 2011 from related U.S. Appl. No. 12/334,217; 12 pgs.

Office Action dated Apr. 26, 2012 from related U.S. Appl. No. 12/334,217; 10 pgs.

Office Action dated Oct. 6, 2014 from related U.S. Appl. No. 13/253,767; 18 pgs.

Office Action dated Apr. 16, 2015 from related U.S. Appl. No. 13/253,767; 17 pgs.

Office Action dated Jul. 30, 2015 from related U.S. Appl. No. 13/253,767; 16 pgs.

Office Action dated Feb. 22, 2016 from related U.S. Appl. No. 13/253,767; 7 pgs.

Office Action dated Feb. 13, 2014 from related U.S. Appl. No. 13/661,551; 11 pgs.

Office Action dated Oct. 7, 2014 from related U.S. Appl. No. 13/661,551; 10 pgs.

Office Action dated Apr. 3, 2015 from related U.S. Appl. No. 13/661,551; 11 pgs.

Office Action dated Jan. 30, 2017 from related U.S. Appl. No. 14/552,143; 14 pgs.

Office Action dated Oct. 26, 2016 from related U.S. Appl. No. 14/668,418; 11 pgs.

Office Action dated May 24, 2017 from related U.S. Appl. No. 14/668,418; 12 pgs.

Office Action dated Nov. 27, 2017 from related U.S. Appl. No. 14/728,849; 9 pgs.

Office Action dated Dec. 8, 2017 from related U.S. Appl. No. 14/668,418; 29 pgs.

Office Action dated Dec. 14, 2017 from related U.S. Appl. No. 14/552,143; 9 pgs.

Office Action dated Jul. 13, 2018 from related U.S. Appl. No. 14/728,849; 12 pgs.

Office Action dated Jul. 13, 2018 from related U.S. Appl. No. 14/552,143; 9 pgs.

Office Action dated Aug. 10, 2018 from related U.S. Appl. No. 14/668,418; 16 pgs.

Office Action dated Sep. 26, 2018 from related U.S. Appl. No. 14/754,034; 7 pgs.

Office Action dated Nov. 29, 2018 from related U.S. Appl. No. 14/939,039; 8 pgs.

Office Action dated Feb. 8, 2019 from related U.S. Appl. No. 15/240,712; 37 pgs.

Office Action dated Mar. 22, 2019 from related U.S. Appl. No. 14/939,039; 6 pgs.

Office Action dated Aug. 22, 2019 from related U.S. Appl. No. 15/240,712; 13 pgs.

Office Action dated Oct. 11, 2019 from related U.S. Appl. No. 14/939,039; 9 pgs.

Office Action dated Apr. 3, 2020 from related U.S. Appl. No. 14/939,039; 10 pgs.

Office Action dated Jun. 25, 2020 from related U.S. Appl. No. 15/240,712; 18 pgs.

Office Action dated Dec. 16, 2020 from related U.S. Appl. No. 14/939,039; 9 pgs.

Office Action dated Jan. 21, 2021 from related U.S. Appl. No. 15/240,712; pgs.

Office Action dated Apr. 2, 2021 from related U.S. Appl. No. 14/939,039; 10 pgs.

Ozkumur, E. et al., "Inertial Focusing for Tumor Antigen-Dependent and -Independent Sorting of Rare Circulating Tumor Cells," NIH Public Access Author Manuscript, Oct. 3, 2013, pp. 1-20, published in final edited form as Sci. Transl. Med., Apr. 3, 2013, pp. 179ra47, vol. 5, No. 179.

Pantel, K. et al., "Detection, clinical relevance and specific biological properties of disseminating tumour cells,"Nat. Rev. Cancer, May 2008, pp. 329-340, vol. 8, Nature Publishing Group.

(56) References Cited

OTHER PUBLICATIONS

Pelan-Mattocks, L. et al., "Flow cytometric analysis of intracellular complexity and CD45 expression for use in rapid differentiation of leukocytes in bovine blood samples," Am. J. Vet Res., Nov. 2001, pp. 1740-1744, vol. 62, No. 11.

Perez-Gutierrez, F. et al., "Plasma Membrane Integrity and Survival of Melanoma Cells After Nanosecond Laser Pulses," Ann. Biomed. Eng., Nov. 2010, pp. 3521-3531, vol. 38, No. 11.

Piyasena, M. et al., "Multinode acoustic focusing for parallel flow cytometry," NIH Public Access Author Manuscript, Feb. 21, 2013, pp. 1-18, published in final edited form as Anal. Chem., Feb. 21, 2012, pp. 1831-1839, vol. 84, No. 4.

Prahl, S., "Optical Absorption of Hemoglobin," available at http://omlc.ogi.edu/spectra/hemoglobin, Dec. 15, 1999, 4 pgs.

Proskurnin, M. et al., "In Vivo Multispectral Photoacoustic and Photothermal Flow Cytometry with Multicolor Dyes: A Potential for Real-Time Assessment of Circulation, Dye-Cell Interaction, and Blood Volume," Cytometry Part A, 2011, pp. 834-847, vol. 79A.

Rai, R. et al., "Nanoparticles and their potential application as antimicrobials," Formatex Microbiology Series No. 3, Dec. 31, 2011, pp. 197-209, vol. 1.

Rao, C. et al., "Circulating melanoma cells and survival in metastatic melanoma," Int. J. Oncol., 2011, pp. 755-760, vol. 38.

Reggiori, G. et al., "Early alterations of red blood cell rheology in critically ill patients," Crit. Care Med., 2009, pp. 3041-3046, vol. 37, No. 12.

Riethdorf, S. et al., "Detection of Circulating Tumor Cells in Peripheral Blood of Patients with Metastatic Breast Cancer: A Validation Study of the CellSearch System," Clin. Cancer Res., Feb. 1, 2007, pp. 920-928, vol. 13, No. 3.

Sarimollaoglu, M. et al., "In vivo photoacoustic time-of-flight velocity measurement of single cells and hanoparticles," NIH Public Access Author Manuscript, Oct. 15, 2012, pp. 1-8, published in final edited form as: Opt. Lett., Oct. 15, 2011, pp. 4086-4088, vol. 36, No. 20.

Notice of Allowance dated Mar. 29, 2023 from related U.S. Appl. No. 17/668,909, 10 pages.

Non-Final Office Action for U.S. Appl. No. 18/105,636, issued Dec. 26, 2023 (81 Pages).

Final Office Action for U.S. Appl. No. 18/105,636 dated Jul. 8, 2024 (36 Pages).

Heitsch et al., "Multifunctional particles: Magnetic nanocrystals and gold nanorods coated with fluorescent dye-doped silica shells," Journal of Solid State Chemistry, 2008, pages.

Non-Final Office Action for U.S. Appl. No. 14/728,849 issued on Jan. 11, 2019 (23 Pages).

Al-Hajj, M., et al., "Prospective identification of tumorigenic breast cancer cells," PNAS, Apr. 1, 2003, pp. 3983-3988, vol. 100, No. 7, with Correction, PNAS, May 27, 2003, pp. 6890-6891, vol. 100, No. 11.

Notice of Allowance for U.S. Appl. No. 18/215,635 issued on Mar. 27, 2024 (91 Pages).

DEVICE AND METHOD FOR IN VIVO FLOW CYTOMETRY USING THE DETECTION OF PHOTOACOUSTIC WAVES

CROSS REFERENCE TO RELATED APPLICATIONS

This application is a continuation application of U.S. non-provisional application Ser. No. 14/939,039, filed Nov. 12, 2015 which is a continuation application of U.S. non-provisional application Ser. No. 13/661,551, entitled "Device and Method for In Vivo Flow Cytometry Using the Detection of Photoacoustic Waves" filed on Oct. 26, 2012, which is a divisional application of U.S. non-provisional application Ser. No. 12/334,217, entitled "Device and Method for In Vivo Flow Cytometry Using the Detection of Photoacoustic Waves" filed on Dec. 12, 2008, which claims priority from U.S. provisional patent application Ser. No. 61/013,543, entitled "Device and Method for In Vivo Flow Cytometry Using the Detection of Photoacoustic Waves" filed on Dec. 13, 2007, all of which are hereby incorporated by reference herein in their entirety.

GOVERNMENTAL RIGHTS IN THE INVENTION

This work was supported in part by the National Institutes of Health grant numbers R01EB000873 and R21EB0005123. The U.S. Government may have certain rights in this invention.

FIELD OF THE INVENTION

This application relates to a device and methods of using the device to non-invasively detect laser-induced photoacoustic waves emitted by target objects such as cells, pathogens, microparticles, and nanoparticles in vivo, which indicate the presence of target objects circulating in blood or lymphatic vessels. In particular, this application relates to pulsing circulating target objects with pulses in a broad spectral range from a pulsed laser source, inducing the objects to emit ultrasonic photoacoustic waves that are subsequently detected by an ultrasound transducer.

BACKGROUND OF THE INVENTION

Flow cytometry (FC) is a well-established diagnostic method that has revolutionized cell diagnostics. In this technique, the cells in extracted samples are hydrodynamically induced to flow in single file through an artificial nozzle in vitro. Within this artificial flow, individual cells are illuminated by laser light, and the laser-stimulated fluorescence from molecular probes bound to cell membrane receptors or light scattered by the cells themselves, is detected using photodetectors. Multi-color FC with advanced fluorescent probes is widely used in basic and clinical research, making possible the rapid analysis of large populations of cells, the detection of rare cancer cells, and the evaluation of cell viability and drug—cell interactions. Flow cytometry ordinarily requires invasive extraction of cells from the living organism, fluorescent cell labeling, and cell sorting procedures, which may lead to unpredictable artifacts such as cytotoxicity. Traditional flow cytometry techniques are not suitable for applications such as the early diagnosis, prevention, and treatment of metastasis, inflammations, sepsis, immunodeficiency disorders, strokes, or heart attacks. Like traditional blood tests, traditional flow cytometry analyzes relatively small volume blood samples. In these small volume samples, the detection of rare metastatic cells or other antigens is ineffective until the disease has progressed to a stage in which the rare antigens are numerous enough to be detected in small blood samples. The long-term monitoring of cells in their native biological environment is desired in order to process a larger volume of blood, enabling the detection of antigens at a much earlier stage in the progression of a disease.

Several in vivo flow cytometry techniques take advantage of the single file movement of blood cells through the majority of blood vessels during normal circulation. Generally, these in vivo flow cytometry techniques also utilize light emitted from fluorescent molecular probes to acquire information about the circulating cells, requiring that the cells must be labeled with fluorescent molecular probes.

The powerful fluorescent labeling used in most in vitro and in vivo FC is prone to photobleaching, blinking, or cytotoxicity. These technical shortcomings limit the extension of traditional FC techniques to the long-term monitoring of blood or lymph flow on humans in vivo. The fluorescent labeling of cells may seriously compromise cell function and physiology. Acridine orange and rhodamine 6G, traditional fluorescent dyes used to label leukocytes in FC, are mutagenic and carcinogenic, as well as possibly phototoxic. Fluorescent imaging of microvessels with conventional fluorescein isothiocyanate-dextran (FITC) dye leads to elevated interstitial pressure and altered plasma viscosity. Fluorescent dyes or tags used in FC may significantly distort the measured occurrence and elimination of cells in circulation, such as apoptotic or cancer cells. The numerous shortcomings associated with the use of fluorescent dyes and tags emphasize the need for alternative approaches for the application of in vivo flow cytometry techniques to clinical or experimental measurements.

Another in vivo flow cytometry technique under development utilizes the detection of light scattered from unlabelled cells to deduce information about cells in circulation. Although this technique overcomes the shortcomings associated with fluorescent labeling, only a limited subset of circulating cells are sensitive to light scattering, and there is extensive background noise due to scattered light from red blood cells, which make up the majority of cells in circulation. Further, intervening cells and tissue attenuate the scattered light from the circulating cells, thereby limiting this technique to cells circulating in vessels near the skin's surface.

A novel in vivo flow cytometry technique overcomes most of the challenges and limitations of the preceding in vivo flow cytometry methods by utilizing laser-induced photothermal (PT) effects to detect the presence of target cells in circulation. A target cell is first illuminated with a pulse of laser light in the visible or near-infrared (NIR) spectral ranges, followed by a second pulse of laser light. The target cell absorbs the energy of the initial laser pulse, inducing a local temperature rise that distorts the refractive properties of the volume immediately surrounding the target cell. The characteristics of the light from the second laser pulse, as detected by a photodetector arranged opposite to the laser light source, determine the presence of the target cells based on the distortion of the refracted and scattered light near the target cell. Although the PT flow cytometry technique may be used to detect unlabelled target cells, this technique requires the transmission of light through the vessel to the photodetector on the opposite side. Like all of the other techniques described above that utilize the detection of light to gather information about circulating cells this technique is limited to cells circulating in relatively thin tissues.

Regardless of the flow cytometry technique, light traveling through biological tissues is scattered by surrounding cells and tissues. As such, the effectiveness of all of the flow cytometry techniques described above has been limited to the measurement of cells in relatively superficial blood vessels, since light may travel for only a short distance through the cells and tissues surrounding these vessels before becoming too scattered to be detected. A need exists for an in vivo flow cytometry technique in which the detected properties associated with the circulating cells are not as readily scattered by surrounding cells and tissues. Such a technique could be used to detect the presence of target cells in deep vessels as well as superficial vessels.

One technique used for the study of stationary tissues is photoacoustic (PA) detection. In this detection technique, target cells within the tissue absorb a pulse of light from within the visible or NIR spectrum ranges from a laser. The rapid temperature change resulting from the NIR light absorption by the target cells induces a characteristic ultrasound PA wave, which travels freely through most biological tissues and is readily detected by an ultrasound transducer. This technique may be used for unlabelled tissues or tissues labeled with various PA contrast agents such as nanoparticles and dyes. However, due to the challenge of coordinating the timing and characteristics of the laser illumination, limited sensitivity of the detection of the PA waves, time-consuming signal-acquisition algorithms, and poor spatial resolution, applications of PA imaging methods have been limited to the visualization of large groups of stationary cells, making this technique inappropriate for the requirements of in vivo flow cytometry.

In vivo flow cytometry techniques to date are limited to the detection of circulating cells in blood vessels only, due to intrinsic limitations in sensitivity and resolution. The capability to monitor the trafficking of cells in the lymphatic system would be a valuable additional feature. For example, metastatic malignant cancer cells may spread by way of the lymphatic system, or may form peripheral malignancies in sentinel lymph nodes near the initial tumor. The ability to monitor cells circulating in the lymphatic system would add a much-needed diagnostic technique for use in the early diagnosis of a variety of diseases, and for the continuous monitoring of many diseases during treatment. In addition, the lymphatic system is a common staging area for most immunological phenomena. A need exists to monitor cells circulating in the lymphatic system.

A need exists for an in vivo flow cytometry technique that may be used in superficial or deep vessels, with high sensitivity to individual cells and high resolution to discriminate the relatively rare target cells from among the numerous surrounding cells. Such a technique will make possible the non-invasive monitoring of cells in blood vessels as well as lymph vessels. Further, a need exists for an in vivo flow cytometry technique that measures unlabeled cells, as well as cells labeled with non-toxic dyes or tags.

SUMMARY OF THE INVENTION

The present invention provides a device for detecting the presence of moving target objects such as blood cells within a circulatory vessel of a living organism at a distance of up to 15 cm away from the vessel. The device includes at least one tunable pulsed laser source that functioning at one or more wavelengths between about 10 Å and about 1 cm. The laser pulses emitted by the at least one tunable pulsed laser source may have a predetermined pulse width that ranges between about 0.1 µs and about 1000 ns. The laser pulses emitted by the at least one tunable pulsed laser source may repeat at a predetermined rate ranging between about 1 Hz and about 500,000 Hz, and energy fluence of each laser pulse may be at a level ranging between about 0.1 mJ/cm$^2$ and about 1000 J/cm$^2$.

The device of the present invention also includes at least one optical element that operates to direct a laser pulse from the tunable laser source to pass through the vessel in which the moving target objects are to be detected. The at least one optical element also focuses laser pulse passing through the vessel into a beam with an elliptically shaped cross-section. The elliptically shaped beam cross-section has a maximum dimension ranging between about 1 µm and about 150 µm.

The device of the present invention also includes at least one ultrasound transducer with a sample rate ranging between about 10 kHz and about 100 MHz to detect the PA signals emitted by the target objects.

The present invention further provides a method for detecting at least one type of moving target object within a circulatory vessel of a living organism. The method includes pulsing the target object moving through the vessel of the organism vessel with at least one pulse of laser energy and detecting at least one resulting photoacoustic pulse emitted by the target object. The method also includes analyzing at least one characteristic of the detected photoacoustic pulse to determine at least one characteristic of the detected target objects. The characteristics of the detected photoacoustic pulse and of the detected target objects are described in detail below.

The moving target objects may be detected in blood or lymphatic vessels as far as about 15 cm away from the device of the present invention. Potentially, the moving target objects may be detected anywhere within the living organism. In an embodiment, the laser energy pulse may be delivered at one or more wavelengths ranging between about 10 Å and about 1 cm, a pulse width ranging between about 0.1 µs and about 1000 ns, a pulse repeat rate ranging between about 1 Hz and about 500,000 Hz, and a pulse energy fluence ranging between about 0.1 mJ/cm$^2$ and about 1000 J/cm$^2$. The ultrasonic photoacoustic waves emitted by the target objects may be detected at a sample rate ranging between about 10 kHz and about 100 MHz.

The present invention further provides a method for the in vivo detection of a circulating, unlabelled metastatic melanoma cell. The method includes pulsing an area of an organism with at least one pulse of near-infrared (NIR) laser energy at a wavelength ranging between about 650 nm and about 950 nm and a laser fluence ranging between about 20 mJ/cm$^2$ and about 100 mJ/cm$^2$, and then detecting the resulting photoacoustic pulse emitted by the melanoma cell. The method also includes analyzing detected photoacoustic pulses to indicate the presence of the metastatic melanoma cells in circulation.

The present invention further includes a method of selectively destroying target objects circulating in a vessel of an organism in vivo. The method includes detecting the target objects circulating in the vessels, triggering a pulse of laser energy delivered at a wavelength and energy level sufficient to cause the destruction of the detected target object, and monitoring the frequency of detection of the target objects circulating through the vessel. When the frequency of detection of the target objects falls below a threshold level, the detection and destruction of target objects is terminated.

Additional objectives, advantages and novel features will be set forth in the description which follows or will become apparent to those skilled in the art upon examination of the drawings and the detailed description which follows.

BRIEF DESCRIPTION OF THE DRAWINGS

Corresponding reference characters indicate corresponding elements among the views of the drawings. The headings used in the figures should not be interpreted to limit the scope of the claims.

DETAILED DESCRIPTION

I. Overview

Figure 1:
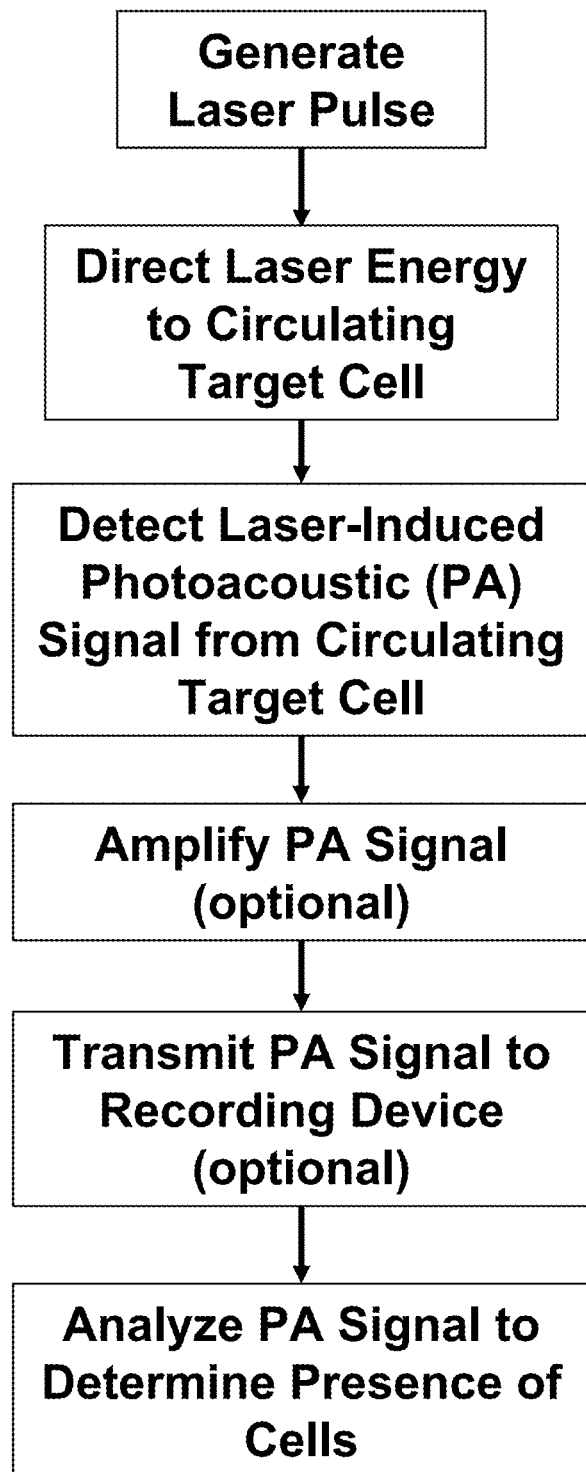
FIG. 1 is a flow chart of the photoacoustic in vivo flow cytometry method.
Figure 2:
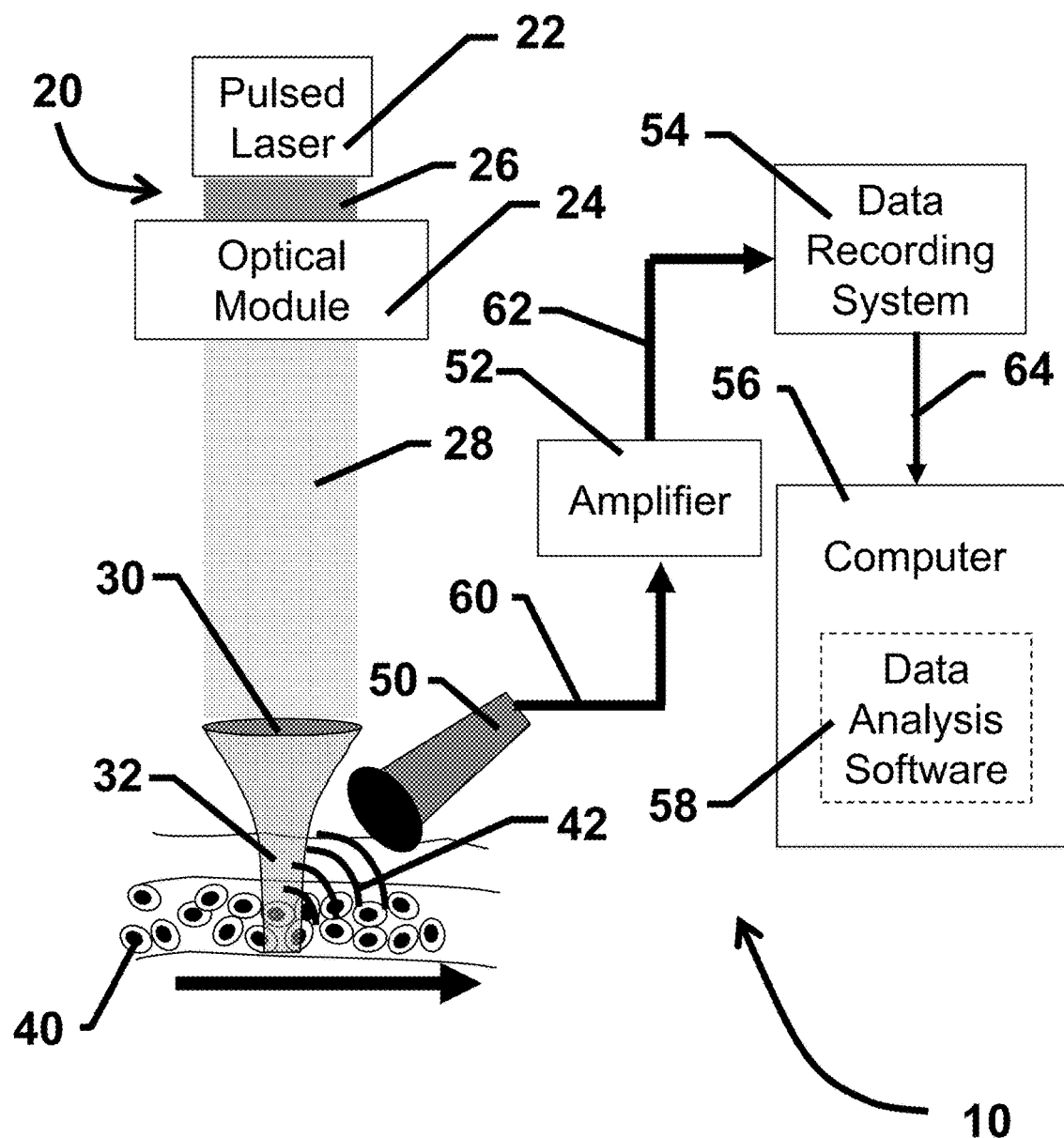
FIG. 2 is a diagram illustrating the in vivo flow cytometry device in accordance with an embodiment of the invention.
Figure 3A:
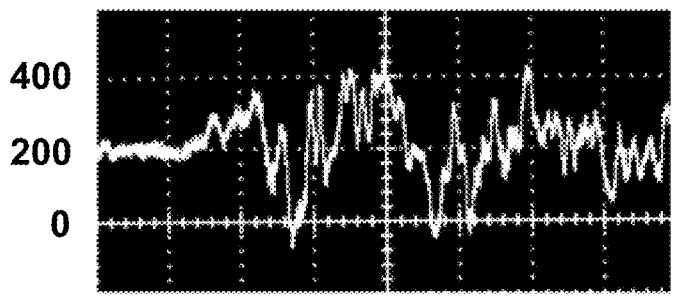
FIG. 3A shows the oscilloscope trace recordings of PA signals from blood flow in a rat ear vessel with diameter of 50 µm.
Figure 3B:
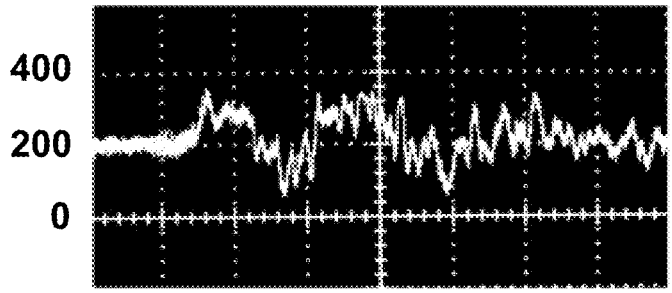
FIG. 3B shows the oscilloscope trace recordings of PA signals from skin surrounding a rat ear vessel before dye injection.
Figure 3C:
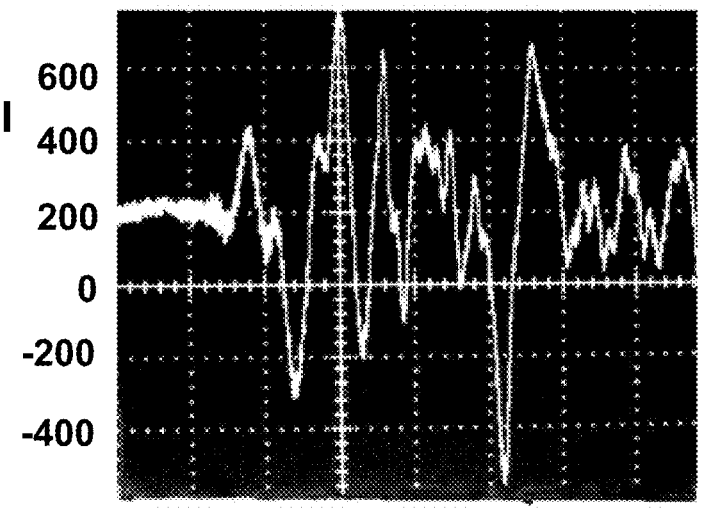
FIG. 3C shows the oscilloscope trace recordings of PA signals from blood flow in a rat ear vessel 5 min after the injection of Lymphazurin.
Figure 3D:
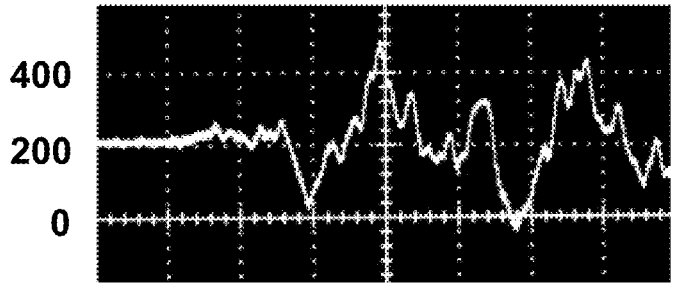
FIG. 3D shows the oscilloscope trace recordings of PA signals from the skin surrounding a rat ear vessel measured 20 min after dye injection.

The present invention is directed to a photoacoustic flow cytometry (PAFC) device 10, as shown in FIG. 2, used to perform non-invasive in vivo flow cytometry of at least one type of target object 40 circulating within the vessel of a living organism. The PAFC device 10 of the present invention includes a tunable wavelength pulsed laser 20 capable of emitting light energy ranging between wavelengths of about 400 nm and about 2500 nm. The tunable wavelength pulsed laser source 20 includes a pulsed laser 22, and may further include an optical module 26 to convert the wavelength, pulse rate, or both wavelength and pulse rate emitted by the pulsed laser 22 to desired values. In addition, the PAFC device 10 includes optical elements 30 such as lenses or optic fibers to direct the laser light to the target objects 40.

The PAFC device 10 also includes at least one ultrasound transducer 50 to detect photoacoustic waves 42 emitted by the target objects 40. The PAFC device 10 may optionally include an amplifier 52, a data recording system 54, and a computer 56 with stored data analysis software 58.

II. Principle of Operation

The PAFC device 10 is operated by illuminating a circulating target object 40 with laser energy pulses 32, thereby inducing the target objects 40, for example unlabeled blood cells, to emit a photoacoustic (PA) signal 42. The PA signal 42 is typically in the ultrasound spectrum, with a range of frequencies between about 20 kHz and about 200 MHz. The PA signal 42 emitted by the target objects 40 may result from the absorption of laser pulse 32 energy by a variety of mechanisms including, but not limited to single photon absorption, two photon absorption, multi-photon absorption, Coherent Anti-Stokes Raman Scattering (CARS), and combinations thereof.

The ultrasound transducer 50 detects the PA signal 42 emitted by the target object 40, and the output 60 from the ultrasound transducer 50 is analyzed using data processing software 58 to identify the presence of the target objects 40. In an embodiment, an amplifier 52 may amplify the output 60 of the ultrasound transducer 50. In an embodiment, the amplified signal 64 may be stored in a data recording system 54. In an embodiment, the computer 56 may access the stored signal data 64 for analysis using the data analysis software 58.

Because the ultrasound waves of the PA signals travel freely through most biological tissues, the PAFC device 10 may be used to detect circulating target objects 40 in circulatory and lymphatic vessels as deep as 15 cm below the external surface of the organism. Further, because the laser power used by the PAFC device 10 is relatively low due to the efficient absorption of laser light by target objects 40, in vivo PAFC may be conducted for extended time periods with minimal damage to any circulating cells. The PAFC may be used for the continuous monitoring of circulating cells for the early diagnosis and treatment of metastasis, inflammations, sepsis, immunodeficiency disorders, strokes, or heart attacks.

III. Target Objects

The method of the present invention may be used to detect target objects 40 circulating in vessels, defined herein as circulatory and lymphatic vessels at a depth between about 10 µm and about 15 cm below the surface of the skin and may include capillaries, arterioles, venules, arteries, veins, lymphatic vessels, hyphae, phloem, xylem, and sinuses. The diameters of the vessels may range between about 10 µm and about 2 cm. The vessels may be located in many different organs and tissues, including, but not limited to skin, lips, eyelid, interdigital membrane, retina, ear, nail pad, scrotum, lymph nodes, brain, breast, prostate, lung, colon, spleen, liver, kidney, pancreas, heart, testicles, ovaries, lungs, uterus, skeletal muscle, smooth muscle, and bladder.

In an embodiment, the at least one laser pulse 32 may be directed to a single location along one vessel, to two or more locations along a single vessel simultaneously, to two or more locations along a single vessel at two or more times, or simultaneously to locations on two or more vessels.

The method of the present invention may be used on organisms that possess cells circulating in vessels or sinuses, from the group of organisms including mammals, reptiles, birds, amphibians, fish, plants, fungi, mollusks, insects, arachnids, annelids, arthropods, roundworms, and flatworms.

The target objects 40 detected by the method of the present invention may be at least one target object 40 including but not limited to unlabeled biological cells, biological cell products, unbound contrast agents, biological cells labeled using contrast agents, and any combination thereof. The target objects 40 can be unlabeled endogenous or exogenous biological cells or cell products including but not limited to normal, apoptotic and necrotic red blood cells and white blood cells; aggregated red blood cells or clots; infected cells; inflamed cells; stem cells; dendritic cells; platelets; metastatic cancer cells resulting from melanoma, leukemia, breast cancer, prostate cancer, ovarian cancer, and testicular cancer; bacteria; viruses; fungal cells; protozoa; microorganisms; pathogens; animal cells; plant cells; and leukocytes activated by various antigens during an inflammatory reaction and combinations thereof.

The target objects 40 that are unlabeled biological cells may possess intrinsic cell-specific markers from the group comprised of hemoglobin (Hb), HbH, $HbO_2$, metHb, HbCN, HbS, HbCO, HbChr, myoglobins, melanin, cytochromes, bilirubin, catalase, porphyrins, chlorophylls, flavins, carotenoids, phytochromes, psoralens and combinations thereof.

The target objects 40 may also be biological cell products, including but not limited to products resulting from cell metabolism or apoptosis, cytokines or chemokines associated with the response of immune system cells to infection, exotoxins and endotoxins produced during infections, specific gene markers of cancer cells such as tyrosinase mRNA, p97, MelanA/Mart1 produced by melanoma cells, PSA produced by prostate cancer, and cytokeratins produced by breast carcinoma.

The target objects 40 may also be contrast agents from the group comprised of indocyanine green dye, melanin, fluoroscein isothiocyanate (FITC) dye, Evans blue dye, Lymphazurin dye, trypan blue dye, methylene blue dye, propidium iodide, Annexin, Oregon Green, C3, Cy5, Cy7, Neutral Red dye, phenol red dye, AlexaFluor dye, Texas red dye, gold nanospheres, gold nanoshells, gold nanorods, gold cages, carbon nanoparticles, prefluorocarbon nanoparticles, carbon nanotubes, carbon nanohorns, magnetic nanoparticles, quantum dots, binary gold-carbon nanotube nanoparticles, multilayer nanoparticles, clustered nanoparticles, liposomes, liposomes loaded with contrast dyes, liposomes loaded with nanoparticles, micelles, micelles loaded with contrast dyes, micelles loaded with nanoparticles, microbubbles, microbubbles loaded with contrast dyes, microbubbles loaded with nanoparticles, dendrimers, aquasomes, lipopolyplexes, nanoemulsions, polymeric nanoparticles, and combinations thereof.

The multilayer nanoparticles used as contrast agents for the target objects 40 may include two or more layers of materials with optical, thermal, and acoustic properties that enhance the PA signals 42 emitted by the target objects 40. Non-limiting examples of the effects of the multilayered nanoparticles on the PA pulses 42 emitted by the target objects 40 labeled with the multilayered nanoparticles include enhancing absorption of the laser pulse energy, increasing thermal relaxation time, increasing acoustic relaxation time, increasing the coefficient of thermal expansion, decreasing the coefficient of thermal diffusion, decreasing the local speed of sound near the target object 40, decreasing the threshold of bubble formation of the target object 40 and combinations thereof.

The target objects 40 may also be labeled living cells from the list above, marked with molecular markers and tags comprised of contrast agents selected from the list above. The molecular markers or tags may be attached to the cells without modification, or the contrast agents may be functionalized for binding to the cells using molecules including but not limited to antibodies, proteins, folates, ligands for specific cell receptors, receptors, peptides, viramines, wheat germ agglutinin, and combinations thereof. The ligands may include but not limited to ligands specific to folate, epithelial cell adhesion molecule (Ep-CAM), Hep-2, PAR, CD44, epidermal growth factor receptor (EGFR), as well as receptors of cancer cells, stem cells receptors, protein A receptors of *Staphylococcus aureus*, chitin receptors of yeasts, ligands specific to blood or lymphatic cell endothelial markers, as well as polysaccharide and siderophore receptors of bacteria.

Exogenous target objects 40 such as unbound contrast agents and exogenous unlabeled biological cells may be introduced into the circulatory or lymphatic vessels of the organism perenterally, orally, intradermally, subcutaneously, or by intravenous or intraperitoneal administration.

The target objects 40 may be concentrated near the desired area of detection using a variety of techniques. For target objects 40 possessing a larger diameter than the surrounding cells, the lumen of the vessel in which the target cells 40 are to be detected may be reduced in cross-sectional area using gentle mechanical pressure on the tissue surrounding the vessel, thereby retaining the larger diameter target cells 40, while allowing the surrounding cells with smaller diameter than the target objects 40 to flow away unimpeded from the desired area of detection. Alternatively, the target objects 40, regardless of object diameter, may be marked with magnetically active tags or markers, and the target objects 40 may be held in place by the magnetic forces exerted by a magnet with a magnetic field strength of at least seven Tesla, placed near the desired area of detection.

To further increase the contrast between PA signals 42 or originating from the target objects 40 and the background PA signals from surrounding cells and tissues, a variety of approaches may be used. The organism may be exposed to hyperoxic or hypoxic atmospheric conditions to induce different levels of oxygenation, which in turn alters the light absorption properties of the red blood cells. The osmolarity of the vessel flow may be altered by injecting hypertonic or hypotonic solutions into the desired vessel, thereby causing physical swelling or shrinking of surrounding cells, and further altering the light absorption characteristics of the surrounding cells. The hematocrit of the vessel flow may be altered by the injection of a diluting solution into the vessel flow, thereby reducing the density of surrounding cells in the vessel, and the resulting light absorption characteristics of the surrounding cells.

IV. Tunable Wavelength Pulsed Laser

The PAFC device 10 includes a tunable wavelength pulsed laser 20 which generates light energy at laser pulse widths ranging between about 0.1 μs and about 1000 ns, at least one wavelength ranging between about 400 nm and about 2500 nm, laser pulse rates ranging between about 1 Hz and about 500,000 Hz, and laser pulse energy fluences ranging between about 0.1 mJ/cm$^2$ and about 10 J/cm$^2$. A variety of tunable wavelength pulsed lasers 20 may be used to produce the laser pulse 28 so long as the laser energy is delivered in such a way that minimal damage occurs to any target objects 40 or surrounding cells or tissues that are illuminated by the device 10. The laser pulses of at least one wavelength may be delivered by a single tunable wavelength pulsed laser 20 or by an array of tunable wavelengths pulsed lasers 20, with each laser source 20 delivering laser pulses 28 of different wavelengths.

Several characteristics of the tunable wavelength pulsed laser 20 strongly influence the performance of the device 10, including the wavelength of light emitted by the laser (A), the diameter of the beam emitted by the laser, the duration of the light pulses emitted by the laser ($t_p$), the laser pulse repetition rate (f), and the laser fluence defined herein as the amount of energy emitted per square centimeter by the tunable wavelength pulsed laser 20.

A) Wavelength of Laser Pulse

The wavelengths of the laser pulses 32 may be selected to optimize the contrast of a single type of target object 40, or to optimize the contrast of two or more types of target objects 40. Typically, but not necessarily, to maximize the sensitivity and resolution of the PAFC device 10, the one or more wavelengths of laser pulses 32 should be optimized to enhance the contrast between the induced PA signals from the target objects 40 and the PA signals emitted by any surrounding cells. Thus, for target objects 40 that are unlabelled cells, the wavelength is selected in a range of the spectrum near the maximum absorbance of the unlabelled cells and as far as possible from the maximum absorbance of surrounding cells. If the target objects 40 are unbound contrast agents or cells that are labeled with contrast agents, the wavelength of the laser pulse 32 must fall within the range of wavelengths that are maximally absorbed by the contrast agents. As such, the present invention uses wavelengths of electromagnetic radiation emitted at wavelengths ranging between about 10 Å and about 1 cm. In an embodiment, the PAFC device 10 uses wavelengths of light emitted in the near-infrared spectrum ranging between about 400 nm and about 2500 nm.

In an embodiment, the PAFC device 10 may use diode lasers that generate laser pulses 32 with wavelengths ranging between about 640 nm and about 680 nm, between about 790 nm and about 830 nm, or between about 880 nm and about 930 nm. In an embodiment, the PAFC device 10 may use laser pulses or modulated continuous radiation in the x-ray spectrum (1-10 Å), the terahertz spectra (20-1000 μm) or the microwave spectra (0.5 mm-3 cm).

B) Laser Beam Dimensions

The size and spacing of the target objects 40 typically, but not necessarily, determine the laser beam's 32 cross-sectional shape and dimensions of the laser beam 32. To distinguish closely spaced target objects 40 in circulation, the minimum laser beam 32 dimension should be no smaller than the diameter of the target objects 40. For the size range of potential target objects 40 such as unbound nanoparticles, bacteria, blood cells, or metastatic cells, the minimum laser beam 32 dimension ranges between about 1 μm and about 20 μm.

The laser beams 32 may have a circular cross-section, with diameters comparable to the blood or lymph vessel diameters, for detecting rare target objects 40 that may be target cells separated by distances of at least 100 μm in circulation. For the detection of many closely-spaced target objects 40 in larger vessels, the laser beam 32 may be adjusted using known optical methods to an elliptical cross-sectional shape, with the long axis of the ellipse set to be the diameter of the larger vessel, and the short axis of the ellipse set to be the diameter of the cell. Thus, the laser beam 32 dimensions may range between about 1 μm and about 150 μm, in either a circular or an elliptical cross-sectional shape, depending on the relative rarity of the target objects 40, the dimensions of the target objects 40, and the diameter of the vessel in which the target objects 40 are detected.

Although any device which supplies light energy with the above characteristics may be used, the tunable wavelength pulsed laser 20 may include but is not limited to a pulsed or modulated continuous laser 22 optically connected to an optical module 32. The laser source 22 may include but is not limited to gas lasers, chemical lasers, excimer lasers, solid state lasers, fiber-hosted lasers, semiconductor (diode) lasers, dye lasers, and free electron lasers. The optical module 32 converts the wavelength of light emitted by the pulsed laser 26 to at least one different wavelength used for in vivo PAFC of the target objects 40 as specified above, typically within the visible and NIR spectral ranges. The optical module 32 can be any device capable of converting the laser wavelength or pulse rate to the desired wavelength or pulse rate using linear or non-linear optical effects, including but not limited to optical parametric oscillators, optical crystals, etalons, monochromatic filters, distributed Bragg reflector structures, Lyot filters, Raman shifters, or combinations thereof.

C) Laser Pulse Duration

Typically, but not necessarily, to generate the maximum PA signal 42 with optimal conversion of light energy into acoustic energy, the laser pulse 32 duration $t_P$ is predetermined to fall below a predetermined acoustic confinement criteria in order to minimize the mechanical stresses acting on the target object 40. This criterion may be expressed in equation form:

$$t_P \leq \tau_A = 2R/c_s \quad \text{Eqn. (1)}$$

where $\tau_A$ is the transit time of the acoustic wave traveling through the target object 40, R is the radius of the target object 40, and $c_s$ is the speed of sound inside the target object 40. Assuming a target object 40 diameter ranging between about 0.5 μm and about 15 μm for typical cells such as bacteria, blood, and metastatic cells, and assuming that the speed of sound inside the target objects 40 is approximately the same as the speed of sound in water ($1.5\times10^5$ cm/sec), then the range of the pulse durations required for detecting most potential target objects 40 ranges between about 0.7 ns and about 20 ns. Smaller bacterial cells may use pulse durations near the lower end of the range specified above, and larger metastatic cells may use pulse durations near the upper end of this range. Extremely small target objects 40 such as individual nanoparticles may require pulse durations of about $10^{-4}$ ns. The device 10 typically uses a pulse duration ranging between about 1 ns and about 20 ns, depending on the size of target objects 40.

D) Laser Pulse Repetition Rate

To accurately identify and discriminate between numerous circulating target objects 40 in relatively fast flow conditions, the pulsed laser 22 must typically, but not necessarily, have a pulse repetition rate that is sufficiently rapid to ensure that only one target object 40 is illuminated per pulse. In equation form, the laser pulse repetition rate (f) must fulfill the following predetermined criterion:

$$f \geq (V_F)/D \quad \text{Eqn. (2)}$$

where ($V_F$) is the flow velocity, and D is the diameter of the target object 40. In small mammal blood microvessels, flow velocities typically range from 1 mm/sec (capillary) to 10 mm/sec (arterioles). For a cell diameter of 20 μm, the pulse repetition rate may range between about 50 Hz and about 500 Hz. To detect smaller target objects 40, or target objects 40 in faster flowing vessels, the pulse repetition rate should be near higher end of this range. A high laser pulse repetition rate may also enhance the sensitivity of the device 10 during multi-pulse laser exposures because signal-to-noise ratio, which limits the sensitivity of the device 10, is proportional to the square root of the number of laser pulses. In an embodiment, the PAFC device 10 of the present invention uses a pulse repetition rate ranging between about 1 Hz and about 500,000 Hz.

In addition, when the one or more target objects 40 are illuminated by laser pulses of two or more different wavelengths, the time delay between the laser pulse 32 of one wavelength and the subsequent laser pulse 32 of a different wavelength should be sufficiently short so as to ensure that the two or more laser pulses illuminate the same target object 40. Further, the laser pulses 28 should have a time delay that further ensures that the second laser pulse 32 does not reach the target object 40 prior to detection of the PA signal 42 induced by the first laser pulse 32. For the range of distances at which the PAFC device 10 detects target objects 40, the time delay between laser pulses 32 ranges between about 0.1 μs and about 100 μs.

E) Laser Fluence

The laser fluence of the PAFC device 10, defined herein as the energy level of the laser pulse 32, should not exceed the ANSI safety standard, which depends on the laser's wavelength, and ranges between about 30 mJ/cm$^2$ and about 100 mJ/cm$^2$ in the NIR spectral region emitted by the laser 20 in an embodiment. In addition, the laser fluence should not exceed the thresholds at which significant cell photodamage may occur. The PAFC device 10 develops a laser fluence ranging between about 0.1 mJ/cm$^2$ and about 1000 J/cm$^2$, depending on factors such as the size and type of target objects 40, the depth of the vessel in which the target objects 40 are to be detected, and the density of the cells surrounding the vessel. When lower laser fluences are used, the resulting PA signals 42 are proportionally weaker in amplitude, and a more sensitive acoustic detection system 10 with signal acquisition properties that are optimized for the location and frequency of the PA signals 42 may be used to provide reliable detection of PA signals 42 from the target objects 40.

For PAFC measurements on vessels in deeper tissues, the laser pulses 32 may be delivered non-invasively at higher laser fluence from outside the organism. To avoid potential damage to any tissues located between the pulsed laser 20 and the target objects 40 resulting from higher energy laser pulses 32 or extended periods of PAFC measurement, the tissues may be cooled using methods broadly used in dermatological laser applications including but not limited to spray cooling, contact cooling, skin cooling with forced cooled air or liquid flow, an optically transparent cooling device attached to skin and cooled using circulating cooled water or electrical effects, and combinations thereof.

In an embodiment, laser pulses 32 may be delivered using a fiber optic cable placed in close vicinity of the target objects 40 using a minimally invasive needle delivery device. The laser pulses 32 may be delivered directly to the desired vessel using an optic fiber cable mounted in a catheter. The laser pulses 32 may be delivered by fiber-chip-based catheters inserted directly into the desired vessel. The target objects 40 may be detected by shunting circulating target objects 40 through artificial circulatory bypass tubes similar to those used in hemodialysis, that are transparent to laser light in the visible or NIR spectra, through a hemodialysis system, or through similar bioengineering devices known in the art.

V. Optics

Optics 30 are operatively connected to the output 28 of the tunable wavelength pulsed laser 20, and functions to deliver the laser pulses 32 to the target objects 40 or other desired area of illumination. The optics 30 are selected to deliver the laser pulses 32 to the target objects 40 with a beam dimension ranging between about 1 µm and about 40 µm, with a circular or elliptical cross-sectional geometry, as discussed above. The optics 30 may include but are not limited to conventional lenses, mirrors, optics fibers, and combinations thereof, so long as the shape and diameter of the beam may be controlled.

VI. Ultrasound Transducers

The ultrasound transducers 50 are pressure sensors that are placed in acoustical contact with the target objects 40 at a distance of up to 15 cm from the target objects 40. The ultrasound transducers 50 convert the laser-induced PA signals 42 received from the target objects 40 into voltage fluctuations that are subsequently amplified, digitized, stored, and/or analyzed. The ultrasonic transducers 50 are selected for their optimal sensitivity to the PA signals 42 emitted by the target objects 40. The ultrasonic transducers 50 typically have a sample rate ranging between about 10 kHz and about 100 MHz. Non-limiting examples of ultrasonic transducers so include, unfocused ultrasound transducers; focused ultrasound transducers with conventional and cylindrical focused lengths between about 2 mm and about 500 mm; and customized resonance ultrasound transducers. In an embodiment, the ultrasonic transducer 50 and pulsed laser 22 may have a confocal configuration, in which the transducer 50 may have a ring geometry with the pulsed laser 22 and associated optics 30 passing through the center of the ring of the transducer 50. In an embodiment, the PAFC device 10 may include one or more ultrasonic transducers 50.

The efficiency of acoustic matching of the ultrasound transducer 50 and the tissue of the organism may be enhanced by the application of an acoustically transparent liquid, such as glycerol, between the skin and the receiving surface of the ultrasound transducer 50. Any liquid may be placed between the skin and the receiving surface of the ultrasound transducer 50, so long as the liquid efficiently transmits ultrasound pressure waves. In addition, the acoustically transparent liquid should also transmit laser pulses in the visible and NIR spectra with minimal scattering of the laser pulse energy, if the liquid is located in the path of the laser pulse 32.

VII. Amplifier

An optional amplifier 52 may be electrically connected to the voltage output 60 of the ultrasonic transducer 50, should the PA signal 42 received from the target objects 40 prove to be too weak to analyze accurately. The amplifier 52 is selected for sensitivity and responsiveness to the PA signals 42 measured by the one or more ultrasonic transducers 50. The amplifier 52 is selected to possess a low frequency boundary between about 10 kHz and about 200 kHz, a high frequency boundary between about 1 MHz and about 100 MHz, and a resonance bandwidth between about 0.3 MHz and about 5 MHz. Any amplifier 52 can be used so long as it possesses the frequency response and resonance bandwidth described above.

VIII. Data Recording System

A data recording system 54 may be connected to the voltage output 60 of the ultrasonic transducer 50, or alternatively, the amplified output 62 of the ultrasonic transducer 50. Any digital or analog device capable of acquiring and storing incoming voltage data at frequencies as high as 50 MHz may be used. Non-limiting examples of the data recording system 54 include a boxcar averager device, a video camera recording the display of an oscilloscope electrically connected to receive the output of the ultrasonic transducer 50 or the amplifier 52, and combinations thereof. A boxcar averager device averages the output of several successive PA signals 42 to optimize the accuracy of the PAFC device 10. The oscilloscope display may be run at low speed to acquire the counts of many target objects 40 passing the PAFC device 10 in close succession, or the oscilloscope display may be run at high speed to discern detailed characteristics of the PA signal 42 such as wave magnitude or wave shape used to discriminate the target object 40 from surrounding cells. The data recording system 54 may include a still camera may be used to record the display an oscilloscope connected to the output of the ultrasonic transducer 50 or the amplifier 52.

IX. Data Analysis Software

The data analysis software 58 may access the stored data 64 from the data storage device 54, the voltage output 60 from the ultrasonic transducer 50, the voltage output 62 from the amplifier 52, or combinations thereof. The data analysis software 58 may also function as an amplifier 52, a data storage device 54, and combinations thereof. Any data analysis software 58 capable of processing data that fluctuates at frequencies ranging between about 20 Hz and 200 MHz may be used, including but not limited to user-written software, or commercially available analysis software. Non-limiting examples of commercially available analysis software includes Matlab (The MathWorks, Inc., USA), Mathematica (Wolfram Research, Inc., USA), Labview (National Instrument, USA), Avisoft (Avisoft Bioacoustics, Germany), and TomoView (Olympus NDT Inc., USA).

X. Combined Photoacoustic/Photothermal/Fluorescent Flow Cytometry Systems

The photoacoustic flow cytometry (PAFC) device 10 may include additional elements including, but not limited to photodetectors, additional lasers and optics, and additional analysis software associated with other in vivo flow cytometry methods that detect the target objects using the conventional and Raman scattering of the laser pulses by the target objects, photothermal effects induced by laser pulses on the target objects, and the fluorescence of the target objects induced by absorbed laser pulses. In an embodiment, the device 10 may be configured to simultaneously detect cells using photoacoustic methods, photothermal methods, light scattered by target objects, induced fluorescence of target objects, and any combination thereof.

XI. Method of In Vivo Flow Cytometry

The present invention further provides a method of in vivo flow cytometry using laser-excited photoacoustic pulses 42 emitted by at least one type of target object 40 circulating in the vessels of an organism. The method includes pulsing the target objects 40 moving through the vessels with at least one pulse of laser energy 32 at one or more wavelengths. As described above, the target objects 40 absorb the at least one pulse of laser energy 32 and emit at least one ultrasound photoacoustic pulse 42. The photoacoustic pulses 42 are detected by at least one ultrasound transducer 50, as described above. The photoacoustic pulses 42 are analyzed to determine at least one characteristic of the detected target objects 40. The characteristics of the detected target objects 40 may include, but are not limited to the type of target objects 40, the quantity of target objects 40, the concentration of target objects 40, the flow speed of the target objects 40, the total blood volume, and combinations thereof.

The flow speed of the target objects 40 may be based on analysis of the width of the PA signal 42 emitted by a target object 40, the time delay between two PA signals 42 measured at two locations separated by a known distance, or the frequency shift of a PA signal 42. The total circulating blood or lymph volume may be estimated using the degree of dilution of one or more absorbing dyes, or blood cells extracted from the organism, labeled using the marking compounds discussed above, and reintroduced into the vessels of the organism.

A) PA Signal Patterns

Signature PA signal patterns associated with each type of target object 40, include but are not limited to signal shape, frequency spectrum, amplitude, phase, and time delay between the one or more laser pulses 32 and the received PA signal 42. The PA signal patterns may be discriminated between PA signals 42 received from target objects 40 and background PA signals received from surrounding cells, blood and lymphatic vessel walls, and tissues. Further, the blood or lymph flow velocity may be determined using PA signal patterns including but not limited to the PA signal duration, the PA frequency shift, or the time delay between two PA signals 42 produced by a single target object 40 pulsed by two distinct laser pulses 32 applied at a known separation distance.

Different target object 40 types possess unique combinations of pigments and sub-cellular structures that absorb laser pulses 32 and emit PA signals 42 differently. Each type of target object 40 may be discriminated by its distinctive PA signature, as well as the particular wavelengths of laser pulses 32 used to elicit the PA signals 42 from target objects 40 without need for labeling. The contrast of the target objects 40 may be enhanced using contrast agents bound to the target objects 40 as described above.

The contrast of the PA signal patterns of the target objects 40 relative to surrounding cells and tissues are typically based on PA signal 42 amplitudes from the target objects 40 that are significantly higher than amplitudes of the PA signals 42 amplitudes from the surrounding cells and tissues. For example, aggregations of red blood cells in circulation may be detected using time-resolved monitoring of dynamic increases of PA signal amplitudes due to the higher local absorption of laser pulses 32 that result in higher amplitude PA signals 42 from the red blood cell aggregates relative to surrounding cells and tissues.

The PA signal amplitude emitted by target objects 40 may also be significantly lower than the PA signal 42 amplitudes from the surrounding cells and tissues. For example, circulating blood clots may be detected through the time-resolved monitoring of dynamic decreases of the PA signal amplitude, due to the attenuated PA signal amplitude emitted by blood clots relative to the PA signal amplitude emitted by red blood cells. The decreased PA signal amplitude emitted by blood clots is due to the lower light absorption of platelets (the dominant component of blood clots) relative to the light absorption of red blood cells (the dominant cell type overall in typical blood flows) in the visible and near-infrared spectral range. Whether the PA signal 42 of the target objects 40 is significantly higher or significantly lower than the PA signal 42 from surrounding cells and tissues, sufficient contrast must exist to accurately detect the PA signals of the target cells 40.

B) Detection of Target Objects in Lymph Vessels

For the detection of target objects 40 in the lymph vessels, target objects 40 are illuminated while passing between the leaves of a valve in a lymphatic vessel. The restricted flow through the valve of the lymphatic vessel facilitates the detection and identification of individual target objects 40. The phasic contractions of lymph vessels naturally concentrate the flow of target objects 40 near the center of the lymph vessel, and the lymph valves act as natural nozzles to provide the positioning of target objects 40 in single file with minimum radial fluctuation. To exclude detecting the same target objects 40 during their retrograde motion, as is typical in lymphatic vessels, the timing of the laser pulses 32 may be adjusted to synchronize with the phasic rhythms of the lymphatic flow. In addition, detection of forward moving target objects 40 may be achieved by synchronizing the laser pulses 32 with the motion of the lymphatic vessel wall or lymphatic valves that typically occurs during forward flow of lymph. The motion of the lymph vessel wall or lymphatic valves may be sensed using an additional pilot laser that produces signals that may be used to trigger the PAFC laser pulses 32.

The sensitivity of the detection of target objects 40 in lymph vessels maybe enhanced by creating a higher rate of lymph flow through the lymphatic valve by inducing the contraction of the upstream lymphangion, defined herein as the lymph vessel between two lymphatic valves. For example, the lymphangion may be induced to contract by exposure to a pulse of laser light 32 at a wavelength ranging between about 400 nm and about 950 nm, applied prior to the laser pulses 32 used to induce PA signals 42 from the target objects 40.

XII. Method of In Vivo Detection of Circulating Melanoma Cells

The present invention further provides a method for non-invasive detection of circulating unlabelled metastatic melanoma cells. The method includes pulsing at least one circulating metastatic melanoma cell with at least one pulse of NIR laser energy 32 at least one wavelength ranging between about 650 nm and about 950 nm and a laser fluence ranging between about 20 mJ/cm$^2$ and about 100 mJ/cm$^2$. The circulating unlabelled metastatic melanoma cells absorb the at least one laser pulse 32 and emit at least one ultrasound photoacoustic pulse 42, that is detected by at least one ultrasound transducer 50. The detected photoacoustic pulse 42 is analyzed to detect the presence of any metastatic melanoma cells in circulation.

Unlabelled metastatic melanoma cells in particular may be detected in the circulatory or lymphatic system of the organism using the method of the present invention. Without being bound to any particular theory, the large stores of melanin characteristic of melanoma cells readily absorb light at a wavelength of approximately 850 nm and emit strong photoacoustic ultrasound signals 42. Using the device 10 of the present invention with a tunable wavelength pulsed laser 20 with a pulse wavelength of about 850 nm, a laser fluence of about 35 mJ/cm$^2$, and a laser pulse duration of about 8 ns, circulating unlabelled metastatic melanoma cells may be detected with a resolution of at least 1 melanoma cell per $10^{10}$ cells.

XIII. Method for Selectively Destroying Circulating Cells In Vivo

The present invention provides a method of selectively destroying target objects 40 including but not limited to metastatic cancer cells using laser pulses 32 with a higher laser fluence than is typically used by the PAFC device 10. The method includes detecting the target objects 40 circulating in the vessels. The detection of a target object 40 triggers a pulse of laser energy 32 that is delivered to the detected target object 40 at a wavelength and fluence sufficient to cause the destruction of the detected target objects 40. The method may include monitoring the frequency of detection of target objects 40 circulating through the vessels, and terminating the method when the frequency of detection of the target objects 40 falls below a threshold level. The method of destroying target objects 40 may be terminated when the frequency of detection of target objects 40 falls below about $10^{-3}$ target objects/min and about $10^2$ target objects/min.

The target objects 40 may be detected using a method of in vivo flow cytometry using laser-excited photoacoustic waves 42 emitted by the target objects 40.

Because the absorption of target objects 40 are much higher than surrounding cells and tissue, the laser fluence may be increased beyond the level normally used for PAFC to levels that selectively damage the target objects 40 without harming the surrounding cells and tissues. Target objects 40 that are selectively destroyed using the method of the present invention include but are not limited to tumor cells, bacteria, viruses, clots, thromboses, plaques, and combinations thereof. This approach may be used for the selective destruction of target objects 40 circulating in blood vessels or lymph vessels. The PAFC methods of the present invention may be used to detect the target objects 40, trigger the high energy laser pulse 32 used to destroy the target objects 40, and detect the subsequent decrease in the target objects 40, thereby guiding the cell destruction at the single cell level.

EXAMPLES

The following examples illustrate the invention.

Example 1. In Vitro Photothermal (PT) Imaging was Used to Determine the Effect of Laser Energy Levels on Laser-Induced Cell Damage to Blood Cells and Subsequent Cell Viability To determine whether the laser pulses using in in vivo flow cytometry caused any significant damage to cells or tissues of the organism, the following experiment was conducted. The laser-induced damage threshold of single cells was evaluated as a function of the pumped-laser energy levels at a range of wavelengths using established methods (Zharov and Lapotko 2005, Lapotko and Zharov 2005). In vitro measurements of specific changes in photothermal (PT) images and PT responses from individual cells were used to determine cell damage. During the PT imaging, individual cells were illuminated with a pulse of laser light at a specified energy level and wavelength. After absorbing the energy of the laser pulse, the short-term temperature of the cell increased by as much as 5° C. The laser-induced temperature-dependent refractive heterogeneity in the vicinity of cells caused defocusing of a collinear He—Ne laser probe beam (model 117A; Spectra-Physics, Inc.; 633 nm, 1.4 mW) that illuminated the cell immediately after the initial laser pulse. This defocusing caused a subsequent reduction in the beam's intensity at its center, which was detected with a photodiode (C5658; Hamamatsu Corp.) through a 0.5-mm-diameter pinhole.

PT measurements were performed in vitro using mouse blood cells in suspension on conventional microscope slides. To simulate blood flow conditions, a flow module fitted with a syringe pump—driven system (KD Scientific, Inc.) was used with glass microtubes of different diameters in the range of 30 μm to 4 mm that provided flow velocities of 1-10 cm/sec, which were representative of the diameters and flow rates of animal microvessels.

Individual cells flowing through the glass microtubes were exposed to an 8 ns burst of laser light in a 20-μm circular or elongated beam at a variety of wavelengths ranging between 420 nm and 2300 nm. At each wavelength of the initial laser pulse, the laser fluence, defined as the energy contained in the laser beam, was varied between 0.1 mJ/cm$^2$ and 1000 J/cm$^2$. Damage to the cells was determined by assessing the changes in the PT imaging response of cells to laser pulses of increasing fluence. In addition, cell viability after exposure to laser energy was assessed using a conventional trypan blue exclusion assay. Cellular damage was quantified as ED50, the level of laser fluence at which 50% of the measured cells sustained photodamage in vitro. The ED50 values measured for rat red blood cells (RBC), white blood cells (WBC) and K562 blast cells using laser pulses in the visible light spectrum are summarized in Table 1. The ED50 values measured for rat red blood cells (RBC) and white blood cells (WBC) using laser pulses in the near-infrared (NIR) light spectrum are summarized in Table 2.

TABLE 1

Photodamage thresholds for single rat blood cells in the visible light spectrum.

| Wavelength of laser pulse (nm) | Photodamage threshold ED50 (J/cm$^2$) | | |
|---|---|---|---|
| | Rat RBC | Rat WBC | Rat K562 blast cell |
| 417 | 1.5 | 12 | 36 |
| 555 | 5 | 42 | 90 |

TABLE 2

Photodamage thresholds for single rat blood cells in near-IR spectral range.

| Wavelength of laser pulse (nm) | Photodamage threshold ED50 (J/cm$^2$) | |
|---|---|---|
| | Rat RBCs | Rat WBCs |
| 740 | 6.9 | 21.7 |
| 760 | 6.8 | |
| 780 | 17.7 | 152 |
| 800 | 17.5 | 219 |
| 820 | 28.0 | 251 |
| 840 | 43.5 | |
| 860 | 43.8 | 730 |
| 880 | 76.5 | |
| 900 | 69.4 | |
| 920 | 77.7 | 357 |
| 960 | 33.5 | 48.8 |

In the visible spectral range, the relatively strong light-absorbing RBCs sustained cell damage at much lower intensities of laser energy, resulting in ED50 values that were about an order of magnitude lower than the ED50 values measured for WBC or K562 blasts. In the NIR spectral range, where most cells, including RBC, have minimal absorption, cells did not sustain damage until much higher laser energy levels compared to the energy levels at which cellular damage occurred to cells exposed to laser energy in the visible spectrum. The damage thresholds (ED50) for RBCs and WBCs in the spectral range of 860-920 nm were more than one order magnitude higher compared to those in the visible spectrum as shown in Tables 1 and 2.

The results of this experiment established the levels of laser energy at which laser-induced cellular damage may occur. In the NIR spectrum, in which cells exhibited the strongest photoacoustic effects, the damage thresholds are several orders of magnitude above the maximum safety level of approximately 20-100 mJ/cm$^2$ set by ANSI safety standards. Thus, photoacoustic flow cytometry may be performed in vivo with little risk of cell or tissue damage.

Example 2. Prototype In Vivo Photoacoustic Flow Cytometry System Used to Detect Contrast Dye Circulating in Mice The following experiment was conducted to demonstrate the feasibility of in vivo photoacoustic flow cytometry (PAFC) for real-time, quantitative monitoring in the blood circulation of a conventional contrast agent, Lymphazurin. In this experiment, a prototype PAFC system was used to detect Lymphazurin circulating in the blood vessels of a mouse ear.

The prototype PAFC system was built on the platform of an Olympus BX51 microscope (Olympus America, Inc.) and a tunable optical parametric oscillator (OPO) pumped by a Nd:YAG laser (Lotis Ltd., Minsk, Belarus). The general layout of the PAFC system is shown in FIG. 2. Laser pulses had an 8 ns pulse width, a regular repetition rate of 10 Hz with the ability to provide short-term pulses at 50 Hz, and a wavelength in the range of 420-2,300 nm. Laser energy was directed to the blood vessels using a conventional lens, or an optical fiber. PA waves emitted by the cells were detected by ultrasound transducers (unfocused Panametrics model XMS-310, 10 MHz; focused cylindrical Panametrics model V312-SM, 10 MHz, focused lengths of 6 mm, 12 mm, and 55 mm; and customized resonance transducers), and the ultrasound transducer outputs were conditioned by an amplifier (Panametrics model 5662, bandwidth 50 kHz-5 MHz; Panametrics model 5678, bandwidth 50 kHz-40 MHz; customized amplifiers with adjustable high and low frequency boundaries in the range to 50-200 KHz and 1-20 MHz, respectively; resonance bandwidth of 0.3-1.0 MHz). The amplifier output signals were recorded with a Boxcar data acquisition system (Stanford Research Systems, Inc.) and a Tektronix TDS 3032B oscilloscope, and were analyzed using standard and customized software. The Boxcar data acquisition technique provided averaging of the PA waves from cells in the blood vessels, and discriminated the PA waves from background signals from surrounding tissue on the basis of the difference in time delays between the two signals. The signals from the oscilloscope screen were recorded with a digital camera (Sony, Inc.) and video camera (JVC, Inc.).

A high-speed computer (Dell Precision 690 workstation with a quadcore processor, 4 GB of RAM and Windows Vista 64 bit operating system) and digitizer (National Instruments PCI-5124 high speed digitizer) were used to acquire the PA signal data from the PAFC device. National Instruments software (Labview Version 8.5 and NI Scope Version 3.4) was used to control the digitizer and create a data logging user interface. The hardware and supporting program were capable of collecting data at a rate of 200 megasamples per second, corresponding to a time resolution of 5 ns.

A laser beam with a circular cross section and a diameter of approximately 50 µm, a wavelength of 650 nm, and a fluence of 35 mJ/cm$^2$ was used to illuminate the flow in the blood vessels. The 650 nm wavelength used was near the wavelength of maximum absorption of Lymphazurin, the contrast dye used in this experiment, and well separated from the wavelengths of maximum absorption of other blood components. Navigation of the laser beams was controlled with transmission digital microscopy (TDM) at a resolution of approximately 300 nm using a Cascade 650 CCD camera (Photometrics).

All in vivo experiments described below were performed using a nude mouse ear model. PAFC detection was performed using relatively transparent, 270 µm thick mouse ears with well-distinguished blood microvessels. The ear blood vessels examined were located at a depth of 30-100 µm, had diameters in the range of 30-50 µm, and blood velocities of 1-5 mm/sec. After undergoing anesthesia using ketamine/xylazine at a dosage of 50/10 mg/kg, each mouse was placed on a customized heated microscope stage, together with a topical application of warm water, which provided acoustic matching between the transducer and mouse ear.

The contrast dye used for the experiments described below was Lymphazurin, a contrast agent commonly used for the delineation of lymphatic vessels. A 1% solution of Lymphazurin (Isosulfan Blue) was purchased from Ben Venue Labs Inc., USA.

After anaesthetizing each mouse and placing the mouse on the microscope stage as described above, 200 µl of a 1% aqueous solution of Lymphazurin was injected into the tail vein of the mouse.

PAFC measurements of the circulating dye were performed at a laser pulse wavelength of 650 nm. FIG. 3 shows oscilloscope traces of PAFC signals from the blood vessels and surrounding tissues in the rat ear before and after injection with Lymphazurin. Prior to injection, the maximum 240 mV PA signals from blood vessels, shown in FIG. 3A, were approximately 1.5 times higher than the 160 mV PA background signals from surrounding tissue, shown in FIG. 3B. Maximum PA signals from the blood vessel after dye administration, shown in FIG. 3C, increased approximately three-fold over pre-injection levels. The PA signals from tissue around vessels after dye injections, shown in FIG. 3D, gradually increased approximately 2.5-fold over pre-injection levels during the first 15-20 minutes, and then remained relatively constant for the next 1-1.5 hours, probably due to the passage of the Lymphazurin out of the blood vessels and into nearby lymphatic vessels.

Figure 4:
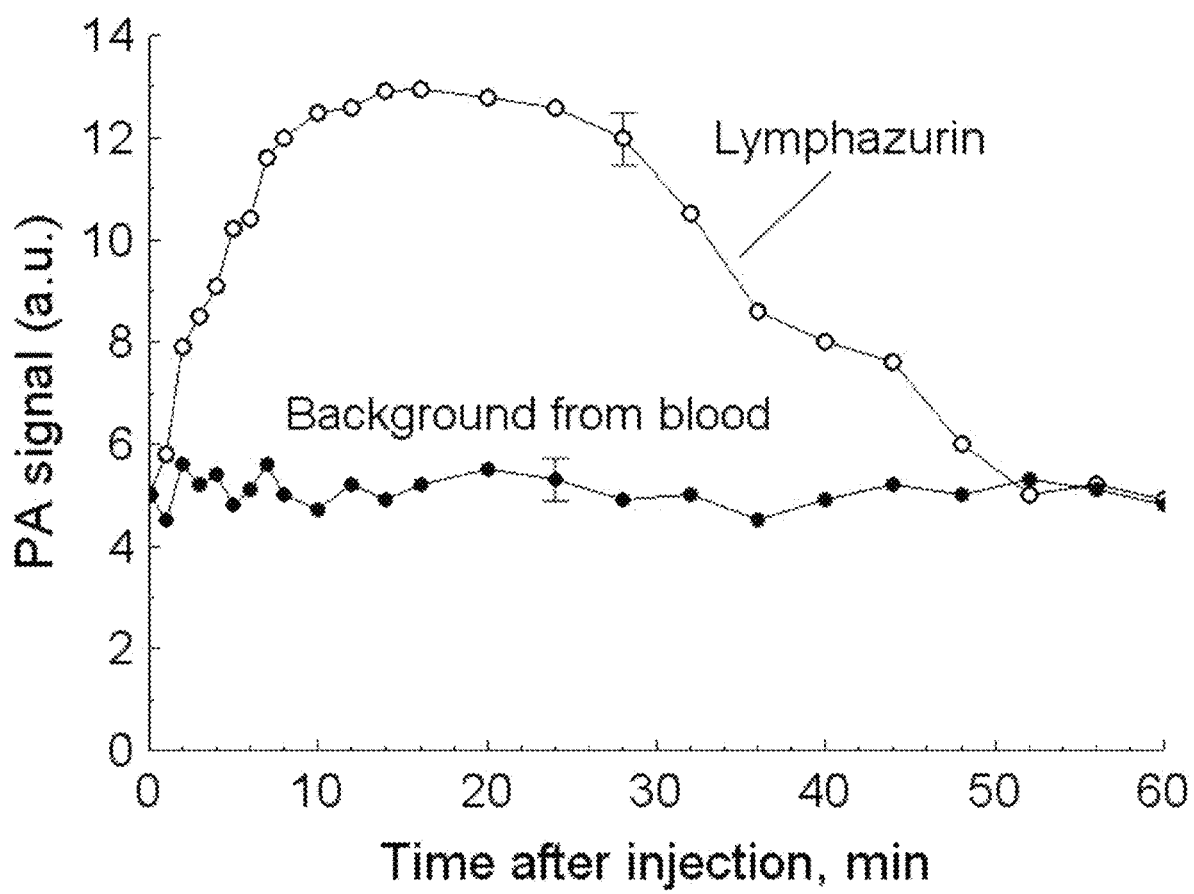
FIG. 4 shows the PA signal detected from the monitoring of the blood flow in a 50-µm rat ear microvessel with diameter after intravenous injection of Lymphazurin dye in the tail vein.

FIG. 4 summarizes the maximum PAFC signals from Lymphazurin compared to background PAFC signals from the blood vessels, observed for one hour after the injection of Lymphazurin. As shown in FIG. 4, continuous monitoring of PA signals from the ear blood microvessels revealed a rapid appearance of Lymphazurin in the blood flow within a few minutes after injection, followed by clearance of Lymphazurin from the blood over the next 50 minutes.

The results of this experiment demonstrated that the prototype PAFC system exhibited sufficient sensitivity to detect the presence of ultrasonic contrast dyes in circulation.

Example 3. Prototype In Vivo Photoacoustic Flow Cytometry System Used to Detect Nanoparticles Circulating in Rats To demonstrate the sensitivity of a prototype in vivo photoacoustic flow cytometry (PAFC) system described in Example 2 an experiment was conducted using the prototype PAFC system to detect nanoparticles intravenously injected into the tail veins of rats.

The in vivo measurements in this experiment were performed using the rat mesentery model. The rat (White Fisher, F344) was anesthetized using ketamine/xylazine at a dosage of 60/15 mg/kg, and the mesentery was exposed and placed on a heated microscope stage, and bathed in Ringer's solution at a temperature of 37° C. and a pH of 7.4. The mesentery consisted of transparent connective tissue of 7-15 µm thickness, and a single layer of blood and lymph microvessels.

The nanoparticles used in this experiment were gold nanorods (GNR), obtained from the Laboratory of Nanoscale Biosensors at the Institute of Biochemistry and Physiology of Plants and Microorganisms in Saratov, Russia. On the basis of TEM and dynamic light scattering analyses, the GNR were estimated to be approximately 15 nm in diameter and approximately 45 nm in length on average. The nanoparticles were used either uncoated, or functionalized using thiol-modified polyethylene glycol (PEG) (Liao and Hafner 2005).

A 250-µL suspension of GNR with a concentration of $10^{10}$ particles/ml was injected into the tail veins of three rats, followed by the continuous monitoring of PA signals measured from 50-µm diameter blood vessels in the rat mesentery using the PAFC system described in Example 2. PAFC measurements were taken using a laser fluence of 100 mJ/cm$^2$, a laser beam diameter of approximately 50 µm, and a laser wavelength of 830 nm, near the maximum absorption of the GNR.

Figure 5:
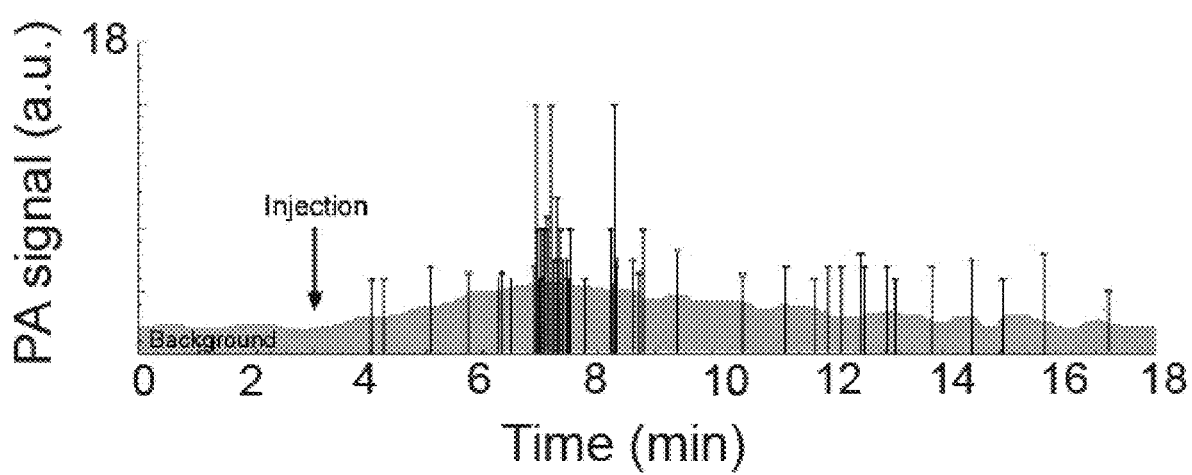
FIG. 5 shows the PA signal from circulating GNR in 50-µm rat mesentery microvessels as a function of post-injection time.

Uncoated GNR were rapidly cleared from the blood circulation within 1-3 minutes preferentially by the reticuloendothelial system (data not shown). After PEGylated GNR injection, strong fluctuating PA signals appeared with amplitudes significantly exceeding the PA background signals from blood vessels within the first minute and continued for 14-25 minutes, depending on the individual animal. In addition, the PA background signal from the blood vessel increased approximately 1.5-2 times above the pre-injection background levels, reaching a maximum level between four and nine minutes after injection, as shown in FIG. 5.

Figure 6:
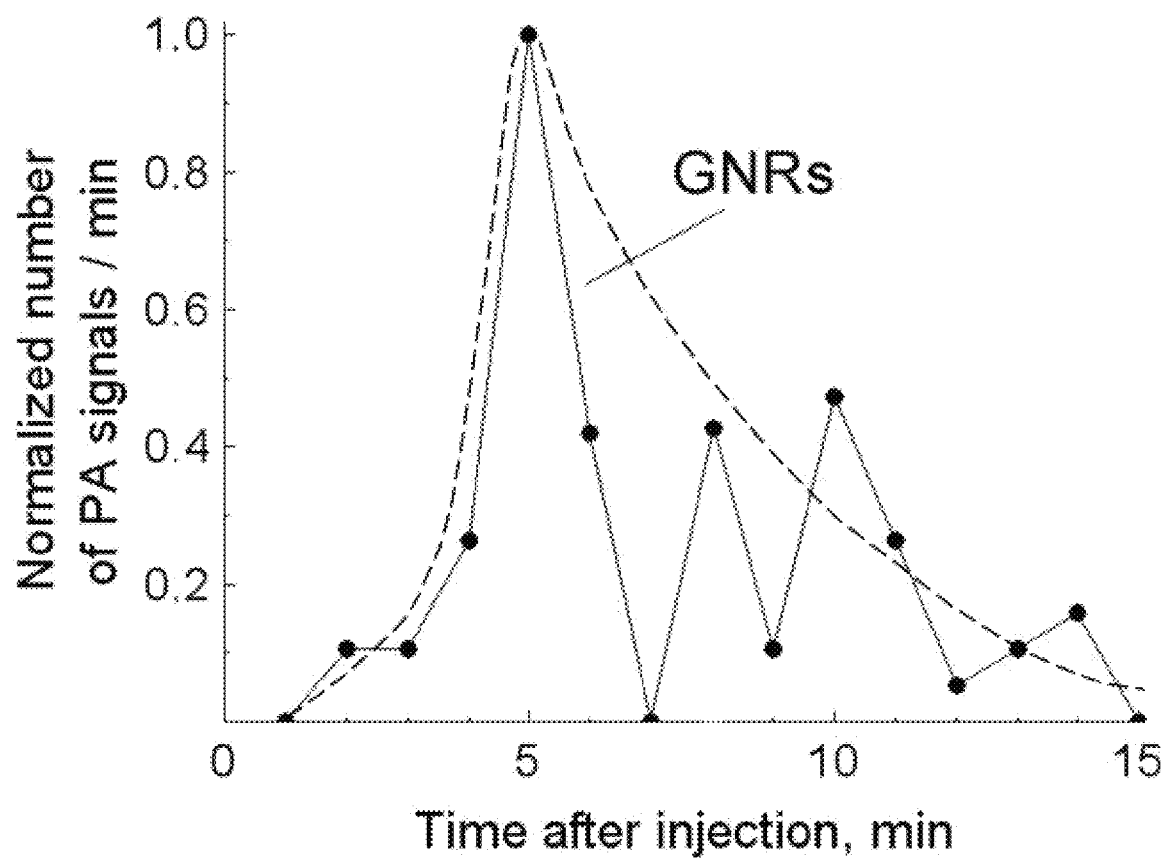
FIG. 6 is a graph of the normalized number of circulating GNR in blood microvessels of the rat mesentery as a function of post-injection time and a dashed curve showing averaged data (N=3).

The averaged PA signals from three animals, measured for 15 minutes after injection with GNR suspensions, are summarized in FIG. 6. The maximum rate of individual PA signals per minute, representing the number of GNR in circulation, was achieved approximately 5 minutes after injection, with a gradual decrease in the signal rate over the next 10 minutes.

The results of this experiment demonstrated that the prototype PAFC system possessed sufficient spatial and temporal resolution to continuously monitor the circulation of nanoparticles as small as 15 nm in diameter. In addition, the prototype PAFC system was sufficiently sensitive to track fluctuations of the concentration of circulating particles from the time that they were injected to the time that the particles were cleared from circulation.

Example 4. Prototype In Vivo Photoacoustic Flow Cytometry System Used to Detect S. aureus Bacteria Circulating in Mice To demonstrate the ability of the prototype photoacoustic flow cytometry (PAFC) system to detect bacteria cells in vivo under biological conditions, the following experiment was conducted. The prototype PAFC system, previously described in Example 2, was used to measure S. aureus bacteria in the circulation of nude mice.

The mouse ear model described in Example 2 was used for all measurements of circulating bacteria in the experiment. Because the endogenous light absorption of S. aureus bacteria was relatively weak compared to the absorption of other blood components in the NIR spectral range, the bacteria were labeled with the NIR-absorbing contrast substances indocyanine green dye (ICG) and carbon nanotubes (CNT), due to their relatively high labeling efficiency and low toxicity (data not shown).

The S. aureus bacterium strain designated UAMS-1 was isolated from a patient with osteomyelitis at the McClellan Veterans Hospital in Little Rock, Arkansas, USA. The strain was deposited with the American Type Culture Collection and is available as strain ATCC 49230. UAMS-1 was cultured in tryptic soy broth and grown aerobically for 16 h at 37° C. Cells were harvested by centrifugation, resuspended in sterile PBS and incubated with Indocyanine Green (ICG) dye (Akorn Inc., USA) or carbon nanotubes (CNT) as described below.

Before incubation, ICG dye was filtered through a 0.22 µm pore size filter. A 150-µl aliquot of bacteria in suspension was incubated with 375 µg of ICG in 150 µl of solution for 30 min at room temperature and then for 2 h at 37° C. Labeled bacteria were centrifuged at 5,000 rpm for 3 min and the resulting pellet was resuspended in PBS.

Single-walled and multi-walled carbon nanotubes (CNT) were purchased from Carbon Nanotechnologies Inc. (Houston, TX) and Nano-lab Inc. (Newton, MA), respectively. The CNT samples used in this study were processed using known methods (Kim et al. 2006). The average length and diameter of the single-walled CNT were 186 nm and 1.7 nm respectively, and the average length and diameter of the multi-walled CNT were 376 nm and 19.0 nm respectively.

CNT solutions were treated with five cycles of 1.5 min of ultrasound at a power of 3 W followed by 0.5 min of rest, for a total of 10 minutes of interrupted ultrasound. A 150-µl aliquot of bacteria in suspension was incubated with 150 µl of CNT solution for 30 minutes at room temperature followed by 2 additional hours of incubation at room temperature. Labeled bacteria were centrifuged at 10,000 rpm for 5 min and the resulting pellet was resuspended in PBS.

Labeled 100-µl suspensions of S. aureus bacteria at a concentration of $5 \times 10^5$ cells/ml were injected into the mouse's tail vein, and the clearance of the labeled bacteria was monitored using PAFC measurements taken from 50-µm diameter microvessels in the ears of mice. Laser energy was delivered at a wavelength of 805 nm for the S. aureus that was labeled with ICG, and at a wavelength of 850 nm for the S. aureus that was labeled with CNT. For both label types, the laser energy was delivered at a beam diameter of approximately 50 µm and at a fluence ranging between 20 and 50 mJ/cm$^2$.

Figure 7:
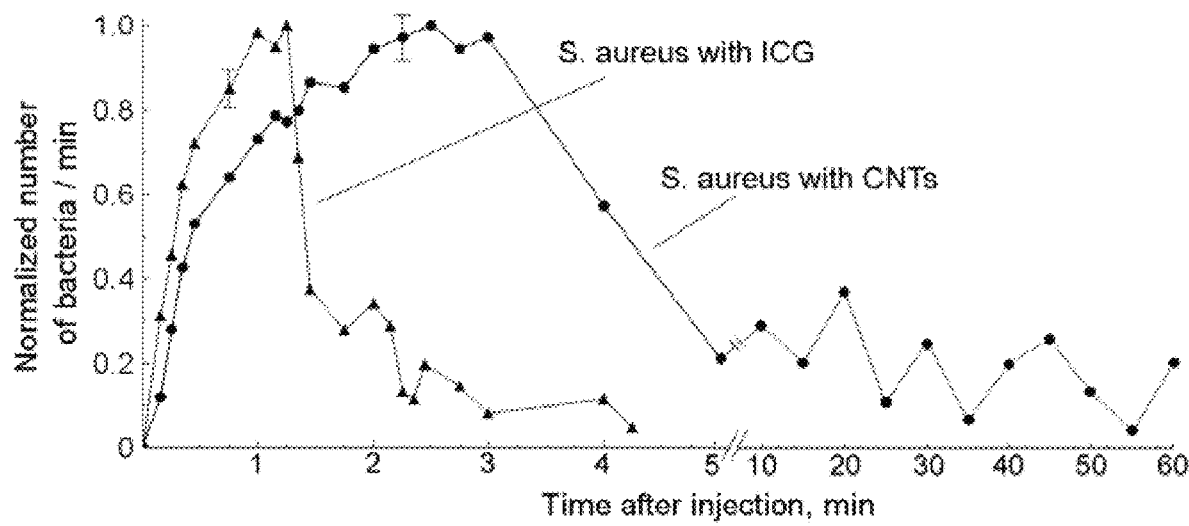
FIG. 7 is a graph of the normalized number of circulating *S. aureus* in blood microvessels of the mouse ear as a function of post-injection time, for bacteria labeled using two different contrast substances, ICG dye and CNT.

S. aureus bacteria labeled with ICG and CNT contrast substances yielded similar results, summarized in FIG. 7. After injection of labeled S. aureus, PAFC detected a rapid appearance of bacteria in the ear blood microvessels within the first minute, followed by a steady elimination of the bacteria from the blood circulation over the next 3-5 minutes. Periodic PAFC monitoring of mice blood vessels over the next few days revealed that very rare bacteria labeled with CNT or possibly unattached CNT continued to appear at an average rate of one PA signal every three minutes, and the labeled bacteria or CNT was not completely cleared from circulation until about 60 hrs after the initial injection (data not shown).

The results of this experiment established the feasibility of PAFC for the in vivo monitoring of individual cells in the circulatory systems of living organisms. Using appropriate contrast enhancement substances, the laser fluence required for effective detection of cells in circulation was well below the threshold levels for laser-induced cell damage.

Example 5. Prototype In Vivo Photoacoustic Flow Cytometry System Used to Detect E. coli Bacteria Circulating in Mice To demonstrate the ability of the prototype photoacoustic flow cytometry (PAFC) system to detect bacteria cells in vivo under biological conditions, the following experiment was conducted. The prototype PAFC system, previously described in Example 2, was used to detect the bacteria E. coli strain K12, in the circulation of nude mice.

The mouse ear model described in Example 2 was used for all measurements of circulating bacteria in the experiments described below. Because the endogenous light absorption of E. coli bacteria was relatively weak compared to the absorption of other blood components in the NIR spectral range, the bacteria were labeled with NIR-absorbing carbon nanotubes (CNT).

E. coli K12 strain was obtained from the American Type Culture Collection (Rockville, MD) and maintained in Luria-Bertani (LB) medium, a solution consisting of 1% tryptone, 0.5% yeast extract, and 0.5% NaCl at a pH of 7. A 100-µl aliquot of E. coli in PBS was incubated with 100 µl of the CNT solution as described in Example 4 for 60 min at room temperature.

Figure 8:
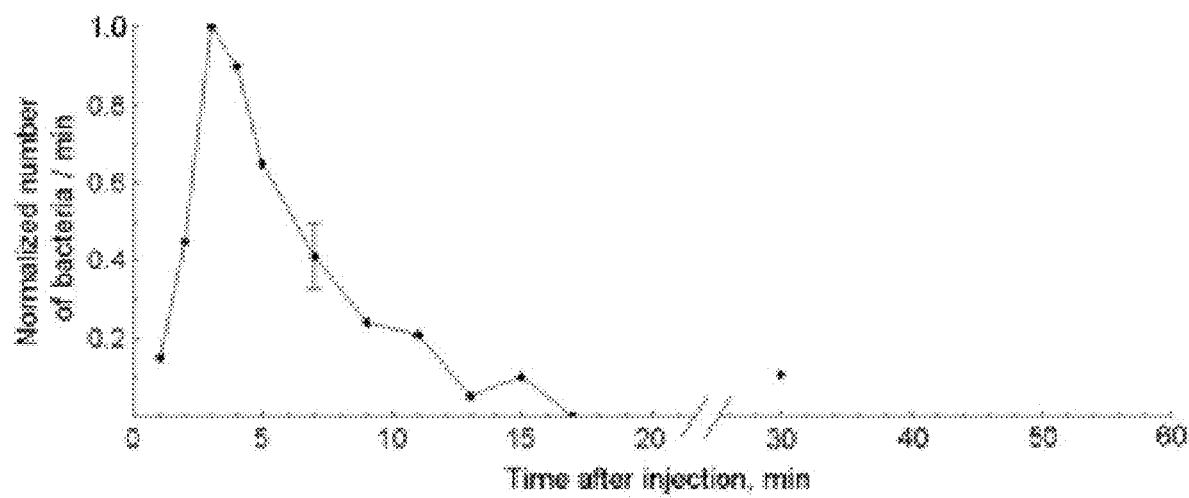
FIG. 8 is a graph of the normalized number of circulating *E. coli* in blood microvessels of the mouse ear as a function of post-injection time.

100-µl suspensions of CNT-labeled E. coli bacteria at a concentration of $5 \times 10^5$ cells/ml were injected into the mouse's tail vein, and the clearance of the labeled bacteria was monitored using PAFC measurements taken from 50-µm diameter microvessels in the ears of mice. Laser energy was delivered at a wavelength of 850 nm, a beam diameter of approximately 50 µm and at a laser fluence of 100 mJ/cm$^2$. PAFC measurements, summarized in FIG. 8, detected a rapid appearance of the bacteria in circulation after injection, and the bacterial concentrations in the blood decreased exponentially over the next 15-17 minutes.

The results of this experiment confirmed the feasibility of PAFC for the in vivo monitoring of individual cells in the circulatory systems of living organisms. The laser fluence required for effective detection of E. coli cells in circulation was well below threshold levels for laser-induced cell damage.

Example 6. In Vivo PAFC Used to Detect Circulating Exogenous Melanoma Cells

To demonstrate the ability to use in vivo PAFC to detect unlabeled melanoma cells in circulation with extremely high sensitivity through skin cells with varying levels of melanin pigmentation, the following experiment was conducted.

B16F10 cultured mouse melanoma cells (ATCC, Rockville, MD) were used in this experiment. The cells were maintained using standard procedures (Ara et al. 1990, Weight et al. 2006, Zharov et al. 2006), including serial passage in phenol-free RPMI 1640 medium (Invitrogen, Carlsbad, CA) supplemented with 10% fetal bovine serum (FBS, Invitrogen). For comparison to the detection of unlabelled melanoma cells, the endogenous cell absorption was increased by staining with ICG (Akorn Inc., USA), a strongly absorbent dye in the NIR range, for 30 min at 37° C. and in the presence of 5% $CO_2$. No toxicity was observed after labeling as assessed using the trypan blue exclusion assay (data not shown).

Figure 9:
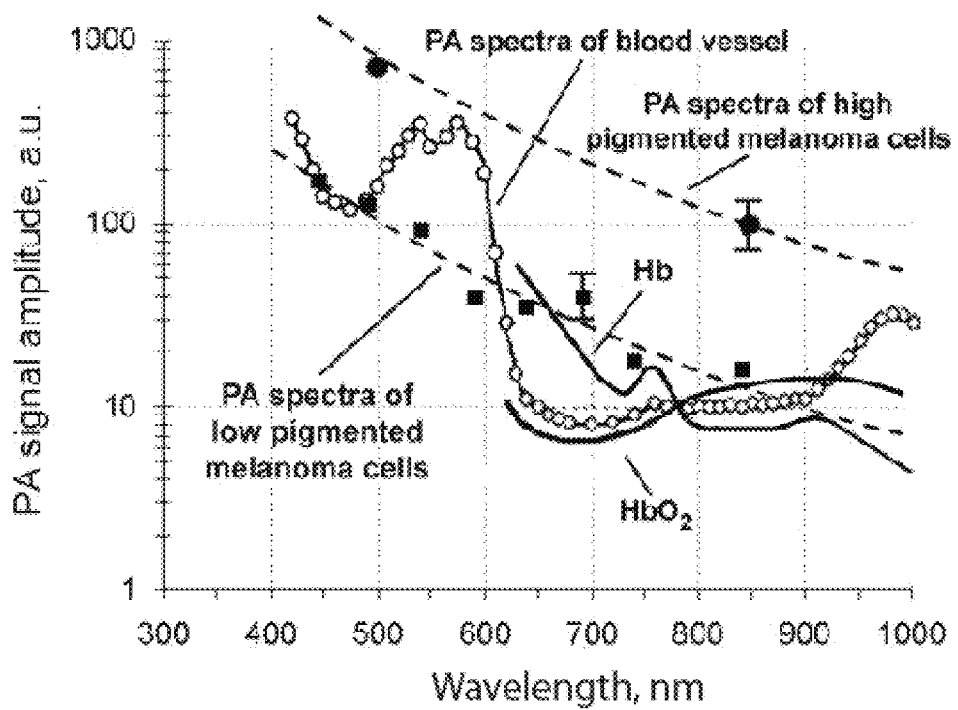
FIG. 9 shows the PA spectra of 50-µm diameter veins in the mouse ear (empty circles), conventional absorption spectra of the B16F10 mouse melanoma cells with strong pigmentation (upper dashed curve) and weak pigmentation (lower dashed curve), spectra normalized using PA signals for the single mouse melanoma cells with strong pigmentation (black circles) and weak pigmentation (black squares), and absorption spectra for pure Hb and $HbO_2$ (fragments of solid curves in the spectral range 630-850 nm).

In vivo measurements of melanoma cells used the PAFC system previously described in Example 2 with a laser wavelength of 850 nm and a laser fluence of 80 mJ/cm$^2$. This wavelength falls within a region in which the absorbance of melanoma cells is relatively high compared to the absorbance of hemoglobin, a major component of blood, as determined by in vitro measurements summarized in FIG. 9.

To estimate the influence of endogenous skin melanin on PAFC detection limits, Harlan Sprague mice, strain: NIH-BG-NU-XID were used in this experiment. Female mice of this strain possess high levels skin pigmentation between 8 and 10 weeks of age. Mice were anaesthetized and placed on the heated microscope stage as previously described in Example 2.

Figure 10A:
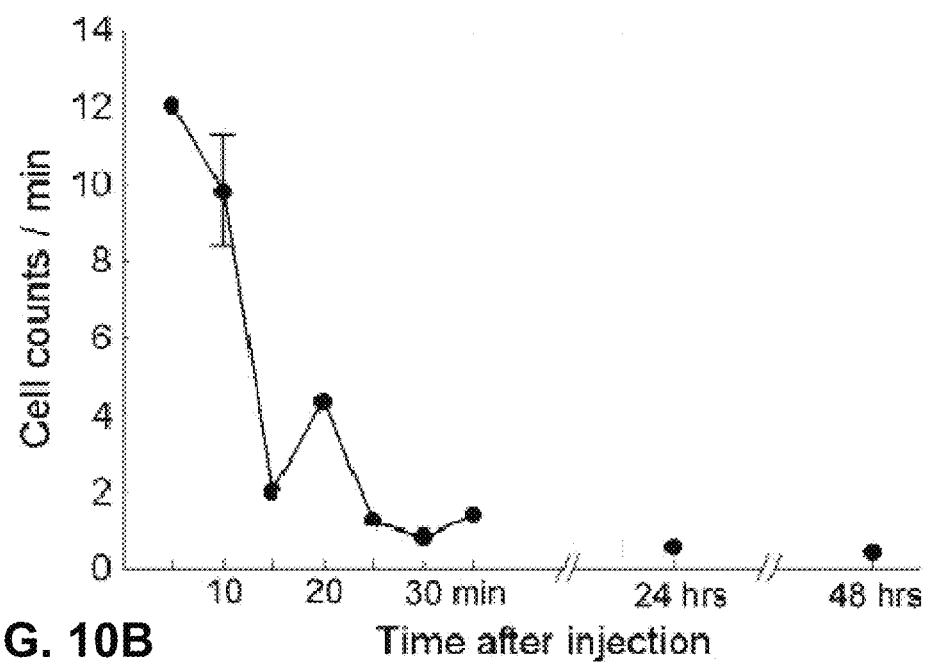
FIG. 10A is a graph showing the frequencies of circulating mouse melanoma cells (B16F10) detected with label-free PAFC in 50-µm mouse ear veins, with a flow velocity of 5 mm/s, in mice with low melanin pigmentation as a function of post-injection time.
Figure 10B:
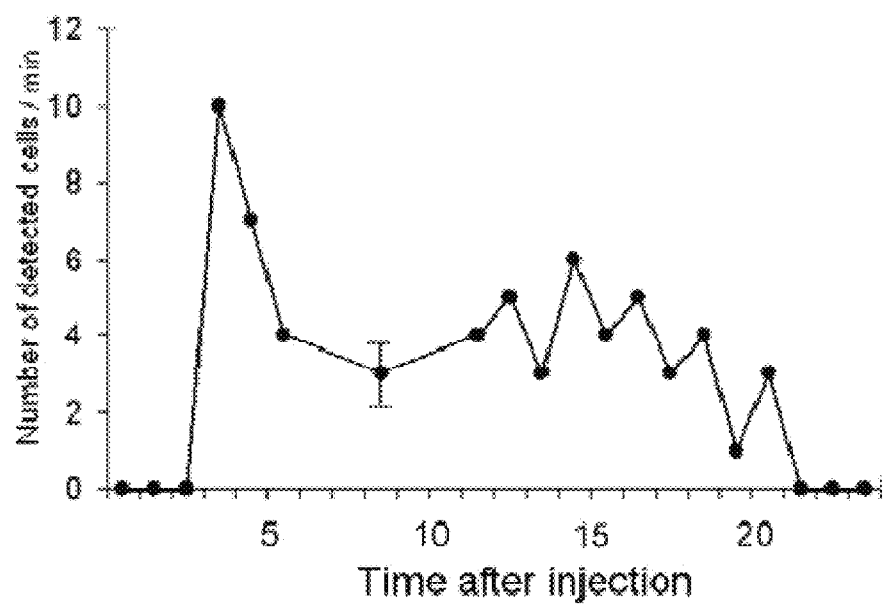
FIG. 10B is a graph showing the frequencies of circulating mouse melanoma cells (B16F10) detected with label-free PAFC in 50-µm mouse ear veins, with a flow velocity of 5 mm/s, in mice with high melanin pigmentation as a function of post-injection time.

A 200-µl volume of saline solution containing approximately $10^5$ mouse melanoma cells was injected into the mouse circulatory system through a tail vein and then monitored using the PAFC system. The number of melanoma cells per minute detected using PAFC for melanoma cells after injection are summarized in FIG. 10 for melanoma cells with low melanin content (FIG. 10A) and for melanoma cells with high melanin content (FIG. 10B). In the first 5 minutes of PA detection following intravenous injection of cultured mouse melanoma cells, 600±120 PA signals (representing melanoma cells) per hour were observed, and the rate of detection of melanoma cells steadily decreased over the subsequent 20-30 min. Approximately 20 cells/hour and 4 cells/hour were detected after 24 h and 48 h of monitoring, respectively. The initial PA signal rate after the injection of melanoma cells stained with ICG contrast enhancement substances was 720±105 cells/hour (data not shown). Assuming that all stained melanoma cells were detected by in vivo PAFC, 82.4% of the unlabelled melanoma cells in circulation were detected by in vivo PAFC measurements.

The results of this experiment demonstrated the ability of in vivo PAFC to detect and monitor the appearance and progression of metastatic melanoma cells in circulation non-invasively.

Example 7. In Vivo PAFC was Used to Detect Circulating Spontaneous Metastatic Cells During Tumor Progression An experiment was conducted to determine the ability of in vivo PAFC to detect relatively scarce endogenous metastatic melanoma cells circulating in lymph vessels. The PAFC system described in Example 2 was used to monitor endogenous metastatic melanoma cells in mice. The laser characteristics used in this experiment are identical to those described in Example 5.

Nude mice were anaesthetized and placed on the heated microscope stage as previously described in Example 2. The ear blood vessels under examination were located 50-100 µm deep and had diameters of 35-50 µm with blood velocities of 3-7 mm/sec. To increase the probability of detection of rare metastatic cells, blood vessels with relatively large diameters of 150-300 µm and flow velocities up to 10-30 mm/s in the skin of the abdominal wall were examined using a customized skin fold chamber.

50-µl suspensions containing $10^6$ B16F10 cultured mouse melanoma cells (ATCC, Rockville, MD) were subcutaneously injected into nude mice. Melanoma tumors subsequently formed in the ears of the mice and in the skin on the backs of the mice. PAFC was performed on ear and abdominal blood vessels to monitor the circulatory system for the appearance of metastatic cells, and PA mapping, described below, was used to monitor the growth of tumors.

During ear tumor development, individual or groups of melanoma cells were first detected in the skin area close to the tumor site on the sixth day following tumor inoculation using PA mapping measurements. PA mapping measurements utilized PA signals derived by scanning a focused laser beam with diameter of 10 µm across ear. Metastatic cells first appeared in ear microvessels near the tumor on the twentieth day after inoculation at a rate of 12±5 cells/hour (data not shown). Surprisingly, during the same time period, no melanoma cells had yet been detected in the abdominal skin blood vessels. 25 days after inoculation, the average count of melanoma cells detected in the ear veins increased to 55±15 cells/hour, and at this same time, melanoma cells were detected in abdominal wall skin vessels at a rate of 120±32 cells/hour. Thirty days after inoculation, the detection rate decreased to 30±10 cells/hour in the abdominal vessel, which may be attributed to inhibition of metastatic cell production in the primary tumor. PA mapping of selected tissue and organs revealed multiple micrometastases in cervical and mesenteric lymph nodes, as well as in lung and liver tissues.

PAFC measurements of the nude mouse back tumor model revealed the appearance of metastatic melanoma in abdominal skin blood vessels close to the tumor site on day 5, much earlier than in the tumor ear model. This indicates a much greater likelihood of detecting the initial metastatic process in the vicinity of the primary tumor.

Thirty days after tumor inoculation, the average concentration of melanoma cells was 150±39 cells/ml, corresponding to a circulating rate of approximately 4-10 cells/min in a 50-mm blood vessel and a flow velocity of 5 mm/s. The ultimate PAFC threshold sensitivity of the nude mouse back tumor model was estimated as 1 cell/ml. This circulating rate corresponded to an incidence of approximately one melanoma cell among 100 million normal blood cells.

The results of this experiment indicated that in vivo PAFC and PA mapping were sensitive methods with which to monitor the development of metastasized melanoma cells non-invasively, with high sensitivity and accuracy.

Example 8. In Vivo PAFC was Used to Detect Spontaneous Metastatic Cells in Lymphatic Vessels During Tumor Progression To determine the feasibility of detecting individual metastatic cells in lymph flow, the following experiment was conducted. A photoacoustic flow cytometer (PAFC) was used to monitor lymph flow for the presence of WBC, RBC, and metastatic melanoma cells.

The animal models used in this experiment were nu/nu nude mice, weighing 20-25 g (Harlan Sprague-Dawley). PAFC measurements were taken using the lymphatic vessels in the ears using a heated platform as described in Example 2. Melanoma tumors in the ear and back skin of the mice were induced by the subcutaneous injection of B16F10 mouse melanoma cells as described in Example 6.

To locate the lymphatic vessels in the mouse ear, a PA mapping process using a PA contrast agent was used. Ethylene blue (EB) dye, commonly used for lymphatic research, was injected into the lymphatic vessel walls. A 639 nm laser beam was then used to illuminate the lymphatic vessel at a wavelength of 639 nm, corresponding to the maximum absorption of EB dye, and the resulting PA signal emitted by the EB dye was monitored. The position of the laser beam on a lymph vessel was fixed when the PA signal amplitude reached its maximum at the laser wavelength of 639 nm.

Figure 11:
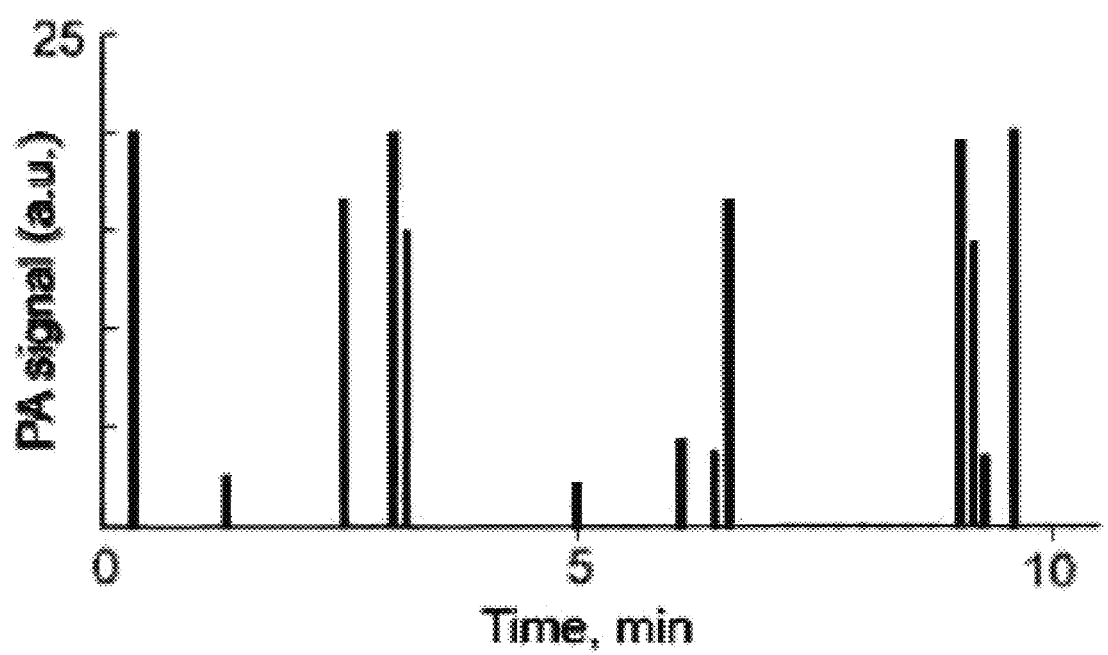
FIG. 11 is a summary of the PA signal rates from single melanoma cells detected in a mouse ear lymph microvessel 5 days after tumor inoculation.

In vivo PAFC detection of unlabeled melanoma cells relied on melanin as an intrinsic cell marker, as in Example 7. Melanoma cells were detected using a laser wavelength of 850 nm, a laser fluence of 35 mJ/cm$^2$, and a laser beam diameter of approximately 50 µm. In mice with induced skin melanomas, metastatic cells were observed to appear in a lymphatic vessel of the mouse's ear on the fifth day after inoculation at a rate of 1.2±0.5 cells/min, which steadily increased over the course of 2 weeks (data not shown). In mice with a melanoma tumor in the ear, melanoma cells appeared in skin lymphatics 20 days after inoculation. 30 days after inoculation strong PA signals detected the presence of metastatic melanoma cells in the sentinel lymph nodes, which was later confirmed by histology (data not shown). FIG. 11 shows the PA signals detected from single metastatic melanocytes circulating in the lymphatic vessel in the mouse ear five days after tumor inoculation.

The results of this experiment demonstrated the feasibility of detecting relatively scarce metastatic melanoma cells circulating in the lymphatic system using in vivo PAFC techniques, with high sensitivity and accuracy.

Example 9. In Vivo PAFC was Used to Detect Red Blood Cells and Lymphocytes Simultaneously Circulating in Lymph Vessels To determine the feasibility of detecting unlabeled individual cells of different types circulating in lymph flow, the following experiment was conducted. A photoacoustic flow cytometer (PAFC) was used to monitor lymph flow for the presence of red blood cells and lymphocytes.

The animal models used in this experiment were 150-200 g rats (Harlan Sprague-Dawley). PAFC measurements were taken using lymphatic vessels in the mesentery of the rat, using the method described in Example 3. Lymphatic vessels were located, and the laser was focused on the lymphatic vessel using the methods described in Example 8.

Spectroscopic studies in vitro revealed that PA signals from lymphocytes reached maximal amplitude in the visible-spectral range near 550 nm, associated with cytochrome c acting as an intrinsic absorption marker (data not shown). Background PA signals from vessels and surrounding tissues were approximately 4-6-fold less than from single lymphocytes at this wavelength due to the low level of background absorption and laser focusing effects.

Figure 12:
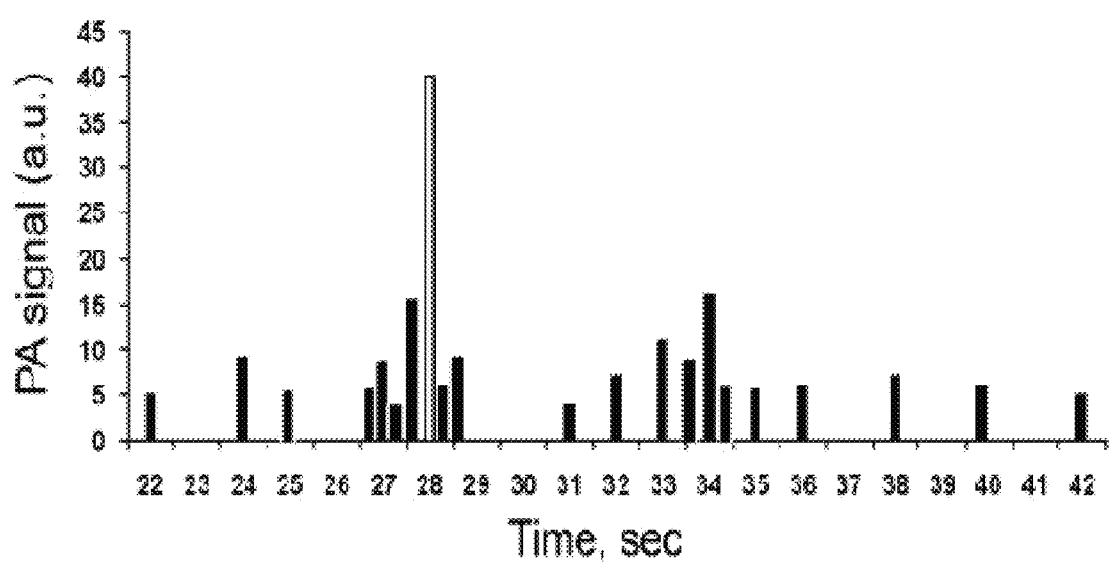
FIG. 12 is a summary of the PA signal rates from a single RBC (white bar) and lymphocytes (black bars) detected by PAFC in the lymph flow of rat mesentery.

The in vitro PAFC system described in Example 2 was used to detect circulating cells in the lymphatic vessels of the rat mesentery. The laser used in the PAFC system had a wavelength of 550 nm and a fluence of 100 mJ/cm$^2$, and a circular beam diameter of approximately 50 μm. The cell detection rate obtained in lymphatic vessels was 60±12 cells/min. A graph showing the PA signals detected by the PAFC system in a rat mesentery lymphatic vessel is shown in FIG. 12. Lymphocyte heterogeneity resulted in 2-2.5-fold fluctuations in PA signal amplitude from cell to cell. A small fraction of the detected cells had strong PA signal amplitudes exceeding those of the lymphocyte signals by a factor of 10 to 20-fold. One such strong PA signal is shown as a white bar in FIG. 12 at 28 seconds. Subsequent spectral and imaging analysis identified rare single red blood cells (RBCs) as the sources of these excessively strong PA signals.

The results of this experiment demonstrated that the in vivo PAFC system possessed sufficient sensitivity and accuracy for the simultaneous detection of red blood cells and lymphocytes circulating in the lymphatic vesicles.

Example 10. In Vivo Two-Wavelength PAFC was Used to Discriminate Between 3 Different Exogenously Labeled Cell Types in Circulation within Lymph Vessels To demonstrate the ability of the photoacoustic flow cytometry (PAFC) system to detect cells using more than one wavelength of laser light, the following experiment was conducted. In this experiment, a PAFC system was used to detect exogenous blood cells that were labeled with three different nanoparticles, while circulating in blood vessels (data not shown) and in lymphatic vessels. The PAFC system detected the cells by illuminating the cells with laser pulses of two different wavelengths in the near-infrared (NIR) spectrum.

A PAFC system similar to that described in Example 2 was used to detect the circulating cells. However, in the PAFC system used in this experiment, the laser of the PAFC system pulsed light at two different wavelengths, corresponding to the wavelengths of maximum absorption for two of the nanoparticles used to label the cells. The first laser pulse was at a wavelength of 865 nm, a laser fluence of 35 mJ/cm$^2$, and pulse duration of 8 ns. 10 μs after the end of the first laser pulse, a second laser pulse was delivered at a wavelength of 639 nm, a laser fluence of 25 mJ/cm$^2$, and pulse duration of 12 ns. The paired laser pulses were repeated at a frequency of 10 Hz.

The animal models used in this experiment were nu/nu nude mice, weighing 20-25 g (Harlan Sprague-Dawley). PAFC measurements were taken using lymphatic vessels in the mesentery of the mouse, using the methods described in Example 3. Lymphatic vessels were located, and the laser was focused on the lymphatic vessel using the methods described in Example 8.

Normal fresh blood cells were obtained from heparinized whole-blood samples of donor mice after terminal blood collection. Red blood cells were isolated by simple centrifugation, and lymphocytes were isolated by Histopaque (Sigma-Aldrich) density gradient centrifugation as recommended by the supplier.

The nanoparticles used to label the various blood cells used in this experiment were gold nanorods (GNR) and gold nanoshells (GNS), provided by The Laboratory of Nanoscale Biosensors at the Institute of Biochemistry and Physiology of Plants and Microorganisms in Saratov, Russia. The GNR had an average diameter of 16 nm, an average length of 40 nm, and a relatively narrow absorption band of 660±50 nm. The GNS had an average diameter of 100 nm, and a maximum absorption near 860 nm. Both GNR and GNS were coated with polyethylene glycol in the process described in Example 3. Single-walled CNT with an average length of 186 nm and an average diameter of 1.7 nm were purchased from Carbon Nanotechnologies Inc. CNT absorb laser energy over a wide range of wavelengths with an efficiency that monotonically decreases as wavelength increases. All particles were in suspension at a concentration of about $10^{10}$ nanoparticles/ml.

Live neutrophils were labeled with the GNS, live necrotic lymphocytes were labeled with the GNR and apoptotic lymphocytes were labeled with the CNT. The cells were labeled by incubating 100-μl aliquots of each cell type in phosphate-buffered saline with 100 μl of CNT, GNR, or GNS for 15 min at room temperature.

The labeled cells, mixed in approximately equal proportions, were intravenously injected into the tail vein of the mouse. After 6 h, mesenteric lymphatics were illuminated with two laser pulses at wavelengths of 865 nm and 639 nm as described above. PA signals at a rate of 1-3 signals/min were detected at this time.

Figure 13A:
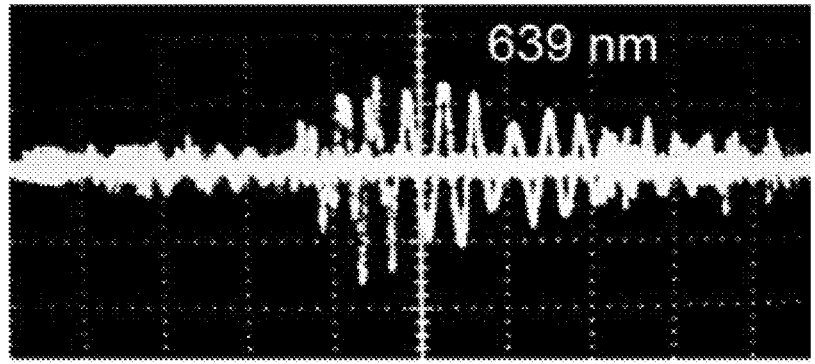
FIG. 13A shows oscilloscope traces of the two-wavelength, time-resolved detection of PA signals from necrotic lymphocytes labeled with gold nanorods absorbing 639 nm laser pulses.
Figure 13B:
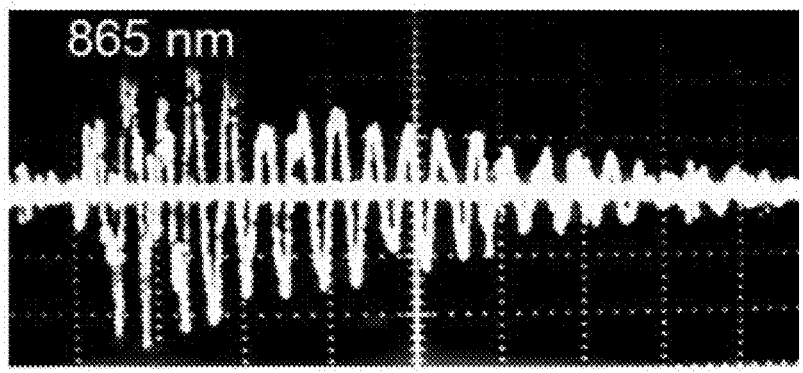
FIG. 13B shows oscilloscope traces of the two-wavelength, time-resolved detection of PA signals from apoptotic lymphocytes labeled with gold nanoshells absorbing 865 nm laser pulses.
Figure 13C:
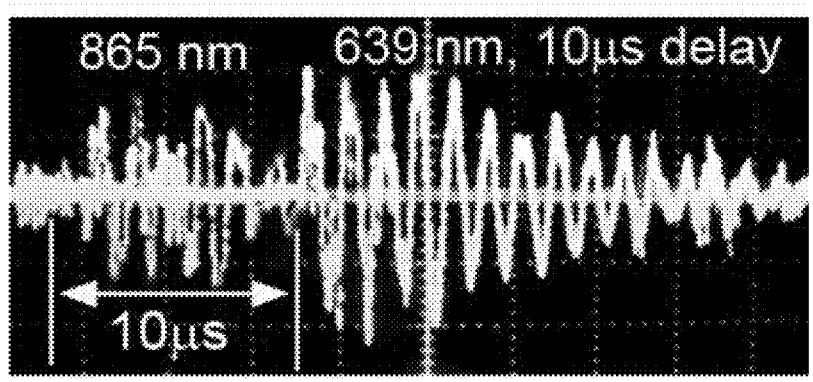
FIG. 13C shows oscilloscope traces of the two-wavelength, time-resolved detection of PA signals from live neutrophils labeled with carbon nanotubes absorbing both the 639 nm and the 865 nm laser pulses.

The PA signals had one of three distinctive temporal shapes associated with the response of the three different labels to the paired laser pulses, shown in FIG. 13. PA signals from necrotic lymphocytes marked with GNR were generated in response to the 639 nm laser pulse only, after a 10-μs delay, as shown in FIG. 13A. The apoptotic lymphocytes marked with GNS generated PA signals in response to laser pulse at a wavelength of 865 nm with no delay, as shown in FIG. 13B. Live neutrophils marked with CNT generated two PA signals after a 10-μs delay, as shown in FIG. 13C. One signal was generated in response to the 639 nm laser pulse, and the second PA signal was generated in response to the 850-nm laser pulse, due to comparable CNT absorption at both wavelengths.

The results of this experiment demonstrated that with the use of various contrast substances and two wavelength cell identification techniques, the in vivo PAFC apparatus detected and discriminated between live neutrophils, necrotic lymphocytes, and apoptotic lymphocytes that were circulating in the lymphatic vessels. This method may also be extended to unlabelled cells circulating in the lymphatic or circulatory systems, using a pair of laser pulse wavelengths selected to generate a unique PA signal shape for each cell type to be detected.

Example 11. Spatial Resolution and Maximum Detectible Vessel Depth of a Prototype In Vivo PAFC System was Assessed To determine the maximum spatial resolution and maximum detectible vessel depth of the PAFC system, the following experiment was conducted using the prototype PAFC system described in Experiment 2 and the mouse ear model with circulating melanoma cells, as described in Example 7. Mouse melanoma cells were injected into the tail veins of nude mice and PAFC measurements were conducted as described in Example 7.

The PAFC system achieved a lateral resolution of 5-15 µm when detecting melanoma cells circulating in mouse ear blood vessels with diameters of 10-70 µm at depths of 50-150 µm. However, when melanoma cells circulating in mouse ear blood vessels at a depth of 0.5 mm were measured, the lateral resolution decreased to 30-50 µm due to the scattering of the 850 nm laser pulses by the additional tissue between the PAFC laser and the targeted blood vessels.

The maximum potential of the PAFC to detect cells circulating in deep vessels was estimated by overlaying layers of mouse skin of varying thickness over intact mouse skin containing peripheral blood vessels at a depth of approximately 0.3 mm below the surface of the intact skin. Using the PAFC system described in Example 2 with an unfocused ultrasound transducer (Panametrics model XMS-310, 10-MHz), PA signals were detected at total skin thicknesses up to approximately 4 mm, with a 27-fold signal attenuation due to light scattering. When a focused ultrasound transducer was used (Panametrics model V316-SM, 20 MHz, focal length 12.5 mm), PA signals were detected from melanoma cells circulating in the mouse aorta at a depth of approximately 2.5 mm, resulting from a laser pulse wavelength of 850 nm. Even at a total tissue depth as high as 11 mm, the PA signals emitted by circulating metastatic melanoma cells illuminated by 532 nm laser pulses remained discernible from the background PA signals from surrounding tissues. The lateral resolution at this vessel depth, measured by changing the angle of the ultrasonic transducer, was estimated to be approximately 250 µm (data not shown).

The results of this experiment demonstrated that the PAFC system was capable of detecting circulating melanoma cells at a vessel depth of up to 11 mm with a resolution of approximately 250 µm. This resolution may be improved significantly through the use of higher frequency ultrasound transducers, such as 50 MHz transducers.

Example 12. The Sensitivity of the Spatial Resolution of a Prototype In Vivo PAFC Device to Skin Pigmentation Levels was Assessed Using the Nude Mouse Model To determine the sensitivity of the PAFC system to the level of skin pigmentation, the following experiment was conducted. The PAFC device described in Example 2 was used to measure PA signals from blood vessels in nude mice skin with low and high levels of pigmentation using methods similar to those described in Example 7.

In the low-pigmented nude mouse model, the background PA signal from skin cells was very weak. PA signals measured by a high frequency ultrasound transducer (Panametrics model V-316-SM, 20 MHz) resulting from the simultaneous irradiation of two circulatory vessels at depths of approximately of 0.3 mm and 2.4 mm, were determined to have a time separation of approximately 1.4 ms. This delay is consistent with signals emitted by cells with a separation distance of 2.1 mm, assuming a velocity of sound in soft tissue of approximately 1.5 mm/ms. Similar results were obtained for measurements of circulatory vessels in the highly pigmented nude mouse model (data not shown).

The results of this experiment demonstrated that the level of skin pigmentation did not significantly affect the spatial resolution of the PAFC device. For strongly pigmented skin, the assessment of deeper vessels may actually be enhanced because the skin pigmentation may facilitate the discrimination between PA signals from circulating individual cells and PA signals from the skin.

Example 13. Methods of Enriching the Incidence of Circulating Metastatic Cells Measured by PAFC In Vivo were Demonstrated Using the Mouse Ear Model To determine the feasibility of novel methods for increasing the concentrations of circulating metastatic cells detected by the in vivo PAFC device, the following experiment was conducted. Using the mouse ear model to measure the incidence of circulating metastatic melanoma cells, as described in Example 7, the effect of gentle mechanical squeezing of blood microvessels was assessed. This method of enriching the local incidence of rare circulating cancer cells in vivo exploited the size differences between melanoma cells (16-20 mm), WBC (7-8 mm), and RBC (5-6 mm) and the high deformability of RBC compared to cancer cells. The lumen size of the microvessel was decreased to 10-15 µm through gentle mechanical squeezing of blood microvessels in 50-µm microvessels of mouse ear. After squeezing a 50-µm mouse ear blood vessel for 10 min, then quickly releasing the vessel, the rate of metastatic melanoma cells measured by PAFC immediately after vessel release increased approximately 8-fold, relative to the rate measured before squeezing. The degree of blood vessel squeezing could be controlled by monitoring increases and decreases in PA signal amplitudes.

The results of this experiment demonstrated that local enrichment of circulating metastatic melanoma cells was achieved through the mechanical restriction of circulatory vessels.

Example 14. The Background Absorption by Surrounding Blood Cells was Manipulated by Changes in Blood Oxygenation, Hematocrit, and Blood Osmolarity To determine the effects of changes in blood oxygenation, hematocrit, and osmolarity on the background absorption of blood cells during in vivo PAFC, the following experiment was conducted. The absorption of laser energy by hemoglobin in its oxygenated ($HbO_2$) and deoxygenated (Hb) forms differs, depending on the oxygen saturation state of the hemoglobin and the wavelength of the laser pulse. The total absorption of red blood cells decreases as oxygenation increases for laser pulse wavelengths 810-900 nm, and the absorption of red blood cells decreases with increasing blood oxygenation at laser pulse wavelengths of 650-780 nm. Thus, the oxygenation of the red blood cells can be manipulated to minimize the background PA signals emitted by the red blood cells.

Pure oxygen was delivered to a mouse using a mask around the mouse's head, and the background PA signal obtained before and after the increased blood oxygenation was measured using the in vivo PAFC system described in Example 2. The increased blood oxygenation resulting from the exposure of the mouse to pure oxygen for 15 minutes caused the background PA signal from veins to decrease by a factor of 1.36±0.14, using a laser pulse wavelength of 750 nm. Replacing the delivery of pure oxygen with the delivery of pure nitrogen led to a 35% decrease in background PA signal in an arteriole at a laser pulse rate of 900 nm.

Another experiment was conducted to assess the effects of decreasing the density of the circulating RBC as measured by the hemotocrit on the background signal from circulating red blood cells. The hemotocrit of a mouse's blood was temporarily reduced by the intravenous injection of 0.5 ml of standard saline solution into the vein tail. After the saline injection, PA signals from a 50-μm ear mouse vein dropped by a factor of 2.3±0.3, and nearly returned to initial levels within about 1.5 minutes.

Blood osmolarity causes an increase in the RBC volume (swelling) that resulted in a decrease in the average intracellular Hb concentration. Injection of 100-mL of hypertonic NaCl solution into the mouse tail vein led to an approximately 2-fold decrease in the PA signal in the ear vein.

The results of this experiment demonstrated that the background PA signals resulting from the emission of PA signals by red blood cells may be minimized by manipulation of the chemical environment of the blood, including blood oxygenation, hemotocrit, and blood osmolarity. These approaches may be readily applicable to human subjects because the procedures used in this experiment are routinely used in clinical practice.

Example 15. Microbubbles Conjugated with Nanoparticles were Assessed as a Contrast Agent for PAFC To assess the effectiveness of microbubbles conjugated with nanoparticles as a contrast agent in PAFC, the following experiment was conducted. Microbubbles (Definity Inc.) with average diameters of 2-4 μm were incubated with PEG-coated gold nanoshells (GNS), previously described in Example 10 for 1 hr at room temperature. The measurement of PA signals in vitro, as described in Example 1 was conducted for microbubbles only, GNS only and microbubbles conjugated with GNS. The microbubbles conjugated with GNS emitted the strongest PA signals, the GNS only emitted somewhat weaker PA signals, and the microbubbles alone emitted negligible PA signals (data not shown).

Increasing the energy of the laser pulses illuminating the GNS-conjugated microspheres led to a dramatic increase of the emitted PA signals, followed by the disappearance of the microbubbles after a single laser pulse. This observation was attributed to the laser-induced overheating of the GNS leading to a dramatic temperature increase of the gas trapped inside of the microbubbles that ultimately ruptured the microbubbles.

The results of this experiment demonstrated that microbubbles conjugated with GNS were an effective contrast agent, but that the energy of the laser pulses must be carefully moderated to avoid bursting the microbubbles. Because the microbubbles may be selectively attached to blood clots or taken up by activated white blood cells, this contrast agent may expand the potential applications of in vivo PAFC to include the detection of blood clots and certain activated white blood cells.

Example 16. Two-Wavelength In Vivo PAFC Used to Detect Circulating Exogenous Melanoma Cells To demonstrate the ability to use two-wavelength in vivo PAFC to detect injected unlabeled melanoma cells in circulation with extremely high sensitivity, the following experiment was conducted. B16F10 cultured mouse melanoma cells (ATCC, Rockville, MD) were obtained and maintained as described in Example 6. The experiments were performed using a nude mouse ear model similar, described in Example 2 (n=25). To mimic metastatic cells, approximately $10^5$ tumor-derived B16F10 cells in a 100-μl volume of saline solution were injected into the mouse circulatory system through a tail vein and then monitored in an ear vein using an apparatus and methods similar to those described in Example 10. An ear blood vessel was illuminated by two laser pulses at wavelengths of 865 nm and 639 nm with a 10-ms delay between the pulses.

Figure 14A:
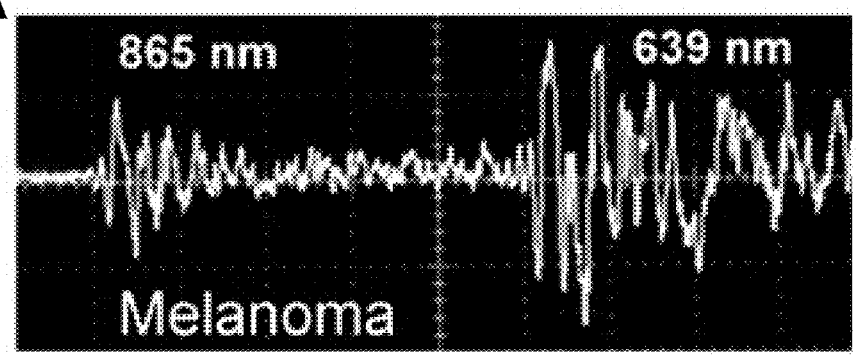
FIG. 14A shows oscilloscope traces of the two-wavelength, time-resolved detection of PA signals from melanoma cells absorbing 865 nm and 639 nm laser pulses.
Figure 14B:
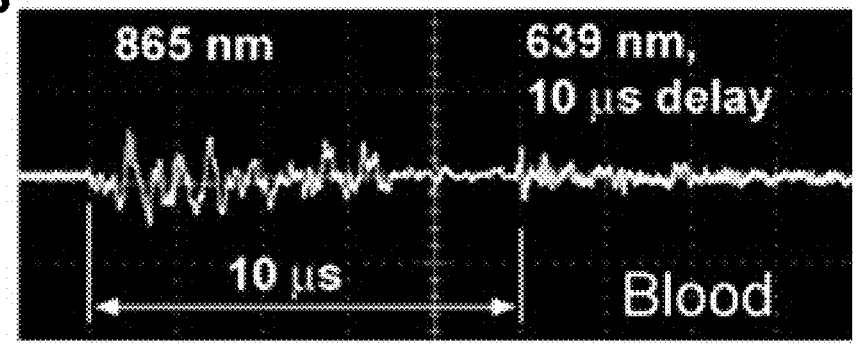
FIG. 14B shows oscilloscope traces of the two-wavelength, time-resolved detection of PA signals from red blood cells absorbing 865 nm and 639 nm laser pulses.

The melanoma cells were distinguished from surrounding blood cells, based upon the distinctive absorption spectra of the melanoma cells, as described previously in Example 6 and summarized in FIG. 9. Melanoma cells emitted two PA signals with a 10-ms delay, corresponding to the two laser pulses. The first PA signal, induced by the 639 nm laser pulse, had a higher amplitude than the PA signal induced by the 865 nm pulse, as shown in FIG. 14A. Red blood cells, the most numerous blood cells in circulation, generated two PA signals with lower amplitudes than the corresponding PA signals generated by the melanoma cells. In addition, for the red blood cells, the amplitude of the PA signal induced by the 865 nm pulse was slightly higher than the PA signal induced by the 639 nm laser pulse, as shown in FIG. 14B.

Figure 15:
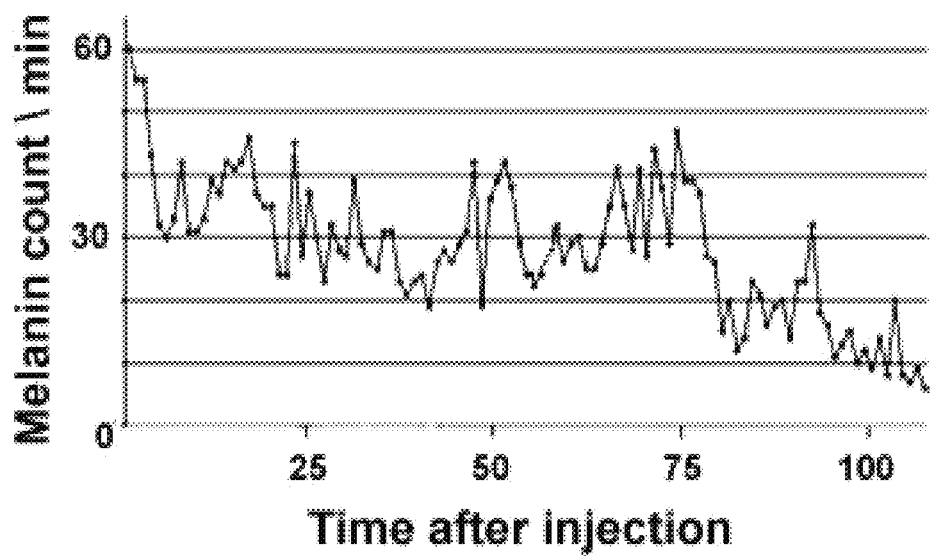
FIG. 15 is a summary of the PA signal rates from melanin particles detected in a mouse ear lymph microvessel 2 hours after injection.

The PA signals corresponding to the melanin particles were cleared over a two-hour period following the injection, as shown in FIG. 15.

Based on comparisons to similar data measured for melanoma cells labeled with markers that emitted strong PA signals, it was estimated that approximately 89% of the unlabelled melanoma cells were detected (data not shown). This percentage was lower than that found in previous in vitro studies (96%) and indicated a false-negative-signal rate of 1.5 cells/min because of the influence of background absorption by RBCs (data not shown). Longer-term monitoring of PA signals from ear blood vessels without prior melanoma cell injection detected no false-positive signals using as its criteria a signal-to-noise ratio where the signal noise was associated with fluctuations of laser energy and the density of red blood cells in the detected volume.

The results of this experiment demonstrated that two-color in vivo flow cytometry was an effective method of detecting metastatic melanoma cells in circulation. It was estimated that the method described above detected approximately 89% of the melanoma cells in circulation, with slightly lower detection rates due to skin pigmentation.

Example 17. Two-Wavelength In Vivo PAFC was Used to Detect Circulating Spontaneous Metastatic Cells During Tumor Progression An experiment was conducted to determine the ability of two-wavelength in vivo PAFC to detect relatively scarce endogenous metastatic melanoma cells circulating in lymph vessels. The PAFC system described in Example 10 was used to monitor endogenous metastatic melanoma cells in mice. Tumors were induced in nude mice by subcutaneous injections of melanoma cells using methods similar to those described in Example 7. Tumors formed and proliferated in the skin of the ear and the back of the nude mice over a period of 4 weeks, as previously described in Example 7.

Figure 16:
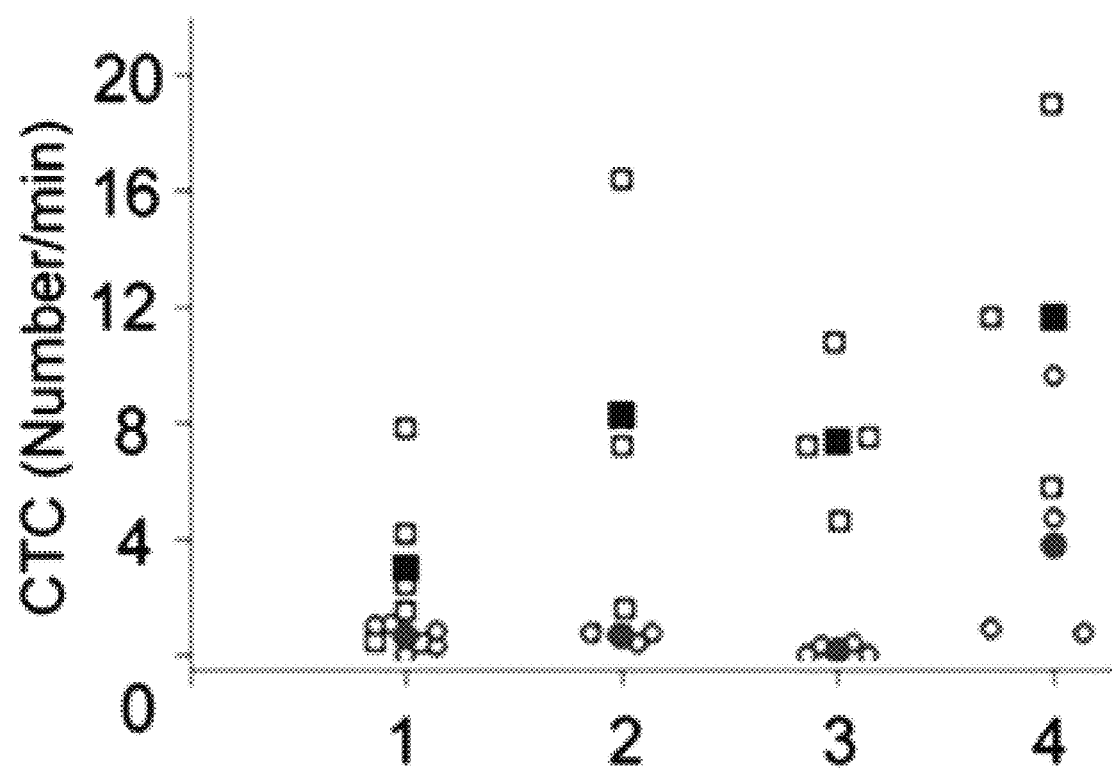
FIG. 16 is a summary of the PA signal rates from single melanoma cells detected in a mouse ear lymph microvessel 4 weeks after tumor inoculation.

PAFC was used to count spontaneous metastatic melanoma cells in an ~50 μm-diameter ear blood vessel and a 100-200-μm-diameter skin blood vessel during tumor progression in the ear and skin of a mouse, as summarized in FIG. 16. As previously described in Example 7, the skin tumor growth rate was faster than that of the ear tumors, and metastatic melanoma cells appeared more quickly in the circulation, as indicated by the mean cell detection rate measured in the skin capillaries, shown as solid square symbols in FIG. 16. In particular, within the first week after the induction of the tumors, about 1-4 melanoma cells/min were detected in the skin vasculature, and as the tumor size increased, the rate of detection of metastatic melanoma cells gradually increased to about 7 cells/min and about 12 cells/min after 3 weeks and 4 weeks, respectively.

The results of this experiment indicated that in vivo PAFC and PA mapping were sensitive methods with which to monitor the development of metastasized melanoma cells non-invasively, with high sensitivity and accuracy.

Example 18. PAFC System was Used to Determine Photoacoustic Response of Quantum Dot Markers In Vitro An experiment was conducted to determine the ability of two-wavelength in vivo PAFC to detect quantum dot cell markers in vitro. The PAFC system described in Example 2 was used to measure photoacoustic pulses emitted by quantum dots in response to laser pulses with wavelengths of 625 nm, pulse widths of 8 ns, and laser fluences ranging 0.001-10 J/m². The laser beam used to pulse the quantum dots had a diameter of about 20-30 µm in the sample plane. Quantum dots were obtained commercially with a polymer coating as well as with a streptavidin protein coating (Qdot 655 nanocrystals, Invitrogen, Carlsbad California). The quantum dots had diameters of about 15-20 nm and an emission wavelength of about 655 nm. Either single or aggregations of quantum dots were diluted with a buffer of 2% BSA/PBS and mounted in a layer of less than 1 µm on a microscope slide.

Figure 17:
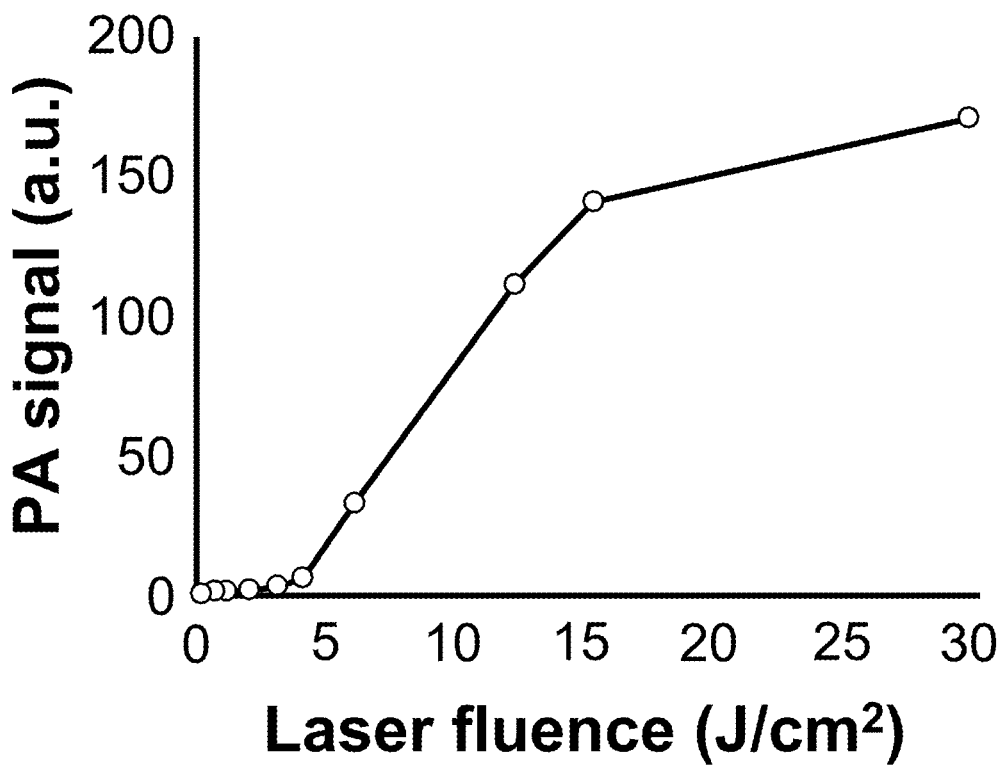
FIG. 17 is a summary of the PA signal amplitude generated by quantum dot markers as a function of laser fluence.

The PAFC system was used to pulse the quantum dot preparation with laser fluences ranging from 0.001-30 J/m². The magnitudes of the PA signals emitted by the quantum dots are summarized in FIG. 17. The PA signal response of the quantum dot preparations had a non-linear response to the variations in laser fluences. PA signal amplitude gradually increased in the laser fluence range from 0.1-1 J/cm². Through the laser fluence range between 1.5-7 J/cm², the response increased dramatically in a non-linear manner, and continued to increase in magnitude up to a laser fluence of 15 J/cm². At laser fluences above 15 J/m², the responses of the quantum dot preparations were saturated.

Figure 18:
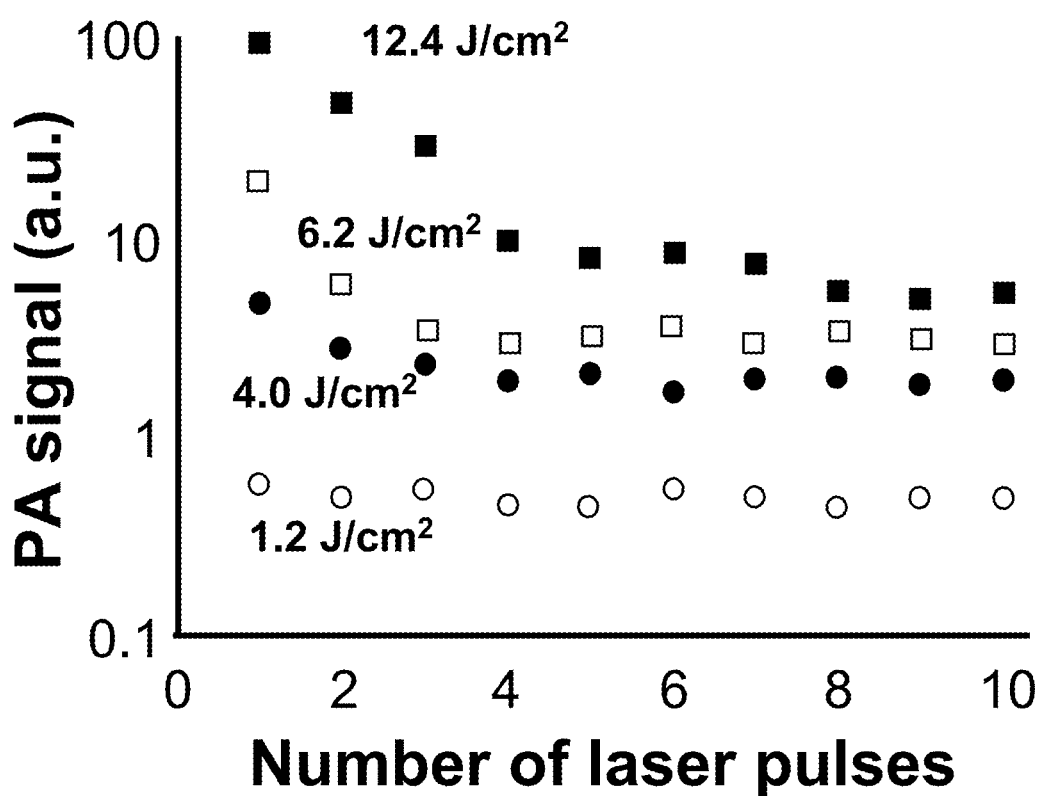
FIG. 18 is a summary of the PA signal amplitude generated by quantum dot markers as a function of the number of laser pulses.

The PA signal response as a function of the number of laser pulses for laser fluences of 1.2, 4.0, 6.2, and 12.4 J/cm² are summarized in FIG. 18. There was no sign of alteration of the laser pulse-induced PA signals at laser fluences below 3 J/cm², indicating no blinking behavior, unlike the stereotypical fluorescent blinking behavior observed in quantum dots. At higher laser fluences, significant decreases in the PA signal amplitude were observed with an increase in the number of pulses, possibly due to laser induced melting of thermal-based destruction by explosion of the quantum dots.

The results of this experiment indicated the quantum dots generated strong PA signals in response to laser pulses.

Example 19. PAFC System was Used to Detect Bacteria and Melanoma Cells Marked with Magnetic Nanoparticles In Vivo To demonstrate the application of magnetic nanoparticles as photoacoustic (PA) contrast agents, the following experiment was conducted.

S. aureus bacteria, described in Example 4, and melanoma cells, described in Example 6, were labeled with super paramagnetic iron oxide nanoparticles (Clementer Associates, Madison, CT). The nanoparticles consisted of a 50-nm core of magnetite ($Fe_3O_4$), coated with a 10-15 nm layer of Dextran and fluorescent dye. Both bacterial cells and melanoma cells were cultured at a density of approximately $10^6$ cells/m L, and magnetic nanoparticles were added to the cell cultures at a density of 0.5 mg/mL, and loaded into the cells by endocytosis for a minimum of 1 hour at 37° C. Labeled cells were centrifuged at 5,000 rpm for 3 minutes and the resulting pellet were resuspended in PBS.

The photoacoustic flow cytometry system (PAFC) system was similar in design to the PAFC system previously described in Example 2, with modifications to the laser, amplifier, and transducer components. A diode laser 905-FD1S3J08S (Frankfurt Laser Company) with driver (IL30C, Power Technology Inc, Little Rock, AR) was used to pulse the unbound magnetic nanoparticles and labeled cells with a pulse width of 15 ns, and a pulse repetition rate of 10 kHz. The laser beam dimensions used to pulse the nanoparticles and cells had an elliptical cross-section with minor and major axis dimensions of 11 µm and 75 µm, respectively, and a fluence energy maximum of 0.6 J/cm². The laser-induced PA signals were detected by a 5.5 mm-diameter, 3.5 MHz ultrasound transducer (model 6528101, (masonic Inc., Besancon, France), amplified using a 2 MHz amplifier (Panametrics model 5660B) and recorded with a Boxcar data recorder (Stanford Research Systems, Inc.) and a Tektronix TDS 3032B oscilloscope.

To determine the clearance rate of unbound magnetic nanoparticles, the nude mouse ear model described in Example 2 was used. A 100-mL PBS suspension of the magnetic nanoparticles at a concentration of about $10^{11}$ nanoparticles/mL was injected into the vein tail of the mice.

Figure 19:
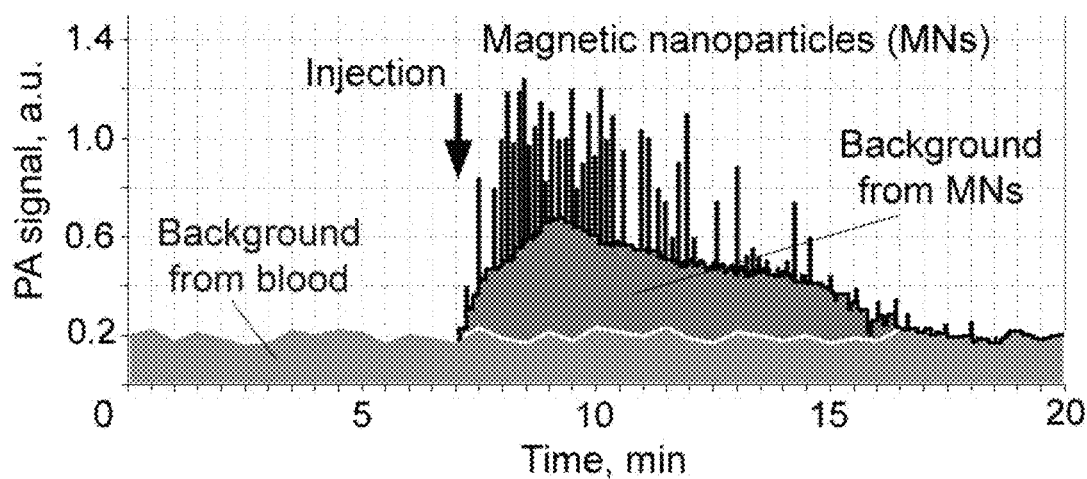
FIG. 19 is a summary of the PA signal amplitudes from a capillary over the 20 minutes following the injection of magnetic nanoparticles.

The magnetic nanoparticles were detected using the PAFC system described above. The laser pulses were delivered to the unbound magnetic nanoparticles at a wavelength of 639 nm and a laser fluence of 1.5 J/cm². The detection and subsequent clearance of the magnetic particles in the nude mouse ear model are summarized in FIG. 19. PA signals corresponding to the magnetic nanoparticles appeared within the first minute after injection. The PA signals were a combination of a fluctuating continuous PA background with superimposed large-amplitude PA signals. The magnitude of the background signal associated with the magnetic nanoparticles exceeded the PA background signals from the blood vessels by a factor of 2-3. The stronger but less frequent large-amplitude PA signals may be associated with random fluctuations of the number of magnetic nanoparticles in the detected volume and appearance of small aggregates of magnetic nanoparticles. The clearance time of the magnetic nanoparticles from the mouse ear microcirculation was in the range of 10-20 minutes.

Figure 20:
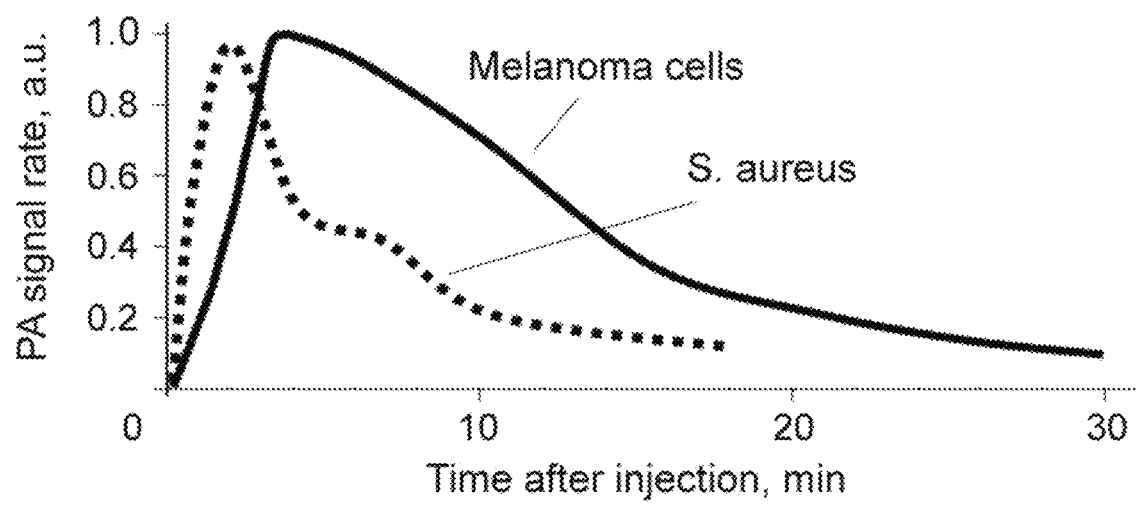
FIG. 20 is a summary of the PA signal rates from single melanoma cells and bacteria cells labeled with magnetic nanoparticles detected in a mouse ear capillary 30 minutes after injection.

Approximately $10^5$ B16F10 melanoma cells or S. aureus labeled with magnetic nanoparticles in 100 µL of saline solution were injected into a mouse tail vein and then monitored in the mouse ear using the PAFC system described above. Labeled melanoma cells were detected using a 905 nm, 0.4 J/cm² laser pulse, and the bacterial cells were detected using an 850 nm, 0.9 J/cm² laser pulse. The resulting PA signals emitted by S. aureus and melanoma cells labeled with magnetic nanoparticles are summarized in FIG. 20. Numerous PA signals from individual circulating cells were detected, with a maximum rate of detection within the first 1-3 minutes. The average half-life of the labeled bacteria and cancer cells in the blood microcirculation was 4.5 and 12 min, respectively.

Figure 21:
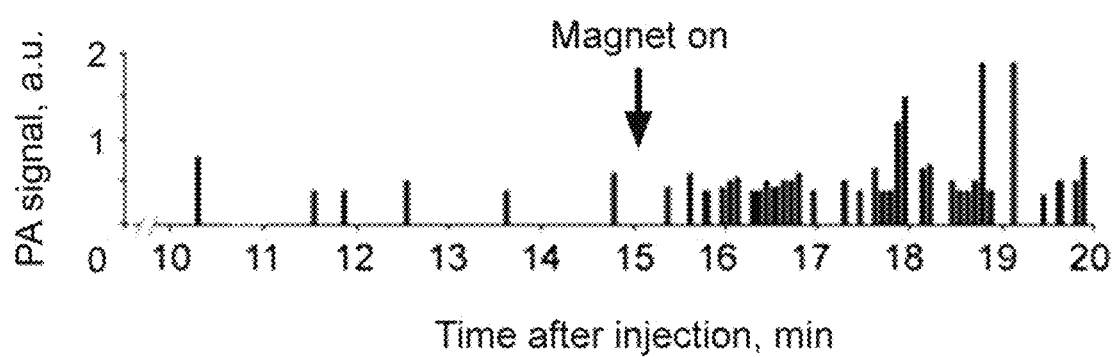
FIG. 21 is a summary of the PA signal rates from melanoma cells labeled with magnetic nanoparticles before and after the application of a magnetic field, detected in a mouse ear capillary 20 minutes after injection.
Figure 22:
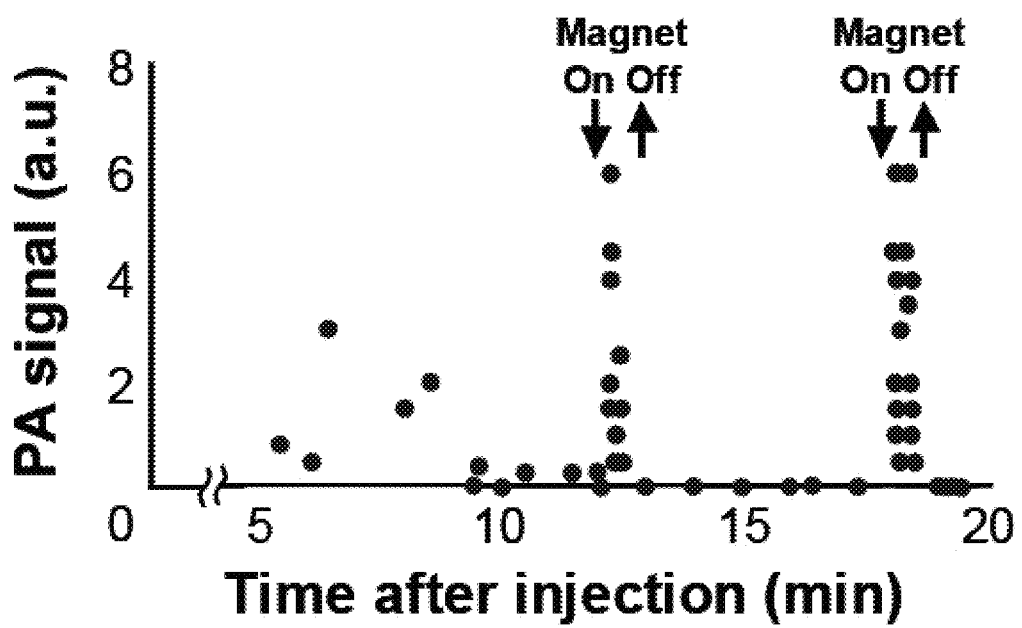
FIG. 22 is a summary of the PA signal rates from bacterial cells labeled with magnetic nanoparticles before and after the application of a magnetic field, detected in a mouse ear capillary 20 minutes after injection.

After the labeled melanoma cells and bacteria were essentially cleared from the circulation and only rare PA signals were detected, a local permanent magnetic field was imposed through intermediate tissue to the blood microvessels. The local permanent magnetic field was provided by a cylindrical Neodymium-Iron-Boron (NdFeB) magnet with Ni—Cu—Ni coating that was 3.2 mm in diameter and 9.5 mm long with a surface field strength of 0.39 Tesla (MAGCRAFT, Vienna, VA). The distance between the magnet and the microvessel walls ranged between 50-100 μm. As shown in FIGS. 21 and 22, the application of the magnetic field to the blood microvessels led to an immediate increase in both PA signal amplitudes and rate of detection in the vicinity of the magnet for the labeled melanoma cells and bacterial cells respectively.

The results of this experiment demonstrated that magnetic nanoparticles could be used to label circulating melanoma and bacteria cells for use in the prototype PAFC system. Further, a magnetic field applied to the blood microvessel in which the PAFC detected circulating cells was able to locally enrich the concentration of cells to be detected.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

REFERENCES

1. Ara, G. Anderson, R. R., Mandel K. G., Ottesen, M, Oseroff, A. R., (1990), "Irradiation of pigmented melanoma cells with high intensity pulsed radiation generates acoustic waves and kills cells." Lasers Surg Med, 10, 52-59.
2. Kim, J. W., Kotagiri, N., Kim, J. H., and Deaton, R, (2006), "In situ fluorescence microscopy visualization and characterization of nanometer-scale carbon nanotubules labeled with 1-pyrenebutanoic acid, succinimdylester," Appl. Phys. Lett., 88, 213110.
3. D. O. Lapotko and V. P. Zharov (2005). "Spectral evaluation of laser-induced cell damage with photothermal microscopy," Laser Surg. Med. 36, 22-33.
4. H. Liao and J. H. Hafner (2005). "Gold nanorod bioconjugates," Chem. Mater. 17, 4636-4641.
5. Weight, R. M., Viator, J. A., Dale, P. S., Caldwell, C. W., Lisle, A. E. (2006), "Photoacoustic detection of metastatic melanoma cells in the human circulatory system.", Opt Lett. 31, 2998-3000.
6. V. P. Zharov and D. O. Lapotko (2005). "Photothermal imaging of nanoparticles and cells (review)," IEEE J. Sel. Topics Quant. Electron. 11, 733-751
7. Zharov, V. P., Galanzha, E. I., Tuchin, V. V. (2006), "In vivo photothermal flow cytometry: imaging and detection of individual cells in blood and lymph flow.", J Cell Biochem. 97, 916-932.

What is claimed is:

1. A method of detecting individual fast moving target objects in vessels of a living organism, comprising:
    generating a focused elongated laser beam using a lens or an optical fiber as a series of consecutive laser pulses or modulated continuous radiation at different wavelengths in the x-ray spectra, visible spectra, terahertz spectra, or microwave spectra, the different wavelengths being between about 400 nm and about 2500 nm, wherein the different wavelengths are emitted at a pulse width ranging between about 0.1 ps and about 1000 ns, a pulse repeat rate ranging between about 1 Hz and about 500,000 Hz, and a pulse energy fluence ranging between about 0.1 mJ/cm$^2$ and about 1000 J/cm$^2$;
    simultaneously detecting photoacoustic, fluorescence, and scattering light signals from the same individual fast moving target object with a focused ultrasound transducer and a photodetector at a sample rate ranging between about 10 KHz and about 100 MHz; and
    analyzing one or more of the photoacoustic, fluorescence, and scattering light signals to determine presence of the target objects and at least one characteristic of the target object selected from a type of target object, quantity of target objects, a concentration of target objects, a flow speed of the target objects, a total blood volume, and combinations thereof based on one or more of a scattering of the laser pulses, a photothermal effect induced by the laser pulses, and a fluorescence induced by the laser pulses,
    wherein there is a time delay between each laser pulse of the series of consecutive laser pulses, the time delay ranging between 0.1 μs and about 100 μs.

2. The method of claim 1, wherein the laser beam comprises an elliptical cross-sectional shape, with long axis of the ellipse set to be diameter of the vessels, and short axis of the ellipse set to be diameter of the individual fast moving target object.

3. The method of claim 1, wherein the photoacoustic signal is a signature signal pattern associated with each type of individual fast moving target object, wherein the signature signal pattern comprises signal shape, frequency spectrum, amplitude, phase, and time delay between the laser pulse and the detected signal.

4. The method of claim 1, further comprising generating a second laser beam to provide time-resolved detection of the photoacoustic, fluorescence, and scattering light signals, wherein there is a time delay between the laser pulse and the detected signal, and the second laser beam has a wavelength ranging from 400 nm to 2,500 nm, and wherein the wavelength of the second laser beam is different from the wavelength of the first laser beam.

5. The method of claim 4, wherein the fluorescence and scattering light are induced by the second laser beam.

6. The method of claim 4, further comprising discriminating between different individual fast moving target objects, wherein the wavelength of the first laser beam and the wavelength of the second laser beam are selected to generate a unique signal amplitude and shape for each individual fast moving target object type.

7. The method of claim 6, wherein time-resolved detection of signals facilitates the discrimination between photoacoustic signals from individual fast moving target objects and background photoacoustic signals from skin, surrounding tissue or blood vessels at different depths.

8. The method of claim 4, wherein the first laser beam and/or the second laser beam are directed to a single location along one vessel, to two or more locations along a single vessel, or to a location on two or more vessels.

9. The method of claim 8, wherein the first laser beam and the second laser beam are applied at a known separation distance.

10. The method of claim 4, further comprising analyzing a width of the signal, a time delay between two signals produced by two distinct laser pulses of the first laser beam and the second laser beam applied at a known separation distance, or a frequency shift of the signal to determine flow speed of an individual fast moving target object.

11. The method of claim 1, further comprising:
introducing one or more absorbing dyes or blood cells labeled with marking compounds into blood or lymph vessels of the living organism; and
estimating the total volume of circulating blood or lymph volume using a degree of dilution of the one or more absorbing dyes or labeled blood cells.

12. The method of claim 1, wherein the individual fast moving target objects are selected from the group consisting of red blood cells, aggregated red blood cells, white blood cells, tumor cells, infected cells, bacteria, viruses, pathogens, clots, plaques, S. aureus, E. coli, necrotic and apoptotic cells, infected cells, inflamed cells, stem cells, dendritic cells, platelets, metastatic cancer cells resulting from melanoma, leukemia, breast cancer, prostate cancer, ovarian cancer, or testicular cancer, bacteria, viruses, fungal cells, protozoa, microorganisms, pathogens, animal cells, plant cells, leukocytes activated by various antigens during an inflammatory reaction, unlabeled biological cells with intrinsic cell-specific markers, products resulting from cell metabolism or apoptosis, cytokines or chemokines associated with response of immune system cells to infection, exotoxins and endotoxins produced during infections, gene markers of cancer cells, and combinations thereof.

13. The method of claim 12, wherein the intrinsic cell-specific markers are selected from the group consisting of hemoglobin (Hb), HbH, HbO, metHb, HbCN, HbS, HbCO, HbChr, myoglobins, melanin, cytochromes, bilirubin, catalase, porphyrins, chlorophylls, flavins, carotenoids, phytochromes, and psoralens.

14. The method of claim 12, wherein the gene markers of cancer cells are selected from the group consisting of tyrosinase mRNA p97, Melan A/Mart1, melanin produced by melanoma cells, PSA produced by prostate cancer, and cytokeratins produced by breast carcinoma.

15. The method of claim 12, further comprising detecting a disease and/or continuously monitoring the disease during treatment, wherein the disease is selected from the group consisting of metastasis, inflammation, infections, sepsis, immunodeficiency disorders, and cardiovascular disorders including strokes, heart attack, thrombosis and lung embolism.

16. The method of claim 1, further comprising:
adjusting timing of the laser pulses to synchronize with phasic rhythms of lymphatic flow;
detecting forward moving individual fast moving target objects by synchronizing the laser pulses with motion of the lymphatic vessel wall or lymphatic valves during forward flow of lymph; and/or
sensing the motion of the lymphatic vessel wall or lymphatic valves using an additional pilot laser pulse that produces signals used to trigger the laser pulses.

17. The method of claim 16, further comprising excluding detecting the same individual fast moving target object during their retrograde motion in the lymphatic vessels.

18. The method of claim 1, further comprising administering a contrast agent to increase the contrast of the photoacoustic, fluorescence, and scattering light signals from the individual fast moving target objects.

19. The method of claim 18, wherein the contrast agent is selected from the group consisting of indocyanine green dye, melanin, fluoroscein isothiocyanate (FITC) dye, Evans blue dye, Lymphazurin dye, trypan blue dye, methylene blue dye, propidium iodide, Annexin, Oregon Green, C3, Cy5, Cy7, Neutral Red dye, phenol red dye, AlexaFluor dye, Texas red dye, gold nanospheres, gold nanoshells, gold nanorods, gold cages, carbon nanoparticles, prefluorocarbon nanoparticles, carbon nanotubes, carbon nanohorns, magnetic nanoparticles, quantum dots, binary gold-carbon nanotube nanoparticles, multilayer nanoparticles, clustered nanoparticles, liposomes, liposomes loaded with contrast dyes, liposomes loaded with nanoparticles, micelles, micelles loaded with contrast dyes, micelles loaded with nanoparticles, microbubbles, microbubbles loaded with contrast dyes, microbubbles loaded with nanoparticles, dendrimers, aquasomes, lipopoly plexes, nanoemulsions, polymeric nanoparticles, and combinations thereof.

20. The method of claim 19, wherein the multilayer nanoparticles comprise two or more layers of materials with optical, thermal, and acoustic properties that enhance signals emitted by the target objects by enhancing absorption of the laser pulse energy, increasing thermal relaxation time, increasing acoustic relaxation time, increasing coefficient of thermal expansion, decreasing coefficient of thermal diffusion, decreasing the local speed of sound near the target object, decreasing threshold of bubble formation of the target object, or combinations thereof.

21. The method of claim 18, wherein the individual fast moving target objects are functionalized by antibodies, proteins, folates, receptors, peptides, amines, wheat germ agglutinin, and ligands for specific cell receptors including folate, epithelial cell adhesion molecule (Ep-CAM), Hep-2, PAR, CD44, epidermal growth factor receptor (EGFR), receptors of cancer cells, stem cells receptors, protein A receptors of Staphylococcus aureus, chitin receptors of yeasts, ligands specific to blood or lymphatic cell endothelial markers, or polysaccharide and siderophore receptors of bacteria.

22. The method of claim 18, wherein the contrast agent is introduced into circulatory or lymphatic vessels of the organism perenterally, orally, intradermally, subcutaneously, or by intravenous using a needle with the optical fiber or intraperitoneal administration.

23. The method of claim 1, further comprising locally concentrating the target objects in lumen of the vessel, wherein locally concentrating the target objects comprises:
reducing cross-sectional area of the lumen using gentle mechanical pressure on tissue; or
marking the target objects with magnetically active tags or markers and holding the target objects using a magnet with a magnetic field strength of at least seven Tesla, placed near the vessel.

24. The method of claim 1, further comprising:
exposing the organism to hyperoxic or hypoxic conditions to induce different levels of oxygenation and to increase contrast between signals originating from the target objects and background signals from surrounding cells and tissues, which in turn alters the light absorption properties of the red blood cells;
altering the osmolarity of the vessel flow by injecting hypertonic or hypotonic solutions into the vessel, thereby causing physical swelling or shrinking of surrounding cells, and further altering light absorption characteristics of the surrounding cells; and/or
altering the hematocrit of the vessel flow by injecting a diluting solution into the vessel, thereby reducing the density of surrounding cells in the vessel, and the resulting light absorption characteristics of surrounding cells.

25. The method of claim 1, further comprising:
selective ablating individual fast moving target objects by triggering a second laser pulse with an elliptical beam shape formed by the lens or the optical fiber at a wavelength and fluence sufficient to cause destruction of the detected individual fast moving target objects;

monitoring detection rate of the individual fast moving target objects; and terminating the detection and selective ablation when the detection rate of the individual fast moving target objects falls below a threshold level.

26. The method of claim 25, wherein the individual fast moving target objects selectively ablated are selected from the group consisting of red blood cells, white blood cells, aggregated red blood cells, contrast agents, tumor cells, infected cells, bacteria, viruses, pathogens, clots, plaques, sickle cells, and combinations thereof.

27. The method of claim 1, further comprising cooling skin above the individual fast moving target objects, wherein the skin is cooled by spray cooling, forced cooled air or liquid flow, an optically transparent cooling device attached to the skin and cooled using circulating cooled water or electrical effects, or combinations thereof.

28. A device for detecting individual fast moving target objects in vessels of a living organism, comprising:

a pulsed laser operates to generate a focused elongated laser beam using a lens or an optical fiber as a series of consecutive laser pulses or modulated continuous radiation at different wavelengths for simultaneous generation of fluorescence, scattering light and photoacoustic signals from the same individual fast moving target object at a laser different wavelengths ranging in the x-ray spectra, visible spectra, terahertz spectra, or microwave spectra, wherein the laser different wavelengths is between about 400 nm and about 2500 nm, the laser wavelength being emitted at a pulse width ranging between about 0.1 ps and about 1000 ns, a pulse repeat rate ranging between about 1 Hz and about 500,000 Hz, and a pulse energy fluence ranging between about 0.1 mJ/cm$^2$ and about 1000 J/cm$^2$, wherein the focused elongated laser beam comprises a series of consecutive laser pulses or modulated continuous radiation, wherein the series of consecutive laser pulses have a time delay between each laser pulse ranging between about 0.1 µs and about 100 µs;

an ultrasound transducer;

a photodetector, wherein the ultrasound transducer and the photodetector are configured to simultaneously receive fluorescence, scattering light and photoacoustic signals from the individual fast moving target objects and generate an output;

a data recording system; and a processor configured to analyze one or more of the fluorescence, scattering light, and photoacoustic signals to determine presence of the target objects and at least one characteristic of the target object selected from a type of target object, quantity of target objects, a concentration of target objects, a flow speed of the target objects, a total blood volume, and combinations thereof based on one or more of a scattering of the laser pulses, a photothermal effect induced by the laser pulses, and a fluorescence induced by the laser pulses.

29. The device of claim 28, wherein the ultrasound transducer comprises more than one ultrasound transducer.

30. The device of claim 28, wherein the ultrasound transducer is selected from the group consisting of a focused ultrasound transducer with conventional and cylindrical focused lengths between about 2 mm and about 500 mm or a resonance ultrasound transducer.

31. The device of claim 28, wherein the ultrasound transducer and the pulsed laser have a confocal configuration.

32. The device of claim 28, wherein the ultrasound transducer has a ring geometry with the pulsed laser passing through center of the ring of the ultrasound transducer.

33. The device of claim 28, further comprising an optical fiber placed in close vicinity of the individual fast moving target objects using a minimally invasive needle delivery device, an optic fiber mounting in a catheter, or a fiber-chip-based catheter inserted directly into the desired vessel.

34. The device of claim 33, wherein the photodetector is placed after the same optical fiber to detect the fluorescent or scattering light induced by the laser beam.

35. The device of claim 28, further comprising a hemodialysis system with artificial circulatory bypass tubes that are transparent to laser light in visible or near-infrared spectra, wherein the individual fast moving target objects are detected by shunting circulating individual fast moving target objects through the artificial circulatory bypass tubes.

36. The method of claim 1, wherein the living organism may be a mammal, a reptile, a bird, an amphibian, a fish, a plant, a fungi, a mollusk, an insect, an arachnid, an annelid, an arthropod, a roundworm, or a flatworm.

37. The method of claim 25, wherein the selective abating is thermal-based without harming surrounding cells.

\* \* \* \* \*